(12) United States Patent
Wisselink et al.

(10) Patent No.: US 9,034,608 B2
(45) Date of Patent: May 19, 2015

(54) POLYPEPTIDES WITH PERMEASE ACTIVITY

(75) Inventors: Hendrik Wouter Wisselink, Culemborg (NL); Antonius Jeroen Adriaan Van Maris, Delft (NL); Jacobus Thomas Pronk, Schipluiden (NL); Paul Klaassen, Dordrecht (NL); Rene Marcel De Jong, Amsterdam (NL)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

(21) Appl. No.: 13/822,288

(22) PCT Filed: Oct. 11, 2011

(86) PCT No.: PCT/EP2011/067726
§ 371 (c)(1),
(2), (4) Date: May 23, 2013

(87) PCT Pub. No.: WO2012/049173
PCT Pub. Date: Apr. 19, 2012

(65) Prior Publication Data
US 2013/0236932 A1    Sep. 12, 2013

Related U.S. Application Data

(60) Provisional application No. 61/392,617, filed on Oct. 13, 2010.

(30) Foreign Application Priority Data

Oct. 13, 2010  (EP) ..................... 10075710

(51) Int. Cl.
| | | |
|---|---|---|
| *C12P 19/18* | (2006.01) | |
| *C12P 7/56* | (2006.01) | |
| *C12P 7/16* | (2006.01) | |
| *C12P 7/06* | (2006.01) | |
| *C12P 7/14* | (2006.01) | |
| *C12N 9/12* | (2006.01) | |
| *C12N 1/00* | (2006.01) | |
| *C12P 21/06* | (2006.01) | |
| *C12P 19/34* | (2006.01) | |
| *C12N 15/00* | (2006.01) | |
| *C07H 21/04* | (2006.01) | |
| *C07K 1/00* | (2006.01) | |
| *C12N 15/81* | (2006.01) | |
| *C07K 14/395* | (2006.01) | |
| *C12P 7/10* | (2006.01) | |

(52) U.S. Cl.
CPC ............. *C12N 15/81* (2013.01); *C07K 14/395* (2013.01); *C12P 7/10* (2013.01); *Y02E 50/16* (2013.01); *C12N 9/1205* (2013.01); *C12P 7/06* (2013.01); *Y02E 50/17* (2013.01)

(58) Field of Classification Search
CPC .......... Y02E 50/17; Y02E 50/16; Y02E 50/10; C07K 14/395; C12N 15/81; C12N 9/1205; C12P 7/10; C12P 7/06
USPC .................. 435/97, 139, 160, 161, 162, 194, 435/254.11, 254.2, 254.21, 69.1, 91.1; 536/23.1, 23.2; 530/350
See application file for complete search history.

(56) References Cited

U.S. PATENT DOCUMENTS

2012/0208231 A1    8/2012    Van Maris et al.

FOREIGN PATENT DOCUMENTS

| WO | 2008/041840 | 4/2008 |
|---|---|---|
| WO | 2009/011591 | 1/2009 |
| WO | 2010/099153 | 9/2010 |
| WO | 2010/099343 | 9/2010 |
| WO | 2012/049170 | 4/2012 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
International Search Report & Written Opinion Based on Application No. PCT/EP2011/067726 Mailed February 1, 2012.
Becker et al.; "A Modified *Saccharomyces cerevisiae* Strain That Consumes L-Arabinose and Produces Ethanol"; Applied and Environmental Microbiology; Jul. 2003; vol. 69; No. 7; pp. 4144-4150; American Society for Microbiology.

(Continued)

*Primary Examiner* — Ganapathirama Raghu
(74) *Attorney, Agent, or Firm* — Miles & Stockbridge PC

(57) ABSTRACT

The invention relates to a polypeptide having a mutation at one or more position corresponding to T219 of SEQ ID NO: 55, wherein the polypeptide has at least 50% sequence identity with SEQ ID NO: 55, and wherein the polypeptide has permease activity.

14 Claims, 30 Drawing Sheets

(56) References Cited

OTHER PUBLICATIONS

Wisselink et al.; "Metabolome, Transcriptome and Metabolic Flux Analysis of Arabinose Firmintation by Engineerined *Saccharomyces cerevisiae*"; Metabolic Engineering; vol. 12; 2010; pp. 537-551; Elsevier Inc.

Van Maris et al.; "Alcoholic Fermentation of Carbon Sources in Biomass Hydrolysates by *Saccharomyces cerevisiae*: Current Status"; vol. 90; pp. 391-418; 2006; Springer.

Kasahara et al.; "Three Aromatic Amino Acid Residues Critical for Galactose Transport in Yeast GAL2 Transporter"; The Journal of Biological Chemistry; vol. 275; No. 6; Issue Feb. 11, 2000; pp. 4422-4428; the American Society for Biochemistry and Molecular Biology, Inc.

Kramarenko et al.; "Sugar Repression in the Methylotrophic Yeast Hansenula Polymorpha Studied by Using Hexokinase-Negative, Glucokinase-Negative and Double Kinase-Negative Mutants"; Folia Microbiol.; vol. 45; No. 6; 2000; pp. 521-529.

Diderich et al.; "Physiological Properties of *Saccharomyces cerevisiae* From Which Hexokinase II Has Been Deleted"; Applied and Environmental Microbiology; Apr. 2001; vol. 67; No. 4; pp. 1587-1593; American Society for Microbiology.

Raghevendran et al.; "Phenotypic Characterization of Glucose Repression Mutants of *Saccharomyces cerevisiae* Using Experiments With 13C-Labelled Glucose"; Yeast; vol. 21; 2004; pp. 769-779; John Wiley & Sons, Ltd.

Hahn-Haegerdal et al.; "Towards Industrial Pentose-Fermenting Yeast Strains"; Appl. Microbiol Biotechnol; 2007; vol. 74; pp. 937-953; Springer-Verlag.

Kuemmel et al.; "Differential Glucose Repression in Common Yeast Strains in Response to HXK2 Deletion"; FEMS Yeast Res; vol. 10; 2010; pp. 322-332; Federation of European Microbiology Societies; Blackwell Publishing Ltd.

Wisselink et al.; "Engineering of *Saccharomyces cerevisiae* for Efficient Anaerobic Alcoholic Fermentation of L-Arabinose"; Applied and Environmental Microbiology; Aug. 2007; vol. 73; No. 15; pp. 4881-4891; American Society for Microbiology.

Walsh et al.; "*Saccharomyces cerevisiae* Null Mutants in Glucose Phosphorylation: Metabolism and Invertase Expression"; Genetics; vol. 128; Jul. 1991; pp. 521-527; Genetics Society of America.

Wisselink et al; "Novel Evolutionary Engineering Approach for Accelerated Utilization of Glucose, Xylose, and Arabinose Mixtures by Engineered *Saccharomyces cerevisiae* Strains"; Applied and Environmental Microbiology; February 2009; vol. 75; No. 4; pp. 907-914.

Wedlock et al.; "Glucose-Negative Mutants of *Pachysolen tannophilus*"; Journal of General Microbiology; 1989; vol. 135; pp. 2019-2026; SGM.

Wedlock et al.; "Transformation of a Glucose Negative Mutant of *Pachysolen tannophilus* With a Plasmid Carrying the Cloned Hexokinase PII Gene From *Saccharomyces cerevisiae*"; Biotechnology Letters; vol. II; No. 9; 1989; pp. 601-604.

International Search Report Based on Application No. PCT/EP2011/067720 Mailed Apr. 17, 2012.

Raamsdonk et al.; "Co-Consumption of Sugars or Ethanol and Glucose in a *Saccharomyces cerevisiae* Strain Deleted in the HXK2 Gene"; Yeast; Aug. 2001; vol. 18; No. 11; pp. 1023-1033 (Abstract Only).

\* cited by examiner

```
GAL1 CEN.PK       1 mtkshseevivpefnssakelprplaekcpsiikkfisaydakpdfvarspgrvnligeh
GAL1 IMK318       1 ............................................................
GAL1 IMW017       1 ............................................................
GAL1 IMW018       1 ............................................................

GAL1 CEN.PK      61 idycdfsvlplaidfdmlcavkvlneknpsitlinadpkfaqrkfdlpldgsyvtidpsv
GAL1 IMK318      61 ............................................................
GAL1 IMW017      61 ............................................................
GAL1 IMW018      61 ............................................................

GAL1 CEN.PK     121 sdwsnyfkcglhvahsflkklaperfasaplaglqvfcegdvptgsglsssaaficaval
GAL1 IMK318     121 ............................................................
GAL1 IMW017     121 ............................................................
GAL1 IMW018     121 ............................................................

GAL1 CEN.PK     181 avvkanmgpgyhmskqnlmritvvaehyvgvnnggmdqaasvcgeedhalyvefkpqlka
GAL1 IMK318     181 ............................................................
GAL1 IMW017     181 ............................................................
GAL1 IMW018     181 ............................................................

GAL1 CEN.PK     241 tpfkfpqlknheisfviantlvvsnkfetaptnynlrvvevttaanvlaatygvvlpsgk
GAL1 IMK318     241 ............................................................
GAL1 IMW017     241 .........................f..................................
GAL1 IMW018     241 ............................................................

GAL1 CEN.PK     301 egsstnkgnlrdfmnvyyaryhnistpwngdiesgierltkmlvlveeslankkqgfsvd
GAL1 IMK318     301 ............................................................
GAL1 IMW017     301 ............................................................
GAL1 IMW018     301 ............................................................

GAL1 CEN.PK     361 dvaqslncsreeftrdylttspvrfqvlklyqrakhvyseslrvlkavklmttesftade
GAL1 IMK318     361 ...............v............................................
GAL1 IMW017     361 ...............v............................................
GAL1 IMW018     361 ...............v............................................

GAL1 CEN.PK     421 dffkqfgalmnesqascdklyecscpeidkicsialsngsygsrltgagwggctvhlvpg
GAL1 IMK318     421 ............................................................
GAL1 IMW017     421 ............................................................
GAL1 IMW018     421 ............................................................

GAL1 CEN.PK     481 gpngniekvkealanefykvkypkitdaelenaiivskpalgsclyel
GAL1 IMK318     481 ................................................
GAL1 IMW017     481 ................................................
GAL1 IMW018     481 ................................................
```

Fig.19

```
GAL2 CENPK  AA      1  maveennmpvvsqqpqagedvisslskdshlsaqsqkysndelkagesgpegsqsvpiei
GAL2 IMK318 AA      1  ............................................................
GAL2 IMW017 AA      1  ............................................................
GAL2 IMW018 AA      1  ............................................................

GAL2 CENPK  AA     61  pkkpmseyvtvsllclcvafggfmfgwdtgtisgfvvqtdflrrfgmkhkdgthylsnvr
GAL2 IMK318 AA     61  ............................................................
GAL2 IMW017 AA     61  ............................................................
GAL2 IMW018 AA     61  ............................................................

GAL2 CENPK  AA    121  tglivaifnigcafggiilskggdmygrkkglsivvsvyivgiiiqiasinkwyqyfigr
GAL2 IMK318 AA    121  ............................................................
GAL2 IMW017 AA    121  ............................................................
GAL2 IMW018 AA    121  ............................................................

GAL2 CENPK  AA    181  iisglgvggiavlcpmliseiapkhlrgtlvscyqlmitagiflgyctnygtksysnsvq
GAL2 IMK318 AA    181  ............................................................
GAL2 IMW017 AA    181  .................................n..........................
GAL2 IMW018 AA    181  ............................................................

GAL2 CENPK  AA    241  wrvplglcfawslfmigaltlvpesprylcevnkvedaklsiaksnkvspedpavqaeld
GAL2 IMK318 AA    241  ............................................................
GAL2 IMW017 AA    241  ............................................................
GAL2 IMW018 AA    241  ............................................................

GAL2 CENPK  AA    301  limagieaeklagnaswgelfstktkvfqrllmgvfvqmfqqltgnnyffyygtvifksv
GAL2 IMK318 AA    301  ............................................................
GAL2 IMW017 AA    301  ............................................................
GAL2 IMW018 AA    301  ............................................................

GAL2 CENPK  AA    361  glddsfetsivigvvnfastffslwtvenlgrrkclllgaatmmacmviyasvgvtrlyp
GAL2 IMK318 AA    361  ............................................................
GAL2 IMW017 AA    361  ............................................................
GAL2 IMW018 AA    361  .............s..............................................

GAL2 CENPK  AA    421  hgksqpsskgagncmivftcfyifcyattwapvawvitaesfplrvkskcmalasasnwv
GAL2 IMK318 AA    421  ............................................................
GAL2 IMW017 AA    421  ............................................................
GAL2 IMW018 AA    421  ............................................................

GAL2 CENPK  AA    481  wgfliafftpfitsainfyygyvfmgclvamffyvfffvpetkglsleeiqelweegvlp
GAL2 IMK318 AA    481  ............................................................
GAL2 IMW017 AA    481  ............................................................
GAL2 IMW018 AA    481  ............................................................

GAL2 CENPK  AA    541  wksegwipssrrgnnydledlqhddkpwykamle
GAL2 IMK318 AA    541  ..................................
GAL2 IMW017 AA    541  ..................................
GAL2 IMW018 AA    541  ..................................
```

POLYPEPTIDES WITH PERMEASE ACTIVITY

CROSS REFERENCE TO RELATED APPLICATIONS

This application is a §371 National Stage Application of PCT/EP2011/067726, filed Oct. 11, 2011, which claims priority to European Application No. 10075710.3, filed Oct. 13, 2010, and U.S. Provisional Application No. 61/392,617, filed Oct. 13, 2010.

BACKGROUND OF THE INVENTION

1. Field of the Invention

The invention is directed to novel polypeptides and to recombinant organisms expressing the polypeptides. In an embodiment, the present invention relates to novel permease polypeptides, more specifically to novel GAL2 in *Saccharomyces cerevisiae*.

2. Description of Related Art

Permeases are membrane transport proteins, a class of multipass transmembrane proteins that facilitate the diffusion of a specific molecule, herein specifically one or more sugar, in or out of the cell by passive transport. In contrast, active transporters couple molecule transmembrane transport with an energy source such as ATP or a favorable ion gradient.

In *Saccharomyces cerevisiae*, the permease GAL2 transports galactose across the cell membrane. It is also known as a transporter of glucose across the membrane.

SUMMARY

An object of the invention is to provide novel permease polypeptides. Another object of the invention is to provide recombinant strains expressing the permease polypeptide that have improved uptake of the molecule that the permease transports across the cell membrane. Another object is to provide a permease polypeptide that has a high affinity to C5 sugars, compared to a parent polypeptide. Another object is to provide a permease polypeptide that has reduced affinity to C6 sugar, compared to a parent polypeptide.

One or more of these objects are attained according to the invention. According to the present invention, there is provided a polypeptide having a mutation at a position corresponding to one or more position corresponding to T219 of SEQ ID NO: 55, wherein the polypeptide has at least 50% sequence identity with SEQ ID NO: 55, and wherein the polypeptide has permease activity. In an embodiment, the polypeptide has the substitution T219N or T219Q. In an embodiment, the polypeptide has substitutions T219N.

It is clear from FIGS. 17, 19 and 20, that a polypeptide having one or more of these mutations has an advantageous sugar consumption and/or fermentation production. See also example 18 below.

BRIEF DESCRIPTION OF THE DRAWINGS

FIG. 19 shows the GAL1 amino acid alignment of strains CEN.PK 113-7D, IMK318, IMW017 and IMW018.

FIG. 20 shows the GAL2 amino acid alignment of strains CEN.PK 113-7D, IMK318, IMW017 and IMW018.

BRIEF DESCRIPTION OF THE SEQUENCE LISTING

Figure 1:
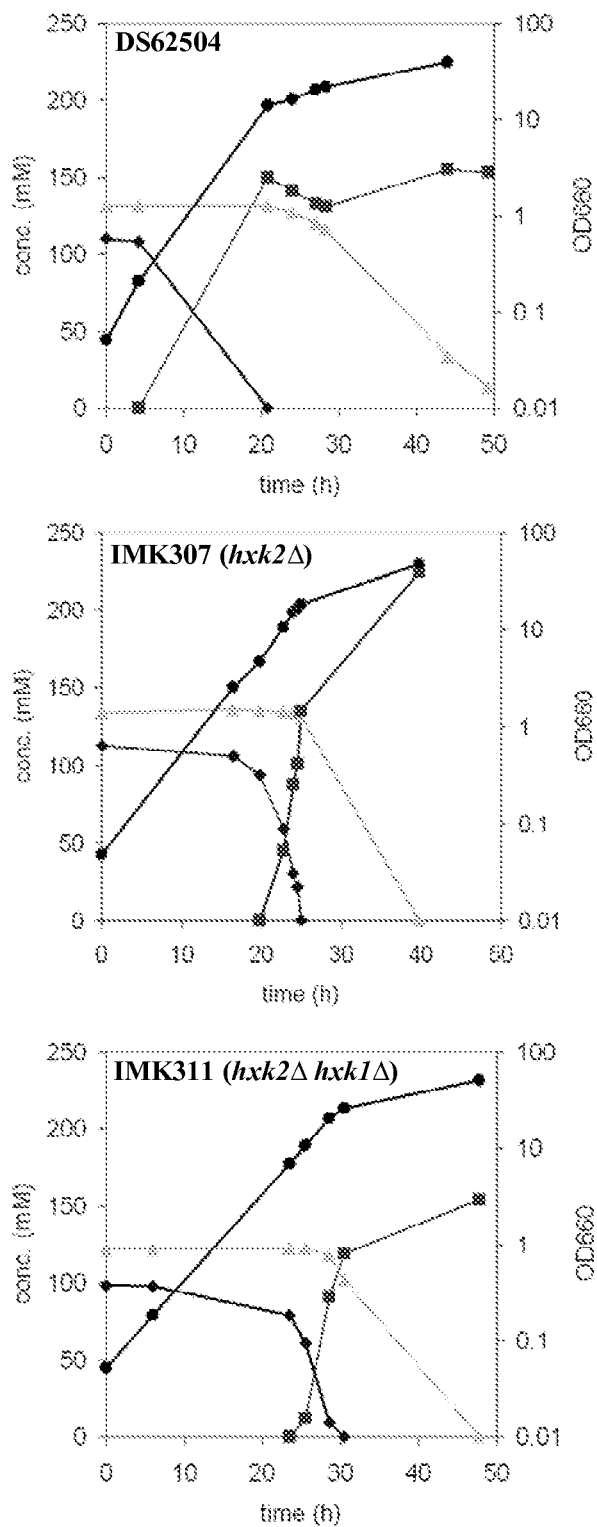
FIG. 1 shows glucose (♦), arabinose (▲) and ethanol (■) concentrations and optical density at 660 nm (OD660, ●) during shake flask cultivations of strains DS62504 (FIG. 1 (*a*)), IMK307 (FIG. 1 (*b*)) and IMK311 (FIG. 1 (*c*)).

Oligonucleotides used for construction of gene disruption cassettes:

SEQ ID NO: 1 sets out the sequence of oligonucleotide HXK2-disA
SEQ ID NO: 2 sets out the sequence of oligonucleotide HXK2-disB
SEQ ID NO: 3 sets out the sequence of oligonucleotide HXK1-disA
SEQ ID NO: 4 sets out the sequence of oligonucleotide HXK1-disB
SEQ ID NO: 5 sets out the sequence of oligonucleotide GLK1-disA
SEQ ID NO: 6 sets out the sequence of oligonucleotide GLK1-disB Oligonucleotides used for diagnostic purposes:

SEQ ID NO: 7 sets out the sequence of oligonucleotide KanA
SEQ ID NO: 8 sets out the sequence of oligonucleotide KanB
SEQ ID NO: 9 sets out the sequence of oligonucleotide HXK2-FW
SEQ ID NO: 10 sets out the sequence of oligonucleotide HXK2-RV
SEQ ID NO: 11 sets out the sequence of oligonucleotide HXK1-FW
SEQ ID NO: 12 sets out the sequence of oligonucleotide HXK1-RV
SEQ ID NO: 13 sets out the sequence of oligonucleotide GLK1-FW
SEQ ID NO: 14 sets out the sequence of oligonucleotide GLK1-RV
SEQ ID NO: 15 sets out the DNA sequence of HXK1
SEQ ID NO: 16 sets out the DNA sequence of HXK2
SEQ ID NO: 17 sets out the DNA sequence of GLK1
SEQ ID NO: 18 sets out the DNA sequence of GAL1
SEQ ID NO: 19 sets out the DNA sequence of YDR516c
SEQ ID NO: 20 sets out the DNA sequence of YLR446W
SEQ ID NO: 21 sets out the AMINO ACID sequence of HXK1
SEQ ID NO: 22 sets out the AMINO ACID sequence of HXK2
SEQ ID NO: 23 sets out the AMINO ACID sequence of GLK1
SEQ ID NO: 24 sets out the AMINO ACID sequence of GAL1
SEQ ID NO: 25 sets out the AMINO ACID sequence of YDR516c
SEQ ID NO: 26 sets out the AMINO ACID sequence of YLR446W
SEQ ID NO: 27 sets out the sequence of oligonucleotide GAL1-DisA
SEQ ID NO: 28 sets out the sequence of oligonucleotide GAL1-DisB
SEQ ID NO: 29 sets out the sequence of oligonucleotide GAL1-FW2
SEQ ID NO: 30 sets out the sequence of oligonucleotide GAL1-RV2
SEQ ID NO: 31 sets out the sequence of oligonucleotide HXK2-FW2
SEQ ID NO: 32 sets out the sequence of oligonucleotide HXK2-RV2
SEQ ID NO: 33 sets out the sequence of oligonucleotide HXK2-FW3
SEQ ID NO: 34 sets out the sequence of oligonucleotide HXK2-RV3
SEQ ID NO: 35 sets out the sequence of oligonucleotide HXK1-FW2
SEQ ID NO: 36 sets out the sequence of oligonucleotide HXK1-RV2
SEQ ID NO: 37 sets out the sequence of oligonucleotide HXK1-FW3

SEQ ID NO: 38 sets out the sequence of oligonucleotide HXK1-RV3

SEQ ID NO: 39 sets out the sequence of oligonucleotide GLK1-FW4

SEQ ID NO: 40 sets out the sequence of oligonucleotide GLK1-RV4

SEQ ID NO: 41 sets out the sequence of oligonucleotide GLK1-FW5

SEQ ID NO: 42 sets out the sequence of oligonucleotide GLK1-RV5

SEQ ID NO: 43 sets out the DNA sequence of GAL1 (CEN.PK 113-7D)

SEQ ID NO: 44 sets out the DNA sequence of GAL1 (IMK318)

SEQ ID NO: 45 sets out the DNA sequence of GAL1 (IMW017)

SEQ ID NO: 46 sets out the DNA sequence of GAL1 (IMW018)

SEQ ID NO: 47 sets out the DNA sequence of GAL2 (CEN.PK 113-7D)

SEQ ID NO: 48 sets out the DNA sequence of GAL2 (IMK318)

SEQ ID NO: 49 sets out the DNA sequence of GAL2 (IMW017)

SEQ ID NO: 50 sets out the DNA sequence of GAL2 (IMW018)

SEQ ID NO: 51 sets out the AMINO ACID sequence of GAL1 (CEN.PK 113-7D)

SEQ ID NO: 52 sets out the AMINO ACID sequence of GAL1 (IMK318)

SEQ ID NO: 53 sets out the AMINO ACID sequence of GAL1 (IMW017)

SEQ ID NO: 54 sets out the AMINO ACID sequence of GAL1 (IMW018)

SEQ ID NO: 55 sets out the AMINO ACID sequence of GAL2 (CEN.PK 113-7D)

SEQ ID NO: 56 sets out the AMINO ACID sequence of GAL2 (IMK318)

SEQ ID NO: 57 sets out the AMINO ACID sequence of GAL2 (IMW017)

SEQ ID NO: 58 sets out the AMINO ACID sequence of GAL2 (IMW018)

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The inbvention relates to polypeptides having a mutation at a position corresponding to one or more position corresponding to T219 of SEQ ID NO: 55, wherein the polypeptide has at least 50% sequence identity with SEQ ID NO: 55, and wherein the polypeptide has permease activity. In an embodiment, the mutations at the positions corresponding to T219 may be a substitution with C, P, G, A, V, L, I, M, F, W, Y, H, S, T, N, Q, D, E, K, R or a deletion. X may be any aminoacid, X(2) means two X.

In an embodiment, the polypeptide has the substitution T219N or T219Q. In an embodiment the polypeptide has substitution N376S or N376T. In an embodiment the polypeptide according to the invention has substitutions T219N and N376S.

Herein, GAL2 is a facilitated diffusion transporter required for both the high-affinity galactokinase-dependent and low-affinity galactokinase-independent galactose transport processes. It belongs to the major facilitator superfamily, sugar transporter (TC 2.A.1.1) family. "permease polypeptide", is also designated herein as "polypeptide permease" or "polypeptide". "Permease polypeptide polynucleotide", is herein a polynucleotide that encodes the permease polypeptide.

In an embodiment of the invention, the permease polypeptide has at least 60%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO: 55.

In an embodiment, the polypeptide according to the invention comprises one or more of the following amino acid or amino acid sequences:
a) G90;
b) G135;
c) G147;
d) G184-X(3)-G188-X(11)-E200-X(2)-P203-X(3)-R207-X(7)-Q215
e) Q215;
f) G345-X(1)-N347;
g) Y352;
h) Y446;
i) E460;
j) F504 and/or
k) E521.

wherein the positions in a) to k) in the polypeptide correspond to the positions in SEQ ID NO: 55. In an embodiment, the polypeptide comprises a sequence GXXXGXXXXXXXXXXXEXXPXXXRXXXXXXXQ.

Herein mutations are indicated by one letter aminoacids and positions of these amino acids. For example, A6 herein indicates an amino acid (one letter code) at a certain position in SEQ ID NO:1, here A (Alanine) at position 6 of the protein. A6 (L/N/Q/G/V/I/Y/S/E/K) indicates herein mutation of amino acid at a certain position, here A (Alanine) at position 6 of the protein is exchanged for any of L (Leucine), N (Asparagine), Q (Glutamine), G (Glycine), V (Valine), I (Isoleucine), Y (Tyrosine), S (Serine), E (Glutamic acid) or K (Lysine).

A permease polypeptide of the invention may have one or more alternative and/or additional activities other than that of sugar permease activity.

As set out above, a permease polypeptide of the invention will typically have sugar permease activity. However, a permease polypeptide of the invention may have one or more of the activities set out above in addition to or alternative to that activity.

Polynucleotide Sequence

With the permease polypeptide and its aminoacid sequence as disclosed herein, the skilled person may determine suitable polynucleotides that encode the permease polypeptide.

The invention therefore provides polynucleotide sequences comprising the gene encoding the permease polypeptide, as well as its coding sequence.

The polynucleotides of the invention may be isolated or synthesized. The permease polypeptides and permease polypeptide polynucleotides herein may be synthetic polypeptides, respectively polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization.

The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell.

The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art.

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polynucleotides of the present invention, such as a polynucleotide encoding the permease polypeptide can be isolated or synthesized using standard molecular biology techniques and the sequence information provided herein.

The polynucleotide encoding the permease polypeptide of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Transformation

The polynucleotides according to the invention may be expressed in a suitable host. Therefore standard transformation techniques may be used.

The invention further relates to a nucleic acid construct comprising the polynucleotide as described before, e.g. a vector.

Another aspect of the invention thus pertains to vectors, including cloning and expression vectors, comprising a polynucleotide of the invention encoding a permease polypeptide protein or a functional equivalent thereof and methods of growing, transforming or transfecting such vectors in a suitable host cell, for example under conditions in which expression of a permease of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein. The vectors, such as recombinant expression vectors, of the invention can be designed for expression of permease polypeptide proteins in prokaryotic or eukaryotic cells.

For example, permease polypeptides can be expressed in bacterial cells such as *E. coli*, insect cells (using baculovirus expression vectors), filamentous fungi, yeast cells or mammalian cells. Suitable host cells are discussed further in Goeddel, *Gene Expression Technology: Methods in Enzymology* 185, Academic Press, San Diego, Calif. (1990). Representative examples of appropriate hosts are described hereafter.

Appropriate culture mediums and conditions for the above-described host cells are known in the art.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2μ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd,ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

As indicated before, the invention provides an isolated polypeptide having the amino acid sequence according to SEQ ID NO: 55 with the mutations indicated in claim 1.

The permease polypeptide according to the invention can be recovered and purified from recombinant cell cultures by methods known in the art. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptides according to the invention.

Provided also are host cells, comprising a polynucleotide or vector of the invention. The polynucleotide may be heterologous to the genome of the host cell. The term "heterologous", usually with respect to the host cell, means that the polynucleotide does not naturally occur in the genome of the host cell or that the polypeptide is not naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are yeast cells including e.g. *Saccharomyces*, for example *Saccharomyces cerevisiae*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Herein standard isolation, hybridization, transformation and cloning techniques are used (e.g., as described in Sambrook, J., Fritsh, E. F., and Maniatis, T. Molecular Cloning: A Laboratory Manual.2nd, ed., Cold Spring Harbor Laboratory, Cold Spring Harbor Laboratory Press, Cold Spring Harbor, N.Y., 1989).

Homology & Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

The various embodiments of the invention described herein may be cross-combined.

The Sugar Composition

The sugar composition according to the invention comprises glucose, arabinose and xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 1. The listed lignocelluloses include: corn cobs, corn fiber, rice hulls, melon shells, sugar beet pulp, wheat straw, sugar cane bagasse, wood, grass and olive pressings.

TABLE 1

Overview of sugar compositions from lignocellulosic materials.

| Lignocellulosic material | Gal | Xyl | Ara | Man | Glu | Rham | Sum | %. Gal. | Lit. |
|---|---|---|---|---|---|---|---|---|---|
| Corn cob a | 10 | 286 | 36 | | 227 | 11 | 570 | 1.7 | (1) |
| Corn cob b | 131 | 228 | 160 | | 144 | | 663 | 19.8 | (1) |
| Rice hulls a | 9 | 122 | 24 | 18 | 234 | 10 | 417 | 2.2 | (1) |
| Rice hulls b | 8 | 120 | 28 | | 209 | 12 | 378 | 2.2 | (1) |
| Melon Shells | 6 | 120 | 11 | | 208 | 16 | 361 | 1.7 | (1) |
| Sugar beet pulp | 51 | 17 | 209 | 11 | 211 | 24 | 523 | 9.8 | (2) |
| Wheat straw Idaho | 15 | 249 | 36 | | 396 | | 696 | 2.2 | (3) |
| Corn fiber | 36 | 176 | 113 | | 372 | | 697 | 5.2 | (4) |
| Cane Bagasse | 14 | 180 | 24 | 5 | 391 | | 614 | 2.3 | (5) |
| Corn stover | 19 | 209 | 29 | | 370 | | 626 | | (6) |
| Athel (wood) | 5 | 118 | 7 | 3 | 493 | | 625 | 0.7 | (7) |
| Eucalyptus (wood) | 22 | 105 | 8 | 3 | 445 | | 583 | 3.8 | (7) |
| CWR (grass) | 8 | 165 | 33 | | 340 | | 546 | 1.4 | (7) |
| JTW (grass) | 7 | 169 | 28 | | 311 | | 515 | 1.3 | (7) |
| MSW | 4 | 24 | 5 | 20 | 440 | | 493 | 0.9 | (7) |
| Reed Canary Grass Veg | 16 | 117 | 30 | 6 | 209 | 1 | 379 | 4.2 | (8) |
| Reed Canary Grass Seed | 13 | 163 | 28 | 6 | 265 | 1 | 476 | 2.7 | (9) |
| Olive pressing residu | 15 | 111 | 24 | 8 | 329 | | 487 | 3.1 | (9) |

Gal = galactose,
Xyl = xylose,
Ara = arabinose,
Man = mannose,
Glu = glucose,
Rham = rhamnose.
The percentage galactose (% Gal) and literature source is given.

It is clear from table 1 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the transformed host cell.

The Transformed Host Cell

In an embodiment, the transformed host cell may comprise one or more copies of xylose isomerase gene and/or one or more copies of xylose reductase and/or xylitol dehydrogenase, and two to ten copies of araA, araB and araD, genes, wherein these genes are integrated into the cell genome.

In one embodiment, the transformed host cell comprises genes, for example the above xylose isomerase gene and/or one or more copies of xylose reductase and/or xylitol dehydrogenase, and two to ten copies of araA, araB and araD, genes, are integrated into the transformed host cell genome.

The number of copies may be determined by the skilled person by any known method. In the examples, a suitable method is described.

IN an embodiment, the transformed host cell is able to ferment glucose, arabinose, xylose and galactose.

In an embodiment, the cell is capable of converting 90% or more glucose, xylose arabinose, galactose and mannose available, into a fermentation product. In an embodiment, cell is capable of converting 91% or more, 92% or more, 94% or more, 95% or more, 96% or more, 97% or more, 98% or more or 100% of all glucose, xylose arabinose, galactose and mannose available, into a fermentation product.

In one embodiment of the invention the transformed host cell is able to ferment one or more additional sugar, preferably C5 and/or C6 sugar e.g. mannose. In an embodiment of the invention the transformed host cell comprises one or more of: a xyIA-gene, XYL1 gene and XYL2 gene and/or XKS1-gene, to allow the transformed host cell to ferment xylose; deletion of the aldose reductase (GRE3) gene; overexpression of PPP-genes TAL1, TKL1, RPE1 and RKI1 to allow the increase of the flux through the pentose phosphate pathway in the cell.

In an embodiment, the transformed host cell is an industrial cell, more preferably an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial transformed host cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

In an embodiment the transformed host cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions.

For phenolics: several tens of milligrams per liter, up to a gram per liter, depending on the feedstock, the pretreatment and the hydrolysis conditions.

The transformed host cells according to the invention may be inhibitor tolerant, i.e. they can withstand common inhibitors at the level that they typically have with common pretreatment and hydrolysis conditions, so that the transformed host cells can find broad application, i.e. it has high applicability for different feedstock, different pretreatment methods and different hydrolysis conditions.

In one embodiment, the industrial transformed host cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

In an embodiment, the transformed host cell is marker-free. As used herein, the term "marker" refers to a gene encoding a trait or a phenotype which permits the selection of, or the screening for, a host cell containing the marker. Marker-free means that markers are essentially absent in the transformed host cell. Being marker-free is particularly advantageous when antibiotic markers have been used in construction of the transformed host cell and are removed thereafter. Removal of markers may be done using any suitable prior art technique, e.g intramolecular recombination. A suitable method of marker removal is illustrated in the examples.

A transformed host cell may be able to convert plant biomass, celluloses, hemicelluloses, pectins, starch, starch derivatives, for example into fermentable sugars. Accordingly, a transformed host cell may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The transformed host cell further may comprise those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the transformed host cell is a cell that is naturally capable of alcoholic fermentation, preferably, anaerobic alcoholic fermentation. A transformed host cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a transformed host cell may be naturally present in the cell or may be introduced or modified by genetic modification.

Construction of the Transformed Host Cell

According to an embodiment, the genes may be introduced in the host cell by introduction into a host cell:
a) a cluster consisting of the genes araA, araB and araD under control of a strong constitutive promoter
b) a cluster consisting of PPP-genes TAL1, TKL1, RPE1 and RKI1, optionally under control of strong constitutive promoter; and deletion of an aldose reductase gene;
c) a cluster consisting of a xylA-gene and a XKS1-gene under control of strong constitutive promoter;
d) a construct comprising a xylA gene under control of a strong constitutive promoter, which has the ability to integrate into the genome on multiple loci; and adaptive evolution to produce the transformed host cell. The above cell may be constructed using recombinant expression techniques.

Recombinant Expression

The transformed host cell is a recombinant cell. That is to say, a transformed host cell comprises, or is transformed with or is genetically modified with a nucleotide sequence that does not naturally occur in the cell in question.

Techniques for the recombinant expression of enzymes in a cell, as well as for the additional genetic modifications of a transformed host cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of host cells are known from e.g. EP-A-0635 574, WO 98/46772, WO 99/60102, WO 00/37671, WO90/14423, EP-A-0481008, EP-A-0635574 and U.S. Pat. No. 6,265,186.

Typically, the nucleic acid construct may be a plasmid, for instance a low copy plasmid or a high copy plasmid. The cell according to the present invention may comprise a single or multiple copies of the nucleotide sequence encoding a enzyme, for instance by multiple copies of a nucleotide construct or by use of construct which has multiple copies of the enzyme sequence.

The nucleic acid construct may be maintained episomally and thus comprise a sequence for autonomous replication, such as an autosomal replication sequence sequence. A suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265,186).

Most episomal or 2μ plasmids are relatively unstable in yeast, being lost in approximately $10^{-2}$ or more cells after each generation. Even under conditions of selective growth, only 60% to 95% of the cells retain the episomal plasmid. The copy number of most episomal plasmids ranges from 20-100 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent. Typically, the enzyme encoding sequence will be operably linked to one or more nucleic acid sequences, capable of providing for or aiding the transcription and/or translation of the enzyme sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Promotors are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a transformed host cell, the 3'-end of the nucleotide acid sequence encoding enzyme preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the enzyme comprises a terminator. Preferably, such terminators are combined with mutations that prevent nonsense mediated mRNA decay in the host transformed host cell (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Antibiotic resistance markers may be most convenient for the transformation of polyploid host cells, Also non-antibiotic resistance markers may be used, such as auxotrophic markers (URA3, TRP1, LEU2) or the S. pombe TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0 635 574 and are based on the use of bidirectional markers such as the A. nidulans amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

The recombination process may thus be executed with known recombination techniques. Various means are known to those skilled in the art for expression and overexpression of enzymes in a transformed host cell. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters.

In an embodiment, the transformed host cell is markerfree, which means that no auxotrophic or dominant markers, in particular antibiotic resistance markers, are present in the genome or extra-chromosomally.

The coding sequence used for overexpression of the enzymes mentioned above may preferably be homologous to the host cell. However, coding sequences that are heterologous to the host may be used.

Overexpression of an enzyme, when referring to the production of the enzyme in a genetically modified cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Preferably in a host, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

Adaptation

Adaptation is the evolutionary process whereby a population becomes better suited (adapted) to its habitat or habitats. This process takes place over several to many generations, and is one of the basic phenomena of biology.

The term adaptation may also refer to a feature which is especially important for an organism's survival. Such adaptations are produced in a variable population by the better suited forms reproducing more successfully, by natural selection.

Changes in environmental conditions alter the outcome of natural selection, affecting the selective benefits of subsequent adaptations that improve an organism's fitness under the new conditions. In the case of an extreme environmental change, the appearance and fixation of beneficial adaptations can be essential for survival. A large number of different factors, such as e.g. nutrient availability, temperature, the availability of oxygen, etcetera, can drive adaptive evolution.

Fitness

There is a clear relationship between adaptedness (the degree to which an organism is able to live and reproduce in a given set of habitats) and fitness. Fitness is an estimate and a predictor of the rate of natural selection. By the application of natural selection, the relative frequencies of alternative phenotypes will vary in time, if they are heritable.

Genetic Changes

When natural selection acts on the genetic variability of the population, genetic changes are the underlying mechanism. By this means, the population adapts genetically to its circumstances. Genetic changes may result in visible structures, or may adjust the physiological activity of the organism in a way that suits the changed habitat.

It may occur that habitats frequently change. Therefore, it follows that the process of adaptation is never finally complete. In time, it may happen that the environment changes gradually, and the species comes to fit its surroundings better and better. On the other hand, it may happen that changes in the environment occur relatively rapidly, and then the species becomes less and less well adapted. Adaptation is a genetic process, which goes on all the time to some extent, also when the population does not change the habitat or environment.

The Adaptive Evolution

The transformed host cells may in their preparation be subjected to adaptive evolution. A transformed host cell may be adapted to sugar utilisation by selection of mutants, either spontaneous or induced (e.g. by radiation or chemicals), for growth on the desired sugar, preferably as sole carbon source, and more preferably under anaerobic conditions. Selection of mutants may be performed by techniques including serial transfer of cultures as e.g. described by Kuyper et al. (2004, FEMS Yeast Res. 4: 655-664) or by cultivation under selective pressure in a chemostat culture. E.g. in a preferred host cell at least one of the genetic modifications described above, including modifications obtained by selection of mutants, confer to the host cell the ability to grow on the xylose as carbon source, preferably as sole carbon source, and preferably under anaerobic conditions. When XI is used as gene to convert xylose, preferably the cell produce essentially no xylitol, e.g. the xylitol produced is below the detection limit or e.g. less than about 5, about 2, about 1, about 0.5, or about 0.3% of the carbon consumed on a molar basis.

Adaptive evolution is also described e.g. in Wisselink H. W. et al, Applied and Environmental Microbiology August 2007, p. 4881-4891

In one embodiment of adaptive evolution a regimen consisting of repeated batch cultivation with repeated cycles of consecutive growth in different media is applied, e.g. three media with different compositions (glucose, xylose, and arabinose; xylose and arabinose. See Wisselink et al. (2009) Applied and Environmental Microbiology, February 2009, p. 907-914.

Yeast Transformation and Genetic Stability

Genetic engineering, i.e. transformation of yeast cells with recombinant DNA, became feasible for the first time in 1978 [Beggs, 1978; Hinnen et al., 1978]. Recombinant DNA technology in yeast has established itself since then. A multitude of different vector constructs are available. Generally, these plasmid vectors, called shuttle vectors, contain genetic material derived from E. coli vectors consisting of an origin of replication and a selectable marker (often the β lactamase gene, ampR), which enable them to be propagated in E. coli prior to transformation into yeast cells. Additionally, the shuttle vectors contain a selectable marker for selection in yeast. Markers can be genes encoding enzymes for the synthesis of a particular amino acid or nucleotide, so that cells carrying the corresponding genomic deletion (or mutation) are complemented for auxotrophy or autotrophy. Alternatively, these vectors contain heterologous dominant resistance markers, which provides recombinant yeast cells (i.e. the cells that have taken up the DNA and express the marker gene) resistance towards certain antibiotics, like g418 (Geneticin), hygromycinB or phleomycin. In addition, these vectors may contain a sequence of (combined) restriction sites (multiple cloning site or MCS) which will allow to clone foreign DNA into these sites, although alternative methods exist as well.

Traditionally, four types of shuttle vectors can be distinguished by the absence or presence of additional genetic elements:

Integrative plasmids (YIp) which by homologous recombination are integrated into the host genome at the locus of the marker or another gene, when this is opened by restriction and the linearized DNA is used for transformation of the yeast cells. This generally results in the presence of one copy of the foreign DNA inserted at this particular site in the genome.

Episomal plasmids (YEp) which carry part of the 2μ plasmid DNA sequence necessary for autonomous replication in yeast cells. Multiple copies of the transformed plasmid are propagated in the yeast cell and maintained as episomes.

Autonomously replicating plasmids (YRp) which carry a yeast origin of replication (ARS, autonomously replicated sequence) that allows the transformed plasmids to be propagated several hundred-fold.

CEN plasmids (YCp) which carry in addition to an ARS sequence a centromeric sequence (derived from one of the nuclear chromosomes) which normally guarantees stable mitotic segregation and usually reduces the copy number of self-replicated plasmid to just one.

These plasmids are being introduced into the yeast cells by transformation. Transformation of yeast cells may be achieved by several different techniques, such as permeabilization of cells with lithium acetate (Ito et al, 1983) and electroporation methods.

In commercial application of recombinant microorganisms, plasmid instability is the most important problem. Instability is the tendency of the transformed cells to lose their engineered properties because of changes to, or loss of, plasmids. This issue is discussed in detail by Zhang et al (Plasmid stability in recombinant Saccharomyces cerevisiae. Biotechnology Advances, Vol. 14, No. 4, pp. 401-435, 1996). Strains transformed with integrative plasmids are extremely stable, even in the absence of selective pressure (Sherman, F. http://dbb.urmc.rochesteredu/labs/sherman_f/yeast/9.html and references therein).

The heterologous DNA is usually introduced into the organism in the form of extra-chromosomal plasmids (YEp, YCp and YRp). Unfortunately, it has been found with both bacteria and yeasts that the new characteristics may not be retained, especially if the selection pressure is not applied continuously. This is due to the segregational instability of the hybrid plasmid when recombinant cells grow for a long period of time. This leads to population heterogeneity and clonal variability, and eventually to a cell population in which the majority of the cells has lost the properties that were introduced by transformation. If vectors with auxotrophic markers are being used, cultivation in rich media often leads to rapid loss of the vector, since the vector is only retained in minimal media. The alternative, the use of dominant antibiotic resistance markers, is often not compatible with production processes. The use of antibiotics may not be desired from a registration point of view (the possibility that trace amounts of the antibiotic end up in the end product) or for economic reasons (costs of the use of antibiotics at industrial scale).

Loss of vectors leads to problems in large scale production situations. Alternative methods for introduction of DNA do exist for yeasts, such as the use of integrating plasmids (YIp). The DNA is integrated into the host genome by recombination, resulting in high stability. (Gaunt, P. Stability of recombinant plasmids in yeast. Journal of Biotechnology 9 (1988) 173-192). We have found that an integration method using the host transposons are a good alternative. In an embodiment genes may be integrated into the transformed host cell genome. Initial introduction (i.e. before adaptive evolution) of multiple copies be executed in any way known in the art that leads to introduction of the genes. In an embodiment, this may be accomplished using a vector with parts homologous to repeated sequences (transposons), of the host cell. When the host cell is a yeast cell, suitable repeated sequences are the long terminal repeats (LTR) of the Ty element, known as delta sequence. Ty elements fall into two rather similar subfamilies called Ty1 and Ty2. These elements are about 6 kilobases (kb) in length and are bounded by long terminal repeats (LTR), sequences of about 335 base pairs (Boeke J D et al, The *Saccharomyces cerevisiae* Genome Contains Functional and Nonfunctional Copies of Transposon Ty1. Molecular and Cellular Biology, April 1988, p. 1432-1442 Vol. 8, No. 4). In the fully sequenced *S. cerevisiae* strain, S288c, the most abundant transposons are Ty1 (31 copies) and Ty2 (13 copies) (Gabriel A, Dapprich J, Kunkel M, Gresham D, Pratt S C, et al. (2006) Global mapping of transposon location. PLoS Genet. 2(12): e212.doi:10.1371/journal.pgen.0020212). These transposons consist of two overlapping open reading frames (ORFs), each of which encode several proteins. The coding regions are flanked by the aforementioned, nearly identical LTRs. Other, but less abundant and more distinct Ty elements in *S. cereviaise* comprise Ty3, Ty4 and Ty5. For each family of full-length Ty elements there are an order of magnitude more solo LTR elements dispersed through the genome. These are thought to arise by LTR-LTR recombination of full-length elements, with looping out of the internal protein encoding regions.

The retrotransposition mechanism of the Ty retrotransposon has been exploited to integrate multiple copies throughout the genome (Boeke et al., 1988; Jacobs et al., 1988). The long terminal repeats (LTR) of the Ty element, known as delta sequences, are also good targets for integration by homologous recombination as they exist in about 150-200 copies that are either Ty associated or solo sites (Boeke, 1989; Kingsman and Kingsman, 1988). (Parekh R. N. (1996). An Integrating Vector for Tunable, High Copy, Stable Integration into the Dispersed Ty DELTA Sites of *Saccharomyces cerevisiae*. Biotechnol. Prog. 1996, 12, 16-21). By adaptive evolution, the number of copies may change.

The Host Cell

The host cell may be any host cell suitable for production of a useful product. A host cell may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a transformed host cell may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the suitable for use as a cell of the present invention are morphologically, physiologically, and genetically distinct from yeasts. Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

In one embodiment the host cell may be yeast.

Preferably the host is an industrial host, more preferably an industrial yeast. An industrial host and industrial yeast cell may be defined as follows. The living environments of yeast cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. Examples of industrial yeast (*S. cerevisiae*) are Ethanol Red® (Fermentis) Fermiol® (DSM) and Thermosacc® (Lallemand).

In an embodiment the host is inhibitor tolerant. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

araA, araB and araD Genes

A transformed host cell is capable of using arabinose. A transformed host cell is therefore, be capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a transformed host cell is order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591.

PPP-genes

A transformed host cell may comprise one ore more genetic modifications that increases the flux of the pentose phosphate pathway. In particular, the genetic modification(s) may lead to an increased flux through the non-oxidative part of the pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s = \mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RKI1.

The enzyme "transketolase" (EC 2.2.1.1) is herein defined as an enzyme that catalyses the reaction: D-ribose 5-phosphate+D-xylulose 5-phosphate <-> sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate <-> D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate:D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Xylose Isomerase or Xylose Reductase Genes

According to the invention, one or more copies of one or more xylose isomerase gene and/or one or more xylose reductase and xylitol dehydrogenase are introduced into the genome of the host cell. The presence of these genetic elements confers on the cell the ability to convert xylose by isomerisation or reduction.

In one embodiment, the one or more copies of one or more xylose isomerase gene are introduced into the genome of the host cell.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, such a transformed host cell is capable of isomerising xylose to xylulose. The ability of isomerising xylose to xylulose is conferred on the host cell by transformation of the host cell with a nucleic acid construct comprising a nucleotide sequence encoding a defined xylose isomerase. A transformed host cell isomerises xylose into xylulose by the direct isomerisation of xylose to xylulose.

A unit (U) of xylose isomerase activity may herein be defined as the amount of enzyme producing 1 nmol of xylulose per minute, under conditions as described by Kuyper et al. (2003, FEMS Yeast Res. 4: 69-78).

The Xylose isomerise gene may have various origin, such as for example *Pyromyces* sp. as disclosed in WO2006/009434. Other suitable origins are *Bacteroides*, in particular *Bacteroides uniformis* as described in PCT/EP2009/52623, *Bacillus*, in particular *Bacillus stearothermophilus* as described in PCT/EP2009/052625.

In another embodiment, one or more copies of one or more xylose reductase and xylitol dehydrogenase genes are introduced into the genome of the host cell. In this embodiment the conversion of xylose is conducted in a two step conversion of xylose into xylulose via a xylitol intermediate as catalysed by xylose reductase and xylitol dehydrogenase, respectively. In an embodiment thereof xylose reductase (XR), xylitol dehydrogenase (XDH), and xylokinase (XK) may be overexpressed, and optionally one or more of genes encoding NADPH producing enzymes are up-regulated and one or more of the genes encoding NADH consuming enzymes are up-regulated, as disclosed in WO 2004085627.

XKS1 Gene

A transformed host cell may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP:D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a transformed host cell, a genetic modification or modifications that increase(s) the specific xylulose kinase activity may be combined with any of the modifications increasing the flux of the pentose phosphate pathway as described above. This is not, however, essential.

Thus, a host cell may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

Aldose Reductase (GRE3) Gene Deletion

In the embodiment, where XI is used as gene to convert xylose, it may be advantageous to reduce aldose reducatase activity. A transformed host cell may therefore comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell (herein called GRE3 deletion). Transformed host cells may comprise multiple copies of genes encoding unspecific aldose reductases as a result of di-, poly- or aneu-ploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell is a nucleotide sequence encoding a polypeptide with aldose reductase activity.

Thus, a host cell comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

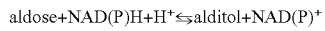

The enzyme has a wide specificity and is also known as aldose reductase; polyol dehydrogenase (NADP$^+$); alditol:NADP oxidoreductase; alditol:NADP$^+$ 1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

Bioproducts Production

Over the years suggestions have been made for the introduction of various organisms for the production of bio-ethanol from crop sugars. In practice, however, all major bioethanol production processes have continued to use the yeasts of the genus *Saccharomyces* as ethanol producer. This is due to the many attractive features of *Saccharomyces* species for industrial processes, i.e., a high acid-, ethanol-and osmotolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K fragilis.*

A transformed host cell may be a cell suitable for the production of ethanol. A transformed host cell may, however, be suitable for the production of fermentation products other than ethanol Such non-ethanolic fermentation products include in principle any bulk or fine chemical that is producible by a eukaryotic microorganism such as a yeast or a filamentous fungus.

A transformed host cell that may be used for production of non-ethanolic fermentation products is a host cell that contains a genetic modification that results in decreased alcohol dehydrogenase activity.

In an embodiment the transformed host cell may be used in a process wherein sugars originating from lignocellulose are converted into ethanol.

Lignocellulosek

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher tempatures, at a reaction time to release sufficient amounts of sugar(s). The result of the enzymatic hydrolysis is hydrolysis product comprising C5/C6 sugars, herein designated as the sugar composition.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L* Yps or more or may e.g. be 25*Yps g/L-250*Yps g/L, 30*Yps gl/L-200*Yps g/L, 40* Yps g/L-200*Yps g/L, 50*Yps g/L-200*Yps g/L, 60*Yps g/L-200*Yps g/L, 70* Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase. For example the fermentation products may be produced by cells according to the invention, following prior art cell preparation methods and fermentation processes, which examples however should herein not be construed as limiting. n-butanol may be produced by cells as described in WO2008121701 or WO2008086124; lactic acid as described in US2011053231 or US2010137551; 3-hydroxy-propionic acid as described in WO2010010291; acrylic acid as described in WO2009153047.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following examples illustrate the invention:

Strains and Maintenance. For storage of the strains used in this study (Table 1), shake flask cultures were performed in complex medium (YP), consisting of 10 g l$^{-1}$ yeast extract (BD Difco) and 20 g l$^{-1}$ peptone (BD Difco), supplemented with either 2% glucose (YPD), 2% ethanol+1.5% glycerol (YP-EtOH/Glyc) or 2% arabinose (YP-Ara). Cultures were incubated at 30° C. in an orbital shaker (200 rpm) until stationary growth phase. After addition of 30% (v/v) glycerol, samples from shake-flask cultures were stored in 2 ml aliquots at −80° C.

Shake-Flask Cultivation. Cultivation in shake flasks was performed at 30° C. in synthetic medium containing 2.3 g l$^{-1}$ urea, 6.6 g l$^{-1}$ K$_2$SO$_4$, 3 g l$^{-1}$ KH$_2$PO$_4$, 0.5 g l$^{-1}$ MgSO$_4$.7H$_2$O, and trace elements (MYurea) [7]. For shake flask cultivation, medium pH was adjusted to 4.7 with 2 M KOH prior to sterilization. After heat sterilization (121° C., 20 min), a filter-sterilized vitamin solution [7] and sugars were added. Shake-flask cultures were prepared by inoculating 100 ml medium containing the appropriate sugar in a 500-ml shake flask with a frozen stock culture, and incubated at 30° C. in an orbital shaker (200 rpm).

Anaerobic Batch Cultivation. Anaerobic batch cultivation was carried out at 30° C. in 2 liter fermenters (Applikon, Schiedam, the Netherlands) with a working volume of 1 l. Cultures were performed in synthetic medium containing 5 g l$^{-1}$ (NH$_4$)$_2$SO$_4$, 3 g l$^{-1}$ KH$_2$PO$_4$, 0.5 g l$^{-1}$ MgSO$_4$.7H$_2$O and trace elements [7]. After heat sterilization (121° C., 20 min.) the medium was supplemented with 0.01 g l$^{-1}$ ergosterol and 0.42 g l$^{-1}$ Tween 80 dissolved in ethanol [1,2], silicon antifoam, trace elements, filter sterilized vitamin solution [7], and the appropriate carbon source. Cultures were stirred at 800 rpm and sparged with 0.5 l min$^{-1}$ nitrogen gas (<10 ppm oxygen) and were maintained at pH 5.0 by automatic addition of 2 M KOH. To minimize oxygen diffusion, fermenters were equipped with Norprene tubing (Cole Palmer Instrument Company, Vernon Hills, USA). Absence of oxygen was verified with an oxygen electrode (Applisens, Schiedam, the Netherlands). Batch cultivations were started by inoculation with a 100 ml glucose-grown shake flask culture.

Growth Rate Determination. For shake flask cultures growth profiles were made by measuring the optical density at 660 nm (OD660) in time. For anaerobic cultivations in fermenters the specific growth rates were determined based on the CO$_2$ concentrations in the exhaust gas. The specific growth rates were determined by fitting data points with an exponential curve.

Carbon Dioxide and Extracellular Metabolite Analysis.

Exhaust gas from anaerobic fermenters was cooled in a condenser (2° C.) and dried with a Permapure dryer type MD-110-48P-4 (Permapure, Toms River, USA). Carbon dioxide concentrations were determined with a NGA 2000 analyzer (Rosemount Analytical, Orrville, USA). Exhaust gas flow rates and specific carbon dioxide production rates were determined as described previously [6,8].

Glucose, arabinose, acetate, lactate, succinate, glycerol and ethanol were analyzed by HPLC using a Waters Alliance 2690 HPLC (Waters, Milford, USA) supplied with a BioRad HPX 87H column (BioRad, Hercules, USA), a Waters 2410 refractive-index detector and a Waters 2487 UV detector. The column was eluted at 60° C. with 0.5 g l$^{-1}$ sulfuric acid at a flow rate of 0.6 ml min$^{-1}$.

Hexokinase Activity Determination. Hexokinase activity in cell extracts of the used strains in this study is determined by measuring the conversion of glucose into glucose-6-phosphate (reaction 1), using a coupled enzymatic reaction (reaction 2) that converts the formed glucose-6-phosphate into 6-phosphogluconate by the enzyme glucose-6-phosphate dehydrogenase. The rate of NADPH formed in this coupling reaction is equal to the hexokinase activity and is determined by measuring the absorbance at 340 nm.

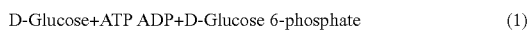

D-Glucose+ATP ADP+D-Glucose 6-phosphate (1)

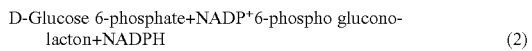

D-Glucose 6-phosphate+NADP$^+$ 6-phospho glucono-lacton+NADPH (2)

EXAMPLE 1

Gene Deletions

Gene deletions herein were achieved by integration of a G418 resistance cassette replacing the target gene. For the deletion of HXK2, HXK1 and GLK1, the KanMX cassette from pUG6 was amplified by PCR [4], using oligonucleotides indicated in Table 2.

TABLE 2

Oligonucleotides used in this study for the construction of gene deletions and related diagnostic purposes. A KanMX gene deletion cassette was obtained by PCR by using combinations of the DisA and DisB oligonucleotides. Genes were disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene (e.g. KanA combined with HXK2-FW and KanB combined with HXK2-RV).

| Name | 5'-3' DNA sequence |
|---|---|
| *Oligonucleotides used for construction of gene disruption cassettes* | |
| HXK2-disA | <u>GTTGTAGGAATATAATTCTCCACACATAATAAGTACGCTAATT</u>CAGCTGAAGCTTCGTACGC |
| HXK2-disB | <u>AAAAGGGCACCTTCTTGTTGTTCAAACTTAATTTACAAATTAAGT</u>GCATAGGCCACTAGTGGATCTG |
| HXK1-disA | <u>TTTCTTTTAATCAAACTCACCCAAACAACTCAATTAGAATACTG</u>CAGCTGAAGCTTCGTACGC |
| HXK1-disB | <u>GAATAATAATATTAAGGGAGGGAAAAACACATTTATATTTCATTAC</u>AGCATAGGCCACTAGTGGATCTG |
| GLK1-disA | <u>CTCGGACAAAGGTCTTCCTATGATTCCGGCGTTCGTCACCGGGT</u>CCAGCTGAAGCTTCGTACGC |
| GLK1-disB | <u>TAAAGGAGAGAAGATGGTAAGTACGGTGGGATACGTACACAAAC</u>ATAGGCCACTAGTGGATCTG |
| *Oligonucleotides used for diagnostic purposes* | |
| KanA | CGCACGTCAAGACTGTCAAG |
| KanB | TCGTATGTGAATGCTGGTCG |

TABLE 2-continued

Oligonucleotides used in this study for the construction of gene deletions and related diagnostic purposes. A KanMX gene deletion cassette was obtained by PCR by using combinations of the DisA and DisB oligonucleotides. Genes were disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene (e.g. KanA combined with HXK2-FW and KanB combined with HXK2-RV).

| Name | 5'-3' DNA sequence |
| --- | --- |
| HXK2-FW | TTCGCCACTGTCTTATCTAC |
| HXK2-RV | CCGTTCGTTCCAGAATTATC |
| HXK1-FW | CCTTAGGACCGTTGAGAGGAATAG |
| HXK1-RV | TCCCGGAGAACAAAGTAAGTGG |
| GLK1-FW | AAAAACGGGAAATAACAATAACGAC |
| GLK1-RV | TGCGATCTTATTAGTGTGTGACATT |

After purification of the PCR products (GenElute PCR Clean-up Kit, Sigma, Steinheim, Germany), overnight cultures were transformed [3] with the gene disruption cassette. Transformed cells were selected on YPD-agar containing 100 μg ml⁻ G418 (InvivoGen, San Diego, USA). Correct integration of the KanMX cassette was verified by PCR on single colonies using diagnostic oligonucleotides that bind to the KanMX cassette and regions up- and downstream of the target gene (Table 1).

For multiple gene deletions, the KanMX marker was rescued before deletion of the next gene. To this end, cells were transformed with pSH65, expressing the inducible Cre-recombinase and carrying the phleomycin resistance gene ble$^r$ [5]. Transformed cells were spread on YPD plates containing phleomycin and incubated at 30° C. until colonies appeared. Liquid YP-galactose containing 7.5 μg/ml phleomycin (InvivoGen, San Diego, USA) was inoculated with several phleomycin resistant colonies, incubated overnight at 30° C. for induction of the-Cre recombinase, and transferred to solid YPD with phleomycin. Removal of the KanMX cassette by the Cre-recombinase was confirmed by replica plating of phleomycin-resistant yeast colonies on YPD and YPD-G418 and by diagnostic PCR on single colonies that had lost G418 resistance. Subsequently, loss of pSH65 was achieved by growing cells non-selectively for 5-10 generations in YPD without phleomycin, after which loss of phleomycin resistance was confirmed by replica plating of single colonies on solid YPD with and without phleomycin. Subsequent deletion of HXK2, HXK1 and GLK1, and removal of the KanMX gene after each deletion, resulted in strains IMK306, IMK307, IMK311, IMK312 and IMK318 (Table 3).

TABLE 3

*S. cerevisiae* strains constructed and used herein.

| Strain | Relevant genotype/characteristics |
| --- | --- |
| DS62504 | MAT a MAL2-8c SUC2 ygr059w::{TDH3p-araA; ENO1p-araB; PGI1p-araD} gre3::{TPI1p-TAL1; ADH1p-TKL1; PGI1p-RPE1; ENO1p-RKI1} yel023c::{TPI1p-XylA; TDH1p-XKS1} |
| IMK306 | As DS62504; Δhxk2::LoxP-KanMX-LoxP |
| IMK307 | As DS62504; Δhxk2::LoxP |
| IMK311 | As DS62504; Δhxk2::LoxP Δhxk1::LoxP-KanMX-LoxP |
| IMK312 | As DS62504; Δhxk2::LoxP Δhxk1::LoxP |
| IMK318 | As DS62504; Δhxk2::LoxP Δhxk1::LoxP glk1::LoxP-KanMX-LoxP |
| IMW017 | As DS62504; Δhxk2::LoxP Δhxk1::LoxP glk1::LoxP-KanMX-LoxP; single colony isolate derived from IMK318, selected for glucose-insensitive arabinose consumption; co-consuming glucose and arabinose |
| IMW018 | As DS62504; Δhxk2::LoxP Δhxk1::LoxP glk1::LoxP-KanMX-LoxP; single colony isolate derived from IMK318, selected for glucose-insensitive arabinose consumption; consuming arabinose in the presence of >2% (w/v) glucose |

Figure 2:
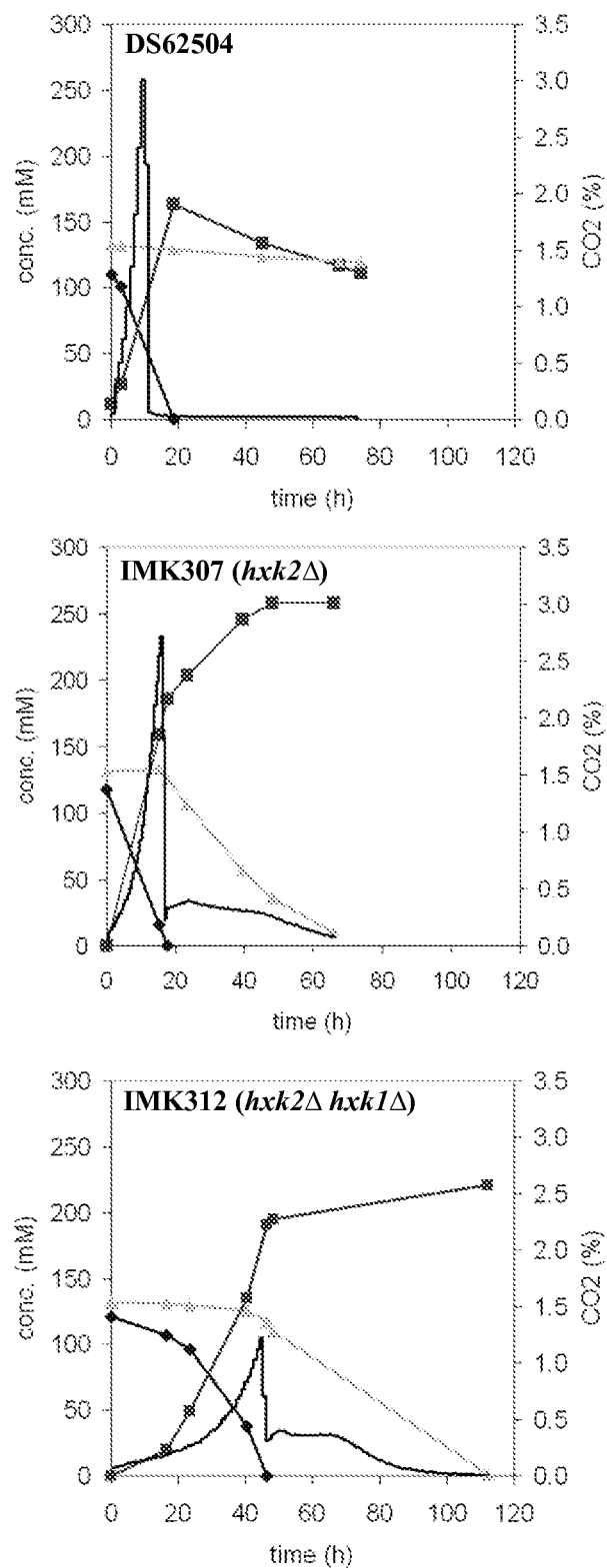
FIG. 2 shows glucose (♦), arabinose (▲) and ethanol (■) concentrations and $CO_2$ percentage in the exhaust gas (solid black line) during anaerobic cultivations of strains DS62504 (FIG. 2 (*a*)), IMK307 (FIG. 2 (*b*)) and IMK311 (FIG. 2 (*c*)). Fermentations were inoculated with glucose-grown shake flask cultures.

The Effect of hxk2 and hxk2 Hxk1 Deletion on Glucose and Arabinose Consumption. To determine the effect of HXK2 and HXK1 deletion on glucose and arabinose consumption, strains DS62504, IMK307 (hxk2Δ) and IMK311/IMK312 (hxk2Δ hxk1Δ) were cultivated both in shake flasks (FIG. 1) and anaerobic fermenters (FIG. 2) at 30° C. in MY supplemented with a mixture of 2% arabinose and 2% glucose.

The shake flask cultures were started at an initial OD660 of approximately 0.05 by inoculation with shake flask cultures grown in MY-glc. Strain DS62504 (FIG. 1) consumed glucose within 21 hours and upon glucose depletion, arabinose consumption started. Both sugars were consumed in a total time of more than 50 hours. In the culture of strain IMK307 (FIG. 1), glucose was totally consumed with 25 hours and arabinose was depleted in less than 15 hours after that. Overall IMK307 demonstrated an at least 20% reduction in total fermentation time compared to DS62504. Strain IMK311 (FIG. 1) consumed 2% glucose within approximately 30 hours. With still approximately 10 mM of glucose left in the culture, arabinose consumption was observed. The arabinose was completed within 48 hours. Although slower than IMK307, the overall fermentation time of IMK311 was still shorter than that of DS62504.

The anaerobic cultivations (FIG. 2) were started at an initial OD660 of approximately 1 by inoculation with shake flaks cultures grown in MY-glc. Based on the $CO_2$ production profile it could be deduced that strain DS64205 completely consumed the glucose within less than 15 hours. The specific growth rate during glucose consumption was 0.29 h$^{-1}$. The arabinose however, was consumed at a much lower rate. After 80 hours, approximately 90% of the arabinose is still present in the fermentation broth. Glucose consumption for strain IMK307 (hxk2Δ) was slower. Both the $CO_2$ production profile and the glucose measurements indicated that all the glucose was consumed within 20 hours. The specific growth rate during glucose consumption was 0.20 h$^{-1}$. Arabinose consumption started upon glucose depletion and 92% of the arabinose was consumed within 66 hours, which is a clear improvement if compared to strain DS62504. Deletion of HXK1 additional to HXK2 (strain IMK312) had a severe effect on the specific growth rate on glucose. The growth rate 0.05 h$^{-1}$ for strain IMK312 was 75% lower than that of strain IMK307. Glucose was depleted within 46 hours. Within these 46 hours, approximately 10% of the total of 132 mM of arabinose was consumed. Arabinose was completely consumed within less than 112 hours.

EXAMPLE 2

Selection of IMK318 Growing on Arabinose in the Presence of Glucose

Figure 3:
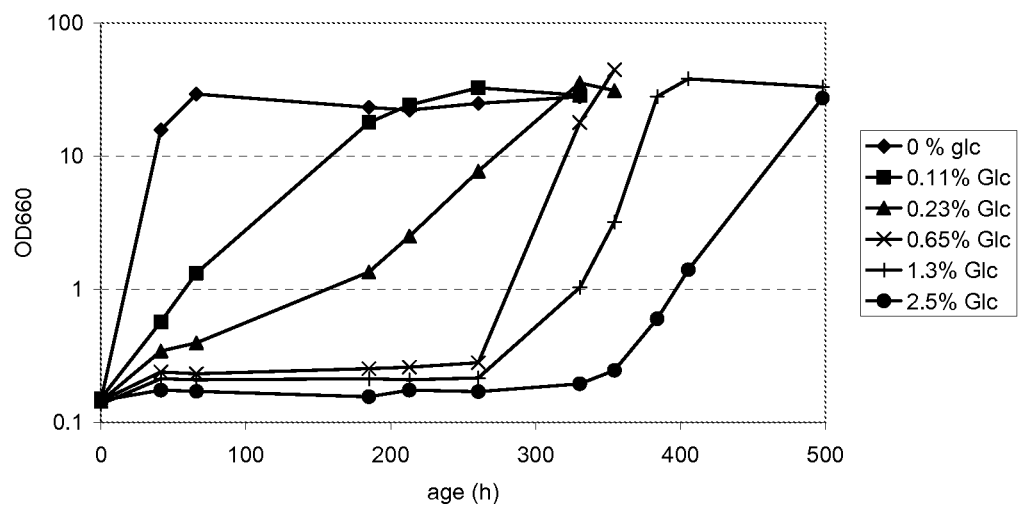
FIG. 3 shows growth profiles determined by measuring optical density at 660 nm ($OD_{660}$) for shake flask cultivations of strain IMK318 in MYurea containing 2% arabinose and various concentrations of glucose (0, 0.11, 0.23, 0.65, 1.3 and 2.5%)

It was confirmed by 450 hours of cultivation in shake flasks on glucose that the hexokinase/glucokinase deletion strain IMK318 (hxk1Δ hxk2Δ glk1Δ) is unable to grow on glucose alone. Therefore the strain was cultivated in YP-EtOH/Glyc and subsequently stored at −80° C. after the addition of glycerol. Subsequently, IMK318 was cultivated in 100 ml MY containing 2% arabinose. After 3 days, at an OD660 of approximately 1, 2 ml of the culture was transferred to 100 ml fresh MY containing 2% arabinose. After approximately 12 days the OD660 of the culture was >5 and samples were stored at −80° C. as glycerol stocks. Strain IMK318 was cultivated at 30° C. for several days in MY-ara. At an OD660 of approximately 5, 2 ml of the culture was transferred to 6 separate shake flasks containing 100 ml MYurea supplemented with 2% arabinose and varying concentrations of glucose: 0, 0.11, 0.23, 0.65, 1.3 and 2.5 (w/v) %. Growth of these 6 parallel cultures was recorded by OD660 measurements (FIG. 3). It was observed that, in the presence of glucose, growth is delayed. An increasing amount of glucose resulted in an increasingly delayed growth on arabinose. Two of these parallel cultures (Line A which started at 0.65 w/v % glucose; Line B which started at 2.5 w/v % glucose) were transferred serially to 100 ml MY supplemented with arabinose and glucose according to the transfer-schemes shown in Table 4.

Figure 4:
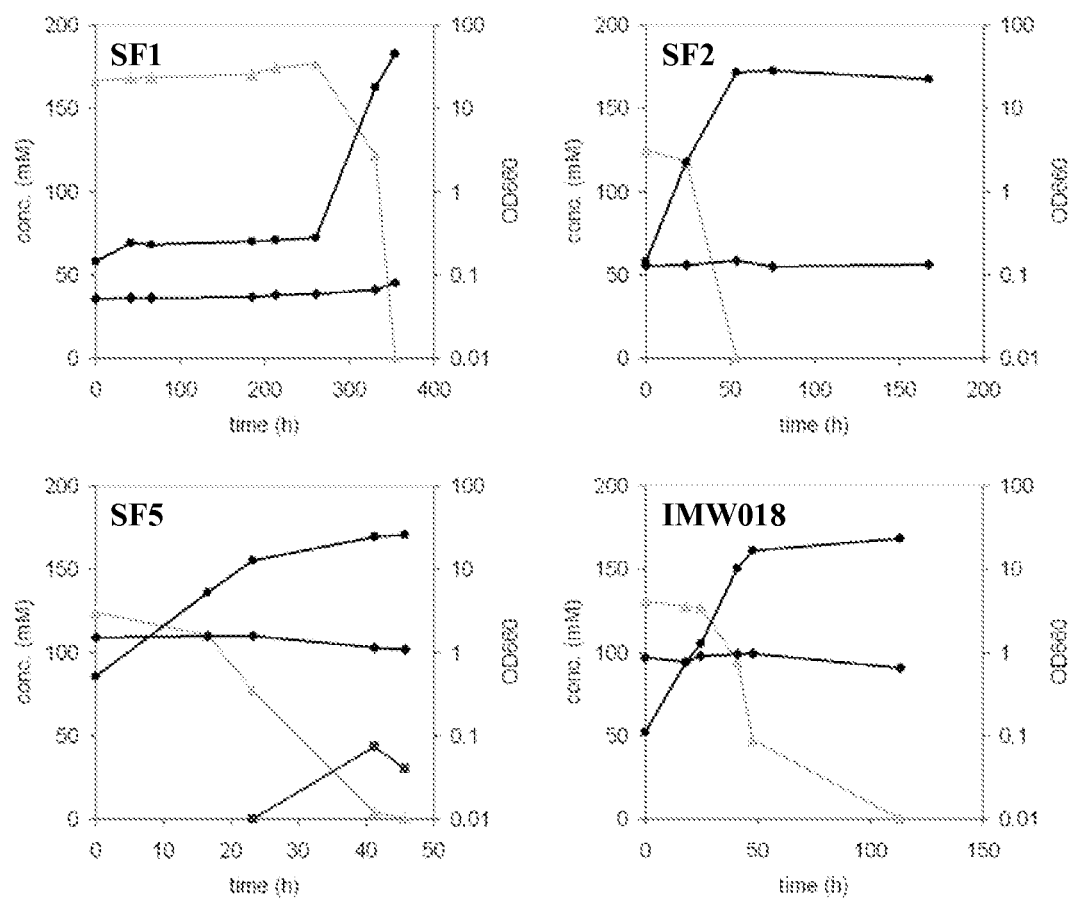
FIG. 4 Glucose (♦), arabinose (▲) and ethanol (■) concentrations and optical density at 660 nm (OD660, ●) during shake flask cultivations of: strain IMK318, serially transferred according to table 3 (Series A: SF1, SF2 and SF5); the single colony isolate selected from this series of shake flasks, IMW018.

In series A, where cultures were transferred to medium with increasing concentrations of glucose (Table 3), arabinose is completely consumed while less than 10% of the glucose was consumed (FIG. 4). From SF7, samples were spread on solid YP-ara supplemented with 100 μg ml$^{-1}$ G418 and incubated at 30° C. until colonies appeared. Separate colonies were transferred to solid YP-ara. Single colony isolates were cultivated in YP-ara and stored at −80° C. Two single colony isolates of this series of serially transferred shake flasks were tested and found qualitatively similar to the mixed culture. One of these isolates was designated as strain IMW018.

Figure 5:
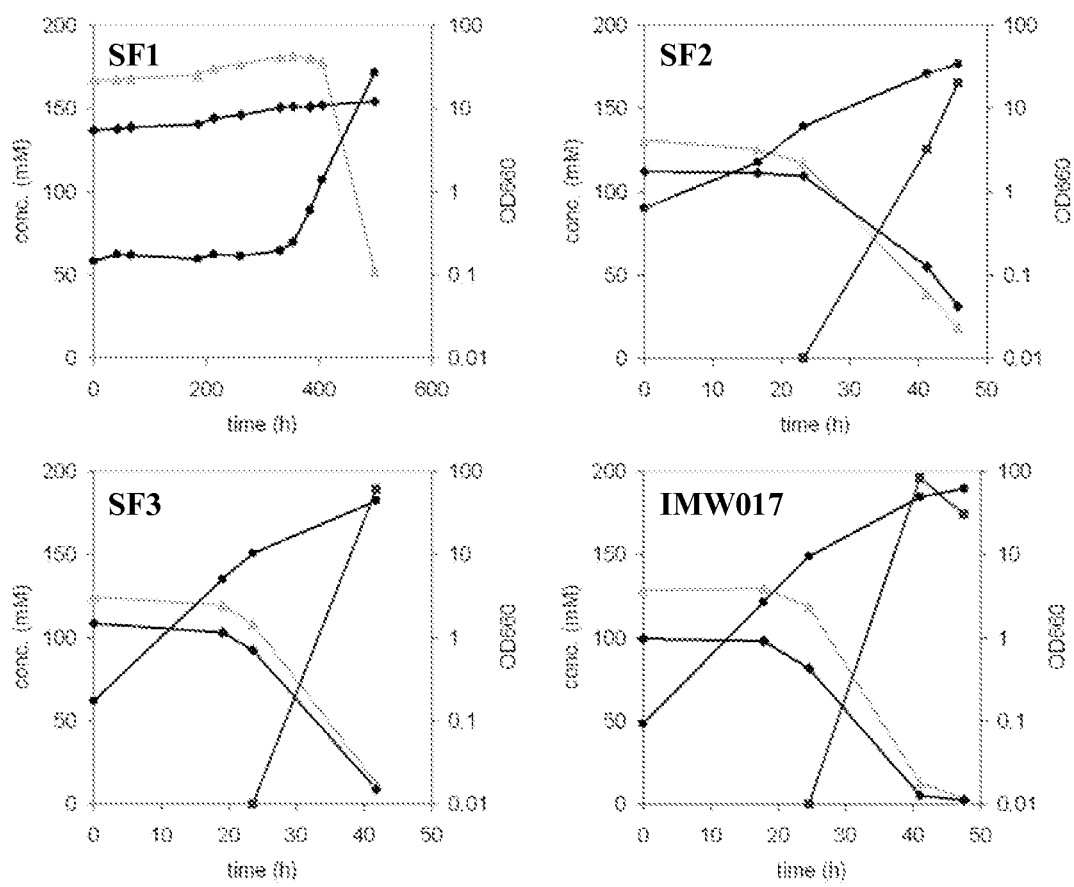
FIG. 5 shows glucose (●), arabinose (▲) and ethanol (■) concentrations and optical density at 660 nm (OD660, ●) during shake flask cultivations of: strain IMK318, serially transferred according to table 3 (Series B: SF1, SF2 and SF3); the single colony isolate selected from this series of shake flasks, IMW017.

In series B (Table 3), shake flask cultures were transferred in MY medium with fixed concentrations of 2% arabinose and 2% glucose (FIG. 5). Surprisingly, co-consumption of arabinose and glucose was observed after the first transfer (SF1→SF2). From SF3, samples were spread on solid YP-ara supplemented with 100 μg ml$^{-1}$ G418 and incubated at 30° C. until colonies appeared. Separate colonies were transferred to solid YP-ara. Single colony isolates were cultivated in YP-ara and stored at −80° C. as glycerol stocks. Two single colony isolates of this series of serially transferred shake flasks were tested and found qualitatively similar to the mixed culture. One of these isolates was designated as strain IMW017.

Glucose and arabinose consumption of both single colony isolate strains IMW017 and IMW018 was tested in shake flask cultures (FIGS. 4 and 5). The single colony isolates exhibited glucose- and arabinose concentration profiles that were similar to the serially transferred shake flask cultures they originate from. Interestingly, the glucose concentration regimes applied in this evolutionary engineering strategy based on the hexokinase/glucokinase deletion strain IMK318 (hxk1Δ hxk2Δ glk1Δ), resulted in two different phenotypes: (i) Glucose-insensitive arabinose consumption by strain IMW018, and (ii) Co-consumption of arabinose and glucose by strain IMW017.

EXAMPLE 3

Anaerobic Co-Fermentation of Arabinose and Glucose

Figure 6:
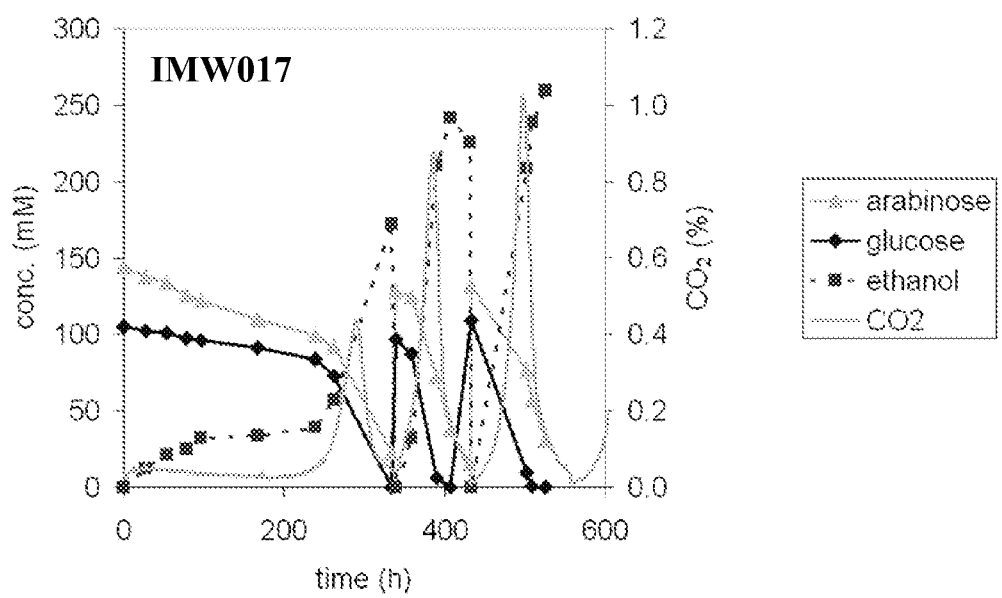
FIG. 6 shows glucose (♦), arabinose (▲) and ethanol (■) concentrations and $CO_2$ percentage in the exhaust gas (solid gray line) during sequential anaerobic cultivations of strain IMW017.

Strain IMW017 was cultivated anaerobically in a mixture of glucose and arabinose, using a sequential batch fermenter set-up. Three consecutive batches in the glucose/arabinose mixture were performed (FIG. 6). In each batch glucose and arabinose were consumed simultaneously and was fermented into ethanol. Deduced from the $CO_2$ production profile, it was observed that the specific growth rate on the glucose/arabinose mixture increased from 0.05 h$^{-1}$ in the first batch to 0.07 h$^{-1}$ in the third batch.

During further consecutive batch fermentations, the growth rate is increased even further. A single colony isolate

TABLE 4

Schematic representation of serially transferred shake flask cultures (SF) of strain IMK318 in MYurea with arabinose (ara) and glucose (glc) concentrations as indicated. Transfer series A and B finally resulted in single colony isolates IMW018 and IMW017 respectively.

| Series | SF1 | SF2 | SF3 | SF4 | SF5 | SF6 | SF7 | Single colony isolate |
|---|---|---|---|---|---|---|---|---|
| A | 2% Ara 0.65 Glc | 2% Ara 1% Glc | 2% Ara 2.5% Glc | 2% Ara 2% Glc | 2% Ara 2% Glc | 2% Ara 2% Glc | 2% Ara 2% Glc | IMW018 |
| B | 2% Ara 2.5% Glc | 2% Ara 2% Glc | 2% Ara 2% Glc | | | | | IMW017 | strain taken from the final batch, exhibits glucose and arabinose co-consumption at an increased specific consumption rates compared to IMW017.

EXAMPLE 4

Hexokinase Activities

The hexokinase activities in cell-extracts of strains DS62504, IMK307, IMK312, IMK318, IMW017 and IMW018 are determined. The hexokinase activity in cell extracts of IMK307 (hxk2Δ) are lower than that of strain DS62504. The hexokinase activity of IMK312 (hxk2Δ hxk1Δ) are lower than that of IMK307, whereas IMK318 (hxk2Δ hxk1Δ glk1Δ) exhibits no/the lowest_hexokinase activity. Hexokinase activities in strain IMW018 are similar to hexokinase activities observed for IMK318, whereas IMW017 has higher hexokinase acitivities than IMK318.

EXAMPLE 5

Identification of an Unknown Hexokinase in IMW017

Based on the measured hexokinase activity in the evolved hxk1 hxk2 glk1 strains, it is expected that another gene with the potential to encode a sugar kinase present in the genome had either become active or changed its substrate specificity to glucose. The gene encoding this activity is identified by genomics analysis. Additional deletion of this gene results in a decrease of the hexokinase activity. This quadruple knock-out strain provides an even stronger platform for evolutionary engineering of arabinose consumption in the presence of glucose.

EXAMPLE 6

Re-introduction of Hexokinase or Glucokinase Activity in IMK318

To restore growth on glucose, either HXK1, HXK2 or GLK1 is re-introduced into IMK318. Activity measurements show that reintroduction of one of these genes in IMK318 results in increased hexo/glucokinase activity. Growth on glucose as the sole carbon source is restored.

EXAMPLE 7

Re-introduction of Hexokinase or Glucokinase Activity in IMW018

Activity measurements show that reintroduction of either HXK1, HXK2 or GLK1 in IMW018 results in increased hexo/glucokinase activity compared to strain IMW018. Growth on glucose as the sole carbon source is restored. Reintroduction of either HXK1, HXK2 or GLK1 results in growth on both glucose and arabinose as sole carbon source. The resulting strain grows in a mixture of glucose and arabinose, exhibiting co-consumption of glucose and arabinose.

EXAMPLE 8

Identification of Underlying Mutations of the Glucose-Insensitive Phenotype of IMW017 and IMW018

It is expected that the glucose-insensitive phenotype of strains IMW017 and IMW018 can be explained by mutations that have been gathered during selective growth of strain IMK318 in medium containing glucose and arabinose. To identify these mutations, the genomes of strains IMK318, IMW017 and IMW018 are sequenced. By comparing the genome sequences of IMW017 vs IMK318 and IMW018 vs IMK318 genomic modifications, like e.g. single nucleotide polymorphisms, are identified. Introduction of these single nucleotide polymorphisms in DS62504 results in phenotypes of which growth on arabinose is insensitive to glucose.

EXAMPLE 9

Deletion of GAL1

Another approach to determine the protein(s) responsible for the remaining hexokinase activity is to delete genes that potentially encode hexokinase activity in the hxk1 hxk2 glk1 strain. To this aim, the GAL1 gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

EXAMPLE 10

Deletion of YDR516c

Another approach to determine the protein(s) responsible for the remaining hexokinase activity is to delete genes that potentially encode hexokinase activity in the hxk1 hxk2 glk1 strain. To this aim, the YDR516c gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

EXAMPLE 11

Deletion of YLR446w

Another approach to determine the protein(s) responsible for the remaining hexokinase activity is to delete genes that potentially encode hexokinase activity in the hxk1 hxk2 glk1 strain. To this aim, the YLR446w gene is deleted in the hxk1 hxk2 glk1 strain. The resulting strain shows lower hexokinase activity than the parental hxk1 hxk2 glk1 strain or shows a decreased ability to grow on glucose as the sole carbon source compared to the parental hxk1 hxk2 glk1 strain. This quadruple knock-out strain provides an even stronger platform for evolutionary engineering of arabinose consumption in the presence of glucose.

EXAMPLE 12

Anaerobic Co-Fermentation of Arabinose and Glucose

To improve co-consumption of glucose and arabinose of strain IMW017, strain IMW017 was cultivated anaerobically in MY supplied with a mixture of 20 g/liter glucose and 20 g/liter arabinose, using a sequential batch fermenter set-up.

Figure 7:
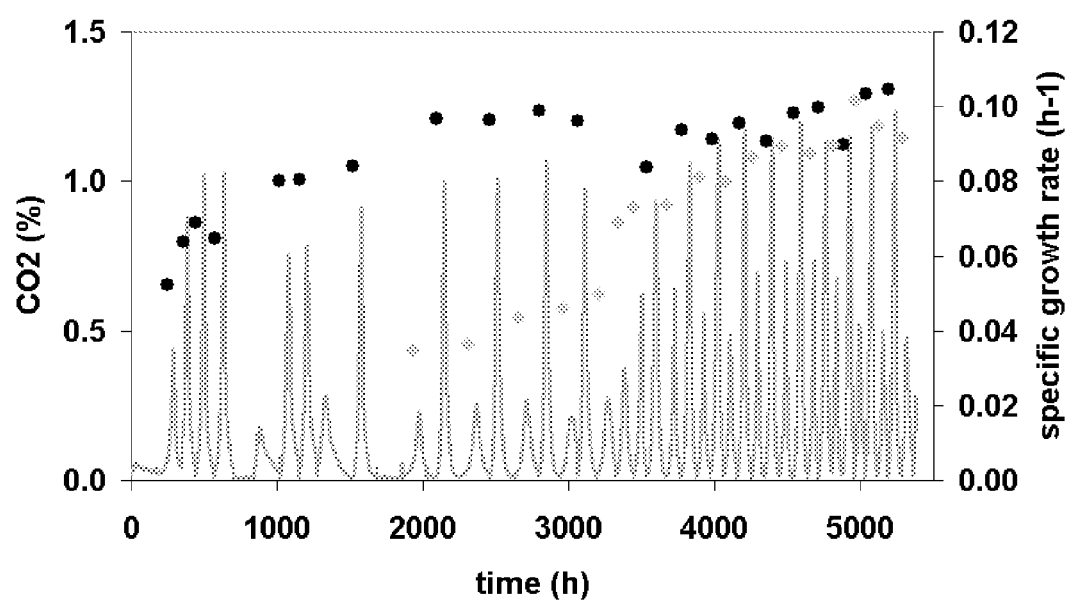
FIG. 7 shows $CO_2$ percentage in the exhaust gas (solid gray line) and growth rates during sequential anaerobic cultivations of strain IMW017. The specific growth rates are derived from the $CO_2$ production profile during the batch cultivations on either the mixture of glucose and arabinose (●) or arabinose only (♦).
Figure 8:
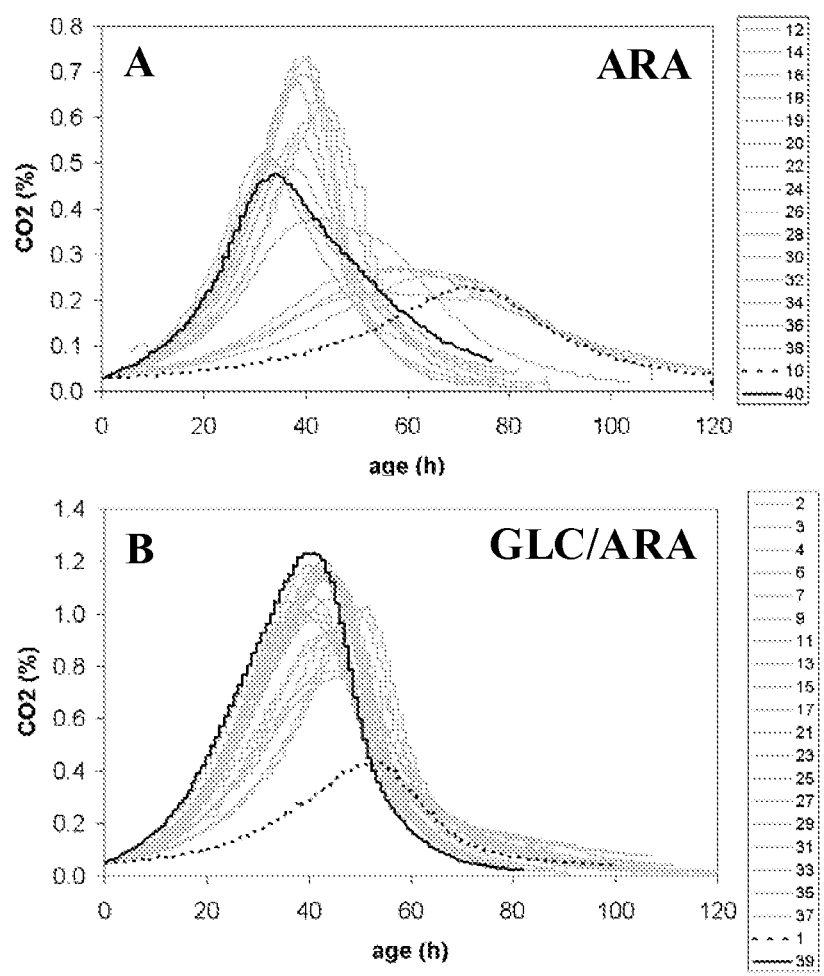
FIG. 8 shows the $CO_2$ production profiles of the individual batches in medium supplied with arabinose (A) and a mixture of glucose and arabinose (B) during anaerobic sequential batch cultivation of strain IMW017. The $CO_2$ production profiles are aligned assuming an equal initial CO2 production level. The numbers in the legend indicate the consecutive batch numbers.
Figure 9:
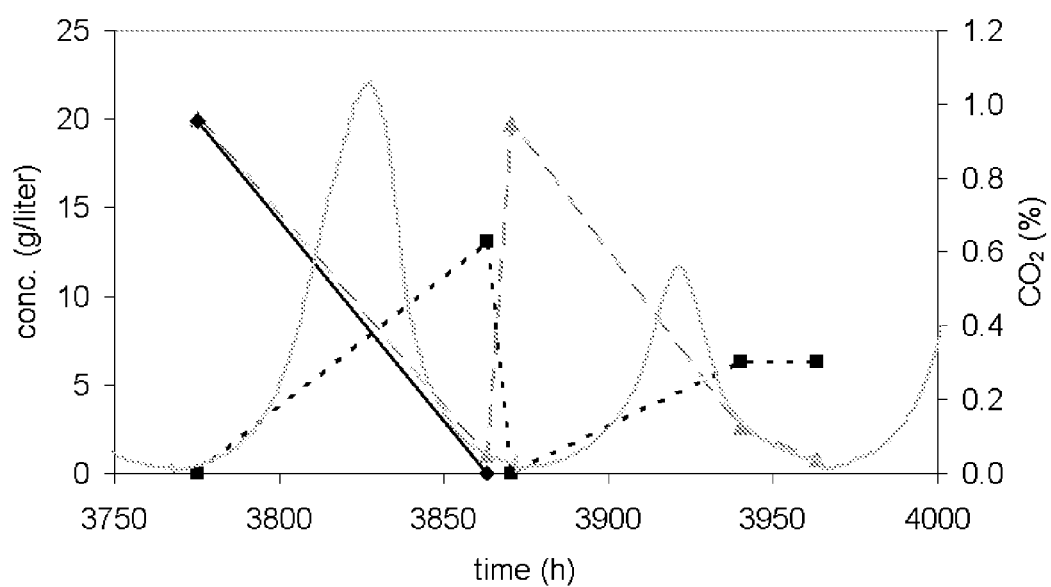
FIG. 9 shows glucose (♦), arabinose (▲) and ethanol (■) concentrations and $CO_2$ percentage in the exhaust gas (solid gray line) during batches 24 and 25 of the sequential anaerobic batch cultivation of strain IMW017.

Initially, four consecutive batches in the glucose/arabinose mixture were performed. In each batch glucose and arabinose were consumed simultaneously and was fermented into ethanol (FIG. 6, example 3). Deduced from the $CO_2$ production profile, it was observed that the specific growth rate on the glucose/arabinose mixture increased from 0.05 $h^{-1}$ in the first batch to 0.06 $h^{-1}$ in the fourth batch. After the fourth batch, consecutive batch cultivations were performed in either mixtures of glucose and arabinose (batch nrs 6, 7, 9, 11, 13, 15, 17, 21, 23, 25, 27, 29, 31, 33, 35, 37 and 39) or arabinose only (batch nrs 5, 8, 10, 12, 14, 16, 18, 19, 20, 22, 24, 26, 28, 30, 32, 34, 36, 38 and 40). After 19 and 21 batches in MY-arabinose and MY-glucose/arabinose respectively, the anaerobic growth rate increased to 0.09 $h^{-1}$ on arabinose as sole carbon source and 0.10 $h^{-1}$ on the glucose/arabinose mixture (FIG. 7). Comparison of the $CO_2$ production profiles of the individual batch cultivations shows that the repeated batch regime has resulted in a decreased fermentation time for either arabinose only or the glucose/arabinose mixture from approximately 120 hours to approximately 80 hours, assuming an equal initial inoculum size for each batch (FIG. 8). The single peak of $CO_2$ production that was observed for the batch cultivations in the glucose/arabinose mixture indicates that glucose and arabinose are consumed simultaneously, rather than sequentially (FIGS. 8 and 9).

EXAMPLE 13

Hexokinase Activities

Figure 10:
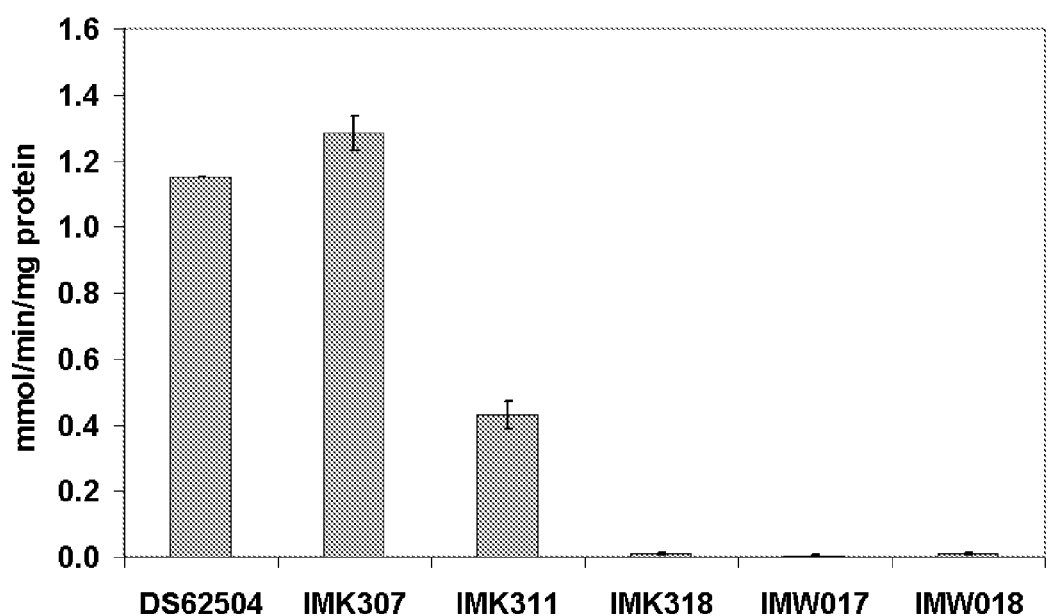
FIG. 10 shows the hexokinase enzyme activity of strains DS62504, IMK307, IMK311, IMK318, IMW017 and IMW018.

The hexokinase activities of strains DS62504, IMK307, IMK312, IMK318, IMW017 and IMW018 were determined in cell-extracts of shake flask cultures grown in YP supplied with arabinose. The hexokinase reaction mixture consisted of 50 mM imidazole-HCl, pH 7.6, 1 mM $NADP^+$, 10 mM $MgCl_2$, 2 U glucose-6-phosphate dehydrogenase, 10 mm D-glucose and cell extract. The reaction was started by the addition of 1 mM ATP and the formation of NADPH was determined by measuring the absorbance of the reaction mixture at 340 nm. The hexokinase activity in cell extracts of strains DS62504 and IMK307 (hxk2Δ) were 1.2 and 1.3 $\mu mol.min^{-1}.mg^{-1}$ protein respectively (FIG. 10). The hexokinase activity of 0.4 $\mu mol.min^{-1}.mg^{-1}$ protein in cell extracts of IMK312 (hxk2Δ hxk1Δ) was lower than that of IMK307. Strains IMK318 and IMW018 (hxk2Δ hxk1Δ glk1Δ) exhibited a hexokinase activity of less than 0.02 $\mu mol.min^{-1}.mg^{-1}$ protein. Strain IMW017, being able to consume glucose despite the triple hxk2 hxk1 and glk1 deletions, was expected to have a higher hexokinase activity compared to strain IMK318 and IMW018, both not being able to consume glucose. Hexokinase activity for strain IMW017 was also less than 0.02 $\mu mol.min^{-1}.mg^{-1}$ protein under the assay conditions.

EXAMPLE 14

Identification of GAL1 as a Hexokinase in IMW017

Based on growth experiments of the evolved hxk1Δ hxk2Δ glk1Δ strain IMW017 on mixtures of glucose and arabinose, it was expected that another gene with the potential to encode a sugar kinase present in the genome had either become active or changed its substrate specificity to glucose. To investigate whether the unknown hexokinase activity was encoded by GAL1, the GAL1 gene was deleted in IMW017. After removal of the KanMX cassette from the glk1 locus using pSH65 (see example 1), GAL1 deletion was achieved by integration of a G418 resistance cassette that was amplified by PCR using oligonucleotides GAL1-DisA and GAL1-DisB (Table 5). Transformed cells were selected on YP-agar containing 100 $\mu$g $ml^-$ G418 (InvivoGen, San Diego, USA) and 1.5% (w/v) ethanol and 1.5% (w/v) glycerol as carbon source. Correct integration of the KanMX cassette was verified by PCR on single colonies using combinations of the diagnostic oligonucleotides GAL1-FW2/KanA and GAL1-RV2/KanB. (Table 4). Deletion of GAL1 in the resulting strain IMW023 was confirmed by the inablity to grown on galactose as sole carbon source.

Figure 11:
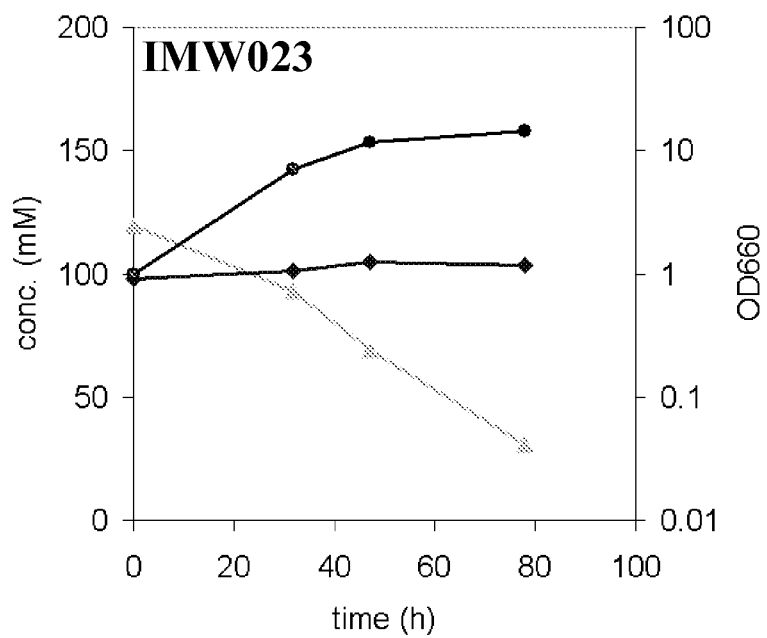
FIG. 11 shows the OD660 (●), arabinose concentration (▲), and glucose concentration (♦) during a shake flask cultivation of strain IMW023 in MY medium supplied with 2% of glucose and 2% of arabinose.

Interestingely, IMW023 was not able to use glucose as carbon source, indicating that GAL1 was responsible for the unknown hexokinase activity in its parental hxk1Δ hxk2Δ glk1Δ strain IMW017. During a shake flask cultivation in a mixture of glucose and arabinose, IMW023 did not consume glucose while arabinose was consumed (FIG. 11).

TABLE 5

Oligonucleotides used in this study for the deletion of GAL1 and related diagnostic purposes. A KanMX gene deletion cassette was obtained by PCR by using combinations of the GAL1-DisA and GAL1-DisB oligonucleotides. GAL1 was disrupted by homologues recombination between the target gene and the KanMX gene deletion cassette. Recombination sites are indicated by the underlined regions in the oligonucleotides. Deletion or disruption was confirmed by PCR using diagnostic primers KanA and KanB combined with the FW and the RV diagnostic primers corresponding with the target gene.

| | |
|---|---|
| GAL 1-DisA | TAATATACCTCTATACTTTAACGTCAAGGAGAAAAAACTATAATGCAGCTGAAGCTTCGTACGC |
| GAL 1-DisB | AATGAGAAGTTGTTCTGAACAAAGTAAAAAAAGAAGTATACTTACATAGGCCACTAGTGGATCTG |
| Kan A | CGCACGTCAAGACTGTCAAG |
| Kan B | TCGTATGTGAATGCTGGTCG |
| GAL 1-FW2 | ATGGCATTATACTCCTGCTAGAAAG |
| GAL 1-RV2 | AAAGGATGGCAGAGCATGTTATCG |

EXAMPLE 15

Towards anaerobic fermentation of arabinose in the presence of glucose Since it was found that GAL1p in IMW017 also exhibits hexokinase activity, the hxk1Δ hxk2Δ glk1Δ gal1Δ strain IMW023 provides a more solid platform to improve arabinose consumption in the presence of glucose by evolutionary engineering, without glucose being consumed.

Figure 12:
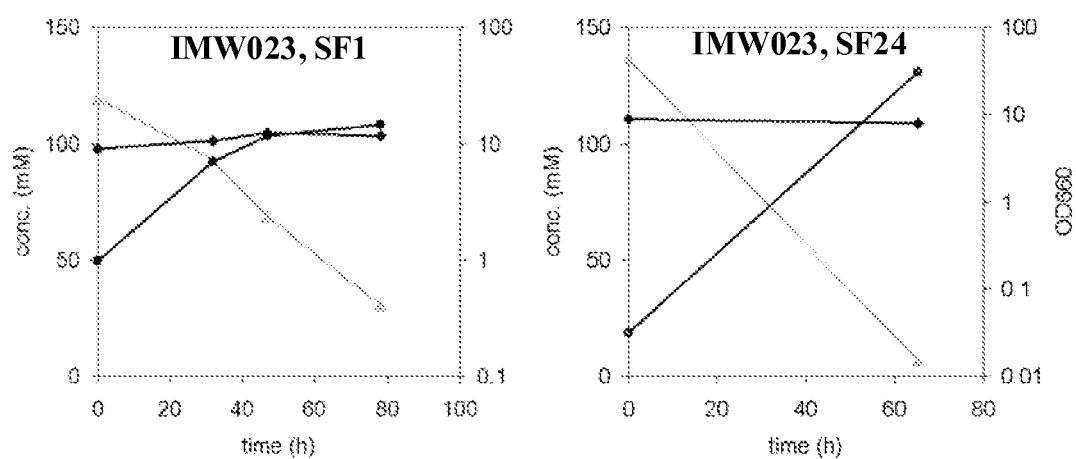
FIG. 12 shows the OD660 (●), arabinose concentration (▲), and glucose concentration (♦) during the first (SF1) and the $24^{th}$ (SF24) shake flask cultivation of a serially transferred culture of strain IMW023 in MY medium supplied with 2% of glucose and 2% of arabinose.
Figure 13:
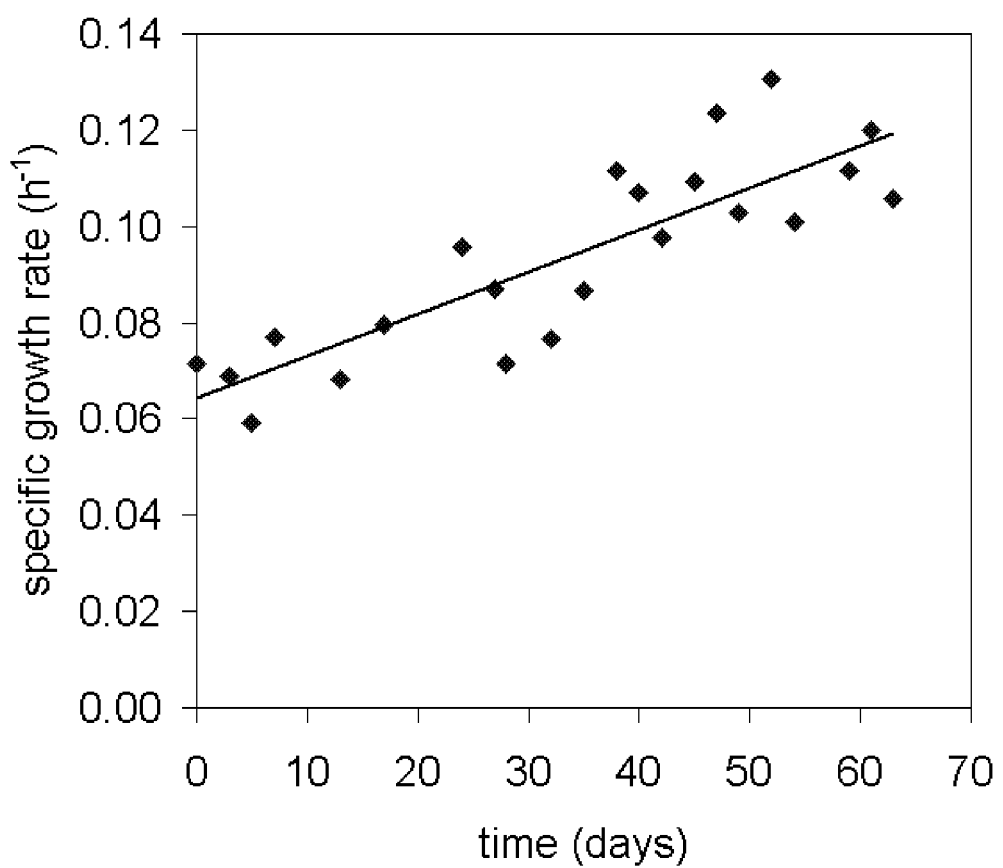
FIG. 13 shows the estimated specific growth rates determined in the individual shake flask cultivations of a serially transferred culture of strain IMW023 in MY medium supplied with 2% of glucose and 2% of arabinose.

To select for improved arabinose consumption in the presence of glucose in the medium, strain IMW023 was cultivated in shake flask cultures by serial transfer in MY medium supplied with 2% arabinose and 2% glucose. Growth was monitored by OD660 measurements and specific growth rates were estimated from either 2 or 3 OD660 measurements per culture. Glucose and arabinose concentrations were determined by HPLC analysis. After 24 serial transfers on the arabinose/glucose mixtures in 63 days, the transferred culture of strain IMW023 was still able to grow on arabinose in the presence of 2% glucose, without consuming glucose (FIG. 12). The specific growth rate on arabinose increased from approximately 0.06 $h^{-1}$ to approximately 0.11 $h^{-1}$ (FIG. 13).

Figure 14:
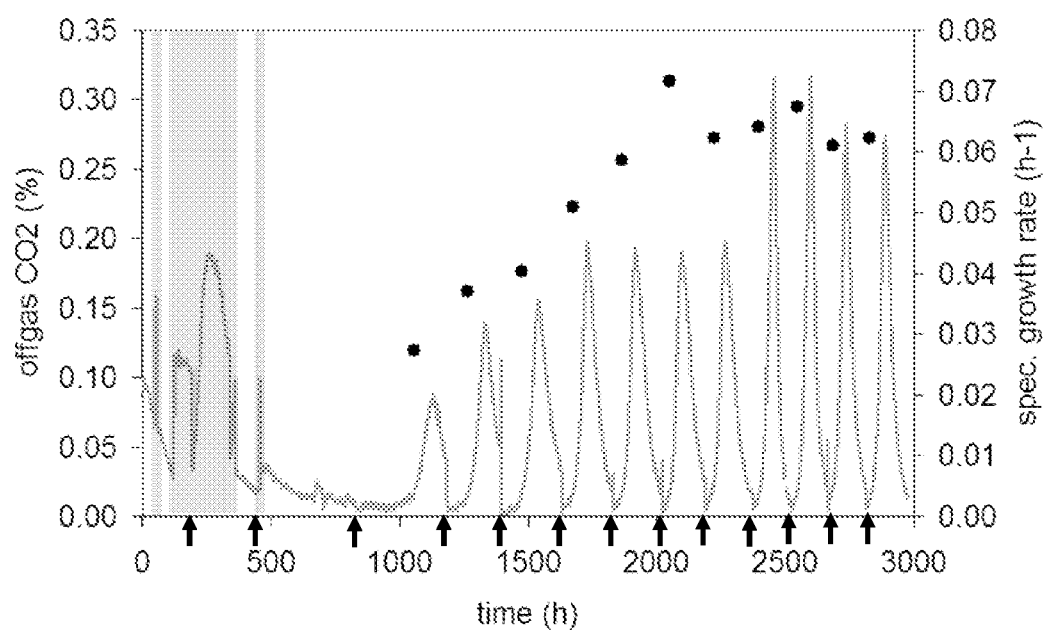
FIG. 14 shows the $CO_2$ percentage in the exhaust gas (solid gray line) and the specific growth rates during sequential anaerobic batch cultivations of strain IMW023 in MY medium supplied with 20 g/liter of glucose and 20 g/liter of arabinose, and the specific growth rates of the individual batch cultivations (●). The grey shades indicate where air was supplied in stead of nitrogen gas. The arrows indicate the start of a new consecutive batch.
Figure 15:
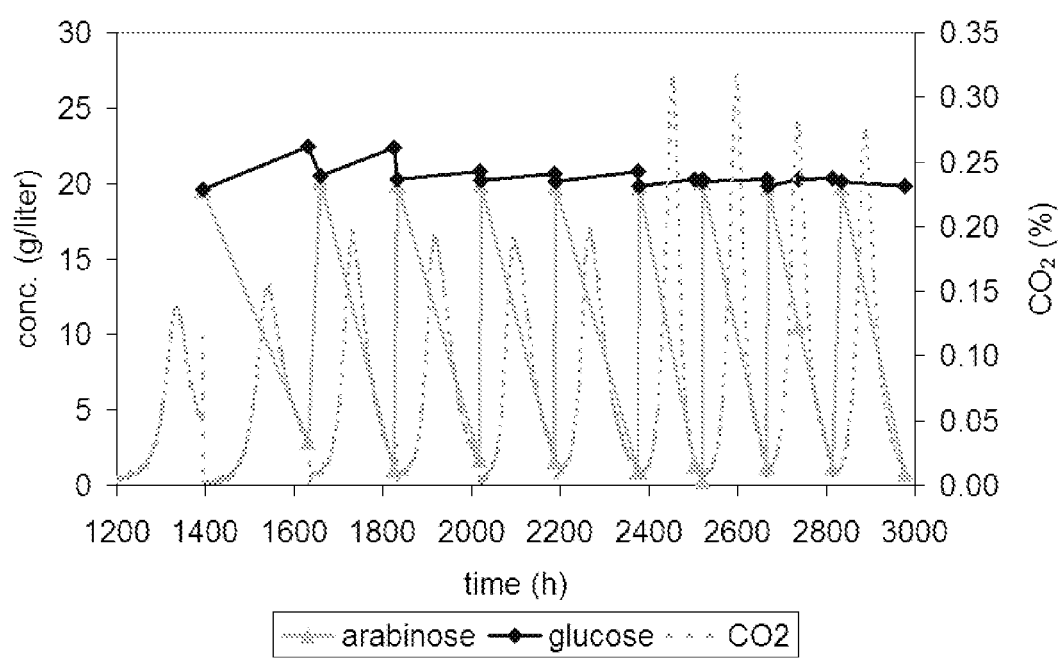
FIG. 15 shows the $CO_2$ percentage in the exhaust gas (solid gray line), the arabinose concentration (▲) and glucose concentration (♦) during sequential anaerobic batch cultivations of strain IMW023 in MY medium supplied with 20 g/liter of glucose and 20 g/liter of arabinose.
Figure 16:
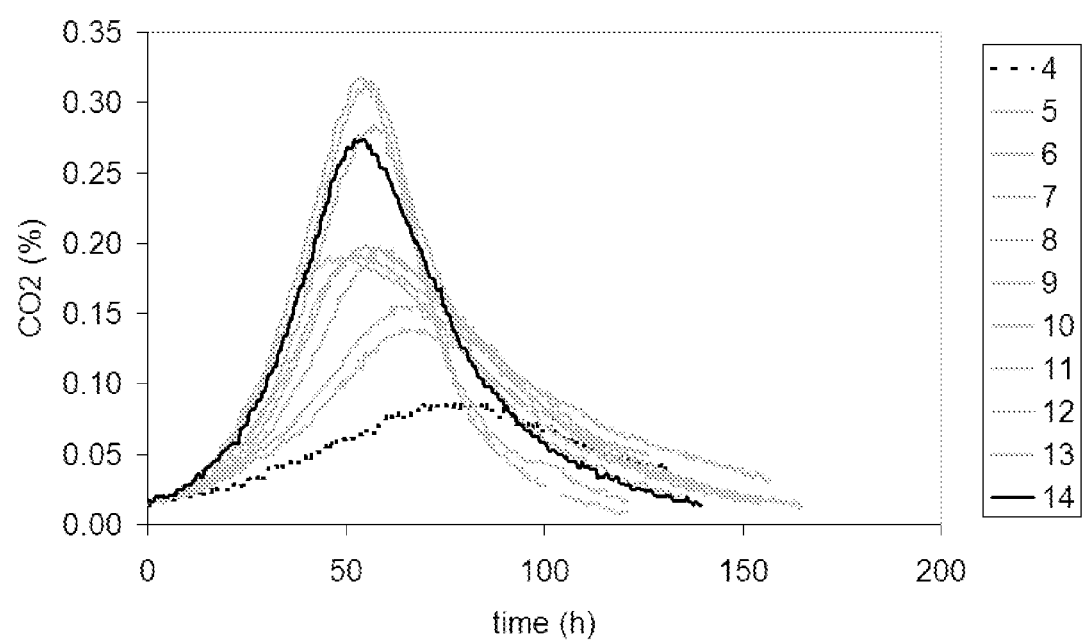
FIG. 16 shows the aligned $CO_2$ production profiles of the individual batches during anaerobic sequential batch cultivation of strain IMW023 in MY medium supplied with 20 g/liter of glucose and 20 g/liter of arabinose. The $CO_2$ production profiles are aligned assuming an equal initial $CO_2$ production level. The numbers in the legend indicate the consecutive batch numbers.

To select for cells that are able to consume arabinose in the presence of glucose under anaerobic conditions, and to further improve the arabinose consumption in the presence of glucose, the sequential transfer of strain IMW023 in MY medium supplied with 2% arabinose and 2% glucose was continued in an anaerobic sequential batch fermentation setup. For this, the final shake flask culture of the serially transferred culture (SF24) of strain IMW023 was used as inoculum. In the first 1000 hours of cultivation, increased $CO_2$ production was only observed when air was supplied to the headspace of the fermenter in stead of nitrogen gas (FIG. 14). After approximately 1000 hours of cultivation during the fourth batch, an increase of the $CO_2$ concentrations in the exhaust gas was observed. Deduced from the $CO_2$ production profile, this first batch of anaerobic growth exhibited a specific growth rate of approximately 0.03 $h^{-1}$. After another ten transfers, the specific growth rate increased to approximately 0.06 $h^{-1}$ (FIG. 14). During the sequentially transferred batch cultures arabinose was consumed while glucose was not (FIG. 15). The $CO_2$ production profiles of the individual batch cultivations show that the rate of $CO_2$ production, and thus the arabinose consumption rate, has increased during the sequential transfers, which has resulted in a decrease of the fermentation time needed to completely consume arabinose (FIG. 16).

A single colony isolate taken from the final batch, designated as strain IMW058, exhibits increased arabinose consumption rates in the presence of glucose compared to IMW023.

EXAMPLE 16

Re-Introduction of Hexokinase or Glucokinase Activity in IMW018

Reintroduction of either HXK1, HXK2 or GLK1 in strain IMW018 was performed to restore growth on glucose. For this, HXK2, HXK1 and GLK1 were amplified by PCR using oligonucleotide combinations HXK2FW/HXK2RV, HXK1FW/HXK1RV and GLK1FW/GLK1RV, using genomic DNA of S. cerevisiae CENPK113-7D as a template. After purification of the PCR products (GenElute PCR Cleanup Kit, Sigma, Steinheim, Germany), an overnight culture of IMW018 was transformed (Gietz and Woods 2002) with the PCR products. Transformed cells were selected for growth on glucose on MY-agar containing 2% of glucose. Correct integration of HXK2, HXK1 and GLK1 by homologous recombination at their original locus was verified by PCR on single colonies using the diagnostic primer pairs (TABLE 6).

Figure 17:
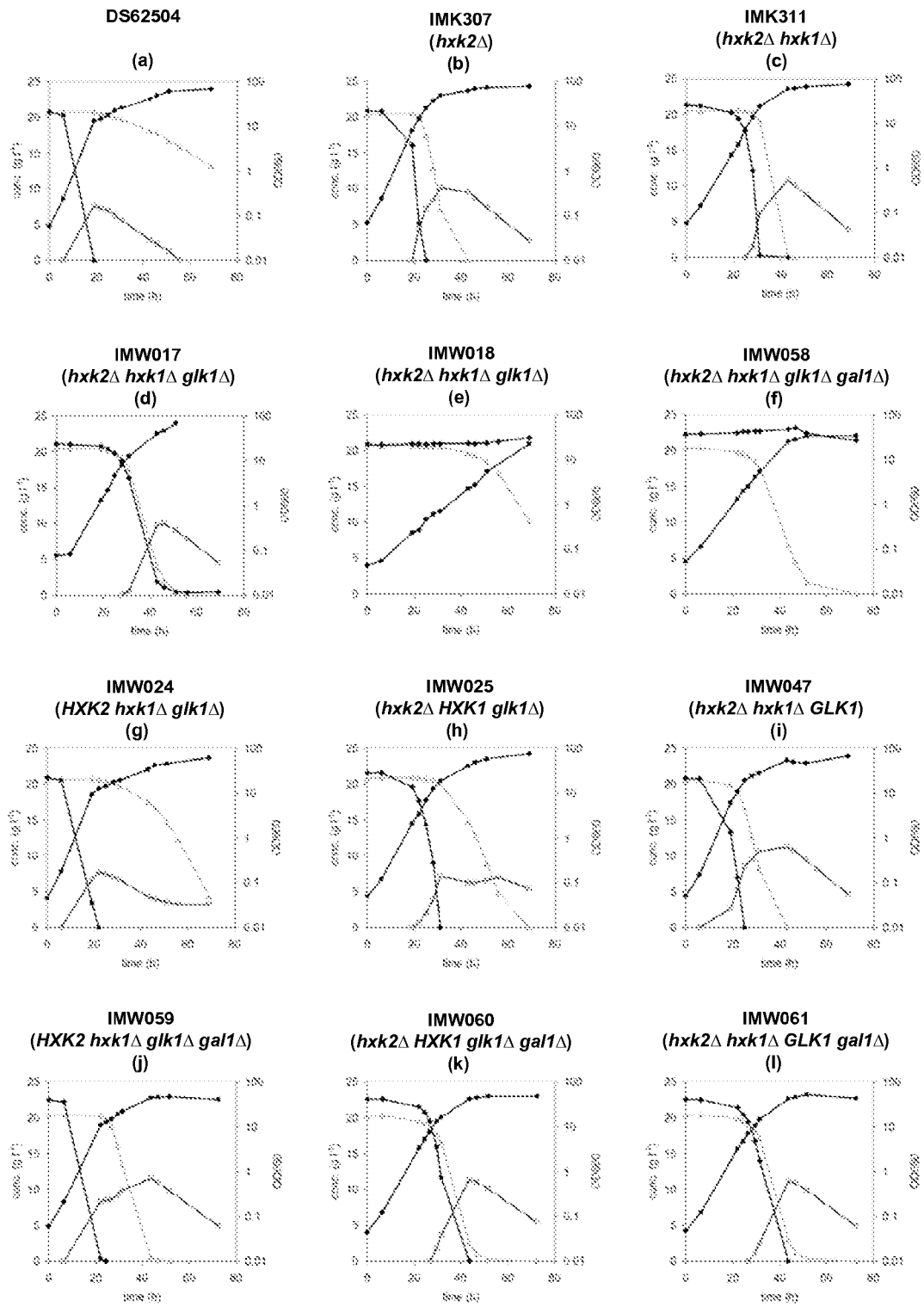
FIG. 17 shows glucose (♦), arabinose (▲) and ethanol (□) concentrations and optical density at 660 nm (OD660, ●) during shake flask cultivations of strains DS62504 (FIG. 17(a)), IMK307 (FIG. 17 (b), IMK311 (FIG. 17 (c)), IMW017 (FIG. 17 (d)), IMW018 (FIG. 17 (e)) and IMW058 (FIG. 17 (f)), IMW024 (FIG. 17 (g)), IMW025 (FIG. 17 (h)), IMW047 (FIG. 17 (i)), IMW059 (FIG. 17 (j)), IMW060 (FIG. 17 (k)), IMW061 (l)).
Figure 18:
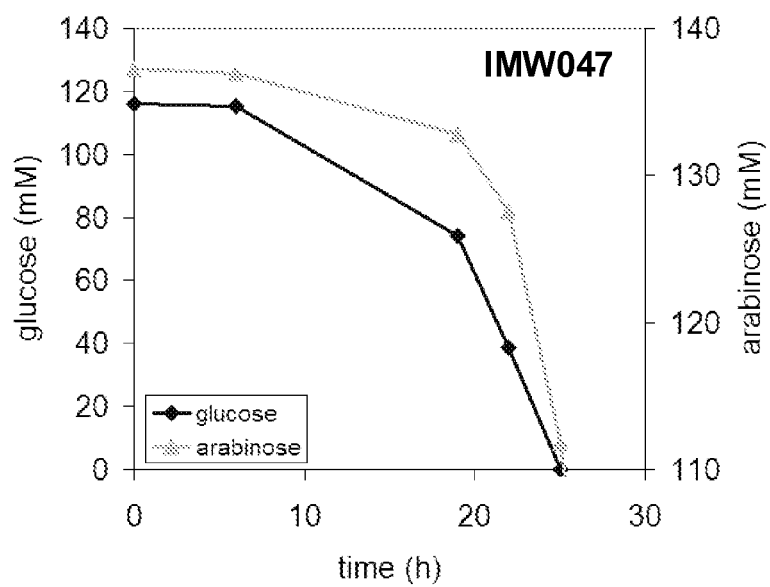
FIG. 18 shows glucose (♦) and arabinose (▲) concentrations during a shake flask cultivation of strain IMW047.

The resulting strains IMW024 (HXK2), IMW025 (HXK1) and IMW047 (GLK1) were cultivated with an initial OD660 of 0.05±0.01 in shake flasks at 30° C. in MY-urea medium (pH 4.7) supplied with 2% glucose and 2% arabinose, using precultures grown on glucose. For comparison, strains DS62504, IMK307 and IMK311 were cultivated under the same conditions. Growth and sugar consumption was monitored for 69 hours. Strains IMW024, IMW025 and IMW047 were all able to utilize both glucose and arabinose (FIG. 17). Re-introduction of GLK1 in IMW018 (IMW047) resulted in fast glucose and arabinose consumption. Arabinose and glucose were completed within 43 hours of cultivation, which is similar to what was observed for IMK307 (hxk2Δ) and IMK311 (hxk1Δ hxk2Δ). The arabinose consumption observed for IMW024 (HXK2) and IMW025 (HXK1) was both slower than for IMK307 and IMK311, however faster than for the parental strain DS62504 without any HXK/GLK deletions (FIG. 17 (a)). Co-consumption of arabinose and glucose was only observed for strain IMW047 (FIG. 18). Before glucose was depleted at 22 hours, approximately 7% of the arabinose was consumed. At 25 hours, when glucose was completely consumed, 19% of the arabinose was utilized.

TABLE 6

Oligonucleotides used in this study for the amplification of HXK2, HXK1 and GLK1. Integration of these PCR products at their original locus was verified by PCR using diagnostic primers of which their annealing sites are located on the insert and in the flanking regions of the integration site.

| | DNA sequence |
|---|---|
| Amplification primer pair | |
| HXK2-FW/ | TTCGCCACTGTCTTATCTAC |
| HXK2-RV | CCGTTCGTTCCAGAATTATC |
| HXK1-FW/ | CCTTAGGACCGTTGAGAGGAATAG |
| HXK1-RV | TCCCGGAGAACAAAGTAAGTTG |
| GLK1-FW/ | AAAAACGGGAAATAACAATAACGAC |
| GLK1-RV | TGCGATCTTATTAGTGTGTGACATT |
| Diagnostic primer pair | |
| HXK2-FW2/ | GATTGCGAGATCCACGAAATTACC |
| HXK2-RV2 | AATCACCGGATTCCTTACCAGTTG |
| HXK2-FW3/ | GAAATTCACGGGATTTATTCGTGAC |
| HXK2-RV3 | TTTCCATGTTTCTAAGCGTAGTGAG |
| HXK1-FW2/ | CCCGTTTGTTGGAAGATAGC |
| HXK1-RV2 | CACATCAGCCATGGAACC |
| HXK1-FW3/ | GCAGGTGCTGCTGTTATTG |
| HXK1-RV3 | CCGAGCTATCCTACGACTTTC |
| GLK1-FW4/ | GCCCGACAGGGTAACATATTATC |
| GLK1-RV4 | CCGGAATCATAGGAAGACCTTTG |
| GLK1-FW5/ | AGAGGAAGGTGCACTTGAAGATTG |
| GLK1-RV5 | ATAAGATGGAATTGGCCGGTCTTG |

EXAMPLE 17

Re-Introduction of Hexokinase or Glucokinase Activity in IMW058

Reintroduction of either HXK1, HXK2 or GLK1 in strain IMW058 was performed to restore growth on glucose. For this, HXK2, HXK1 and GLK1 were amplified by PCR using oligonucleotide combinations HXK2FW/HXK2RV, HXK1FW/HXK1RV and GLK1FW/GLK1RV, using genomic DNA of S. cerevisiae CENPK113-7D as a template.

After purification of the PCR products (GenElute PCR Cleanup Kit, Sigma, Steinheim, Germany), an overnight culture of IMW058 was transformed (Gietz and Woods 2002) with the PCR products. Transformed cells were selected for growth on glucose on MY-agar containing 2% of glucose. Correct integration of HXK2, HXK1 and GLK1 by homologous recombination at their original locus was verified by PCR on single colonies using diagnostic oligonucleotides (TABLE 5).

The resulting strains IMW059 (HXK2), IMW060 (HXK1) and IMW061 (GLK1) were cultivated with an initial OD660 of 0.05±0.01 in shake flasks at 30° C. in MY-urea medium (pH 4.7) supplied with 2% glucose and 2% arabinose, using precultures grown on glucose. Growth and sugar consumption was monitored for 72 hours. Strains IMW059, IMW060 and IMW061 were all able to utilize both glucose and arabinose (FIG. 17). Re-introduction of HXK2 in IMW058 resulted in fast sequential consumption of arabinose and glucose. While the reference strain DS62504 did not completely consume the arabinose within 69 hours (FIG. 17 (a)), strain IMW059 consumed more than 99% of the arabinose within approximately 46 hours (FIG. 17 (j)).

For strains IMW060 (HXK1) and IMW061 (GLK1) simultaneous consumption of glucose and arabinose was observed (FIGS. 17 (k) and (l)). In the first 22 hours of cultivation, approximately 18% of the arabinose was co-consumed together with approximately 48% of the glucose. Within 50 hours of cultivation, 99% of the arabinose was consumed.

EXAMPLE 18

Comparative Whole Genome Sequencing of Strains IMK318, IMW017 and IMW018

Whole genome DNA sequencing for strains IMK318, IMW017 and IMW018 was performed using Illumina GAllx technology (75 bp reads, paired-ends). Sequence reads were aligned to a reference genome sequence of S. cerevisiae CEN.PK 113-7D using CLC Genomics Workbench version 4.5. SNP analysis was performed using CLC Genomics Workbench version 4.5.

In total, SNP analysis yielded four mutations in coding regions resulting in an aminoacid change when IMK318, IMW017 and IMW018 were compared to the reference sequence of CEN.PK 113-7D.

One mutation, resulting in a Asp376Val amino acid change in GAL1 which encodes galactokinase. The mutation was found in IMK318, IMW017 and IMW018 when compared to the reference sequence (FIG. 19).

Surprisingly, only two unique mutations for IMW017 were found. One of them, a Tyr274Phe mutation in GAL1, is located in the galactose binding site of galactokinase, which was described by Thoden et al. (2005). Combined with the observation that deletion of GAL1 in IMW017 eliminates growth on glucose, it seems likely that this mutation was responsible for the hexokinase activity of GAL1 that allowed glucose consumption in IMW017. A second mutation was found in transmembrane motif 5 of GAL2 (Thr219Asn), which encodes the galactose permease in S. cerevisiae. GAL2p is known to be able to transport arabinose (Kou et. al 1970; Becker et al. 2003). A mutation in GAL2 that increases the affinity for arabinose or decreases the affinity for glucose, will result in improved arabinose consumption in the presence of glucose.

Surprisingly, only 1 unique mutation was found in the coding regions of IMW018. This mutation was located in transmembrane motif 8 of GAL2 (Asn376Ser), which encodes the galactose permease in S. cerevisiae. GAL2p is known to be able to transport arabinose (Kou et. al 1970; Becker et al. 2003). A mutation in GAL2 that increases the affinity for arabinose or decreases the affinity for glucose, will result in improved arabinose consumption in the presence of glucose.

EXAMPLE 19

Fast Anaerobic Fermentation of Glucose and Arabinose by IMW059

Strain IMW059 was cultivated anaerobically in MY medium with 20 g l$^{-1}$ glucose and 20 g l$^{-1}$ arabinose. Sugar consumption was monitored by HPLC measurements. Growth of the yeast was determined by dry weight measurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Figure 21:
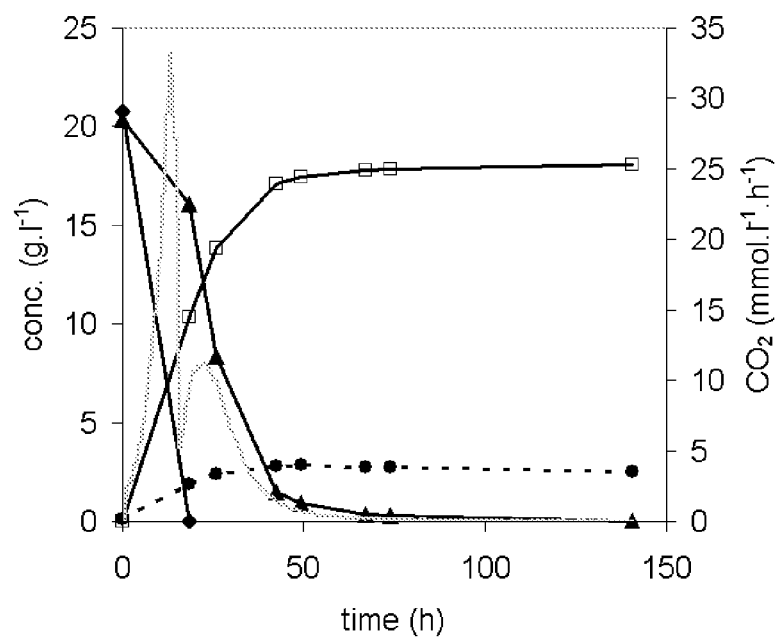
FIG. 21 shows glucose (♦), arabinose (▲), ethanol (□) concentrations, biomass dry weights (●) and CO2 production (solid grey line) during anaerobic cultivation of strain IMW059 in MY medium supplied with 20 g $l^{-1}$ glucose and 20 g $l^{-1}$ arabinose.
Figure 24:
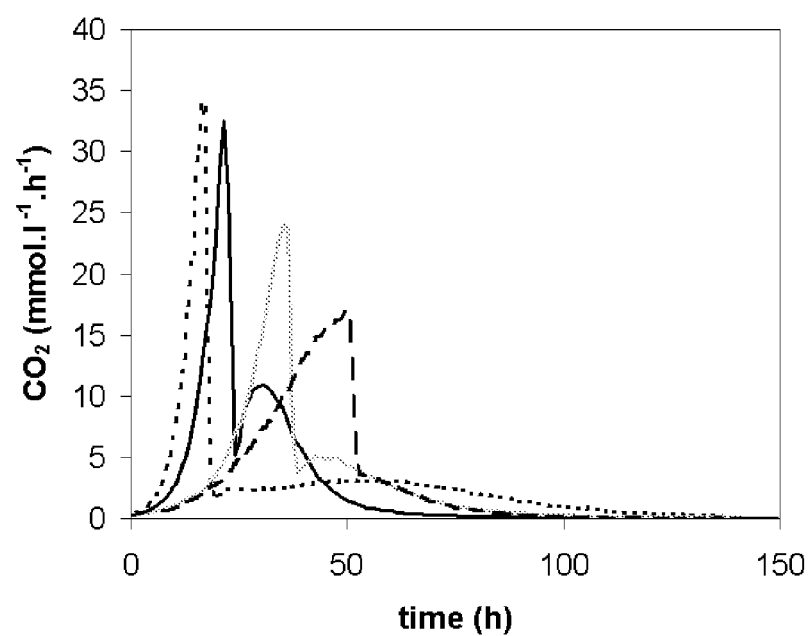
FIG. 24 shows the CO2 production profiles of strains DS62504 (dotted black line), IMW059 (solid black line), IMW060 (solid black line) and IMW061(striped black line) during anaerobic cultivation in a mixture of 20 g $l^{-1}$ glucose and 20 g $l^{-1}$ arabinose.

Within 19 hours the glucose was depleted. Based on the $CO_2$ production profile and arabinose concentrations (FIG. 21) arabinose consumption started after the glucose was completely consumed. No co-consumption of glucose and arabinose was observed. After 74 hours of anaerobic cultivation 99% of the arabinose was consumed. Ethanol was produced with an overall yield of 0.43 g g$^{-1}$ of total sugar. Comparison of the $CO_2$ production profile to that of strain DS62504 (FIG. 24) shows that, based on the first $CO_2$ production peak during anaerobic fermentation of a glucose/arabinose mixture, glucose consumption is slower for strain IMW059. Arabinose however, is consumed much faster by IMW059, which is reflected by the higher $CO_2$ production levels during the second $CO_2$ production peak and the shorter total fermentation time.

EXAMPLE 20

Anaerobic Co-Consumption of Glucose and Arabinose by IMW060

Strain IMW060 was cultivated anaerobically in MY medium with 20 g l$^{-1}$ glucose and 20 g l$^{-1}$ arabinose. Sugar consumption was monitored by HPLC measurements. Growth of the yeast was determined by dry weight measurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Figure 22:
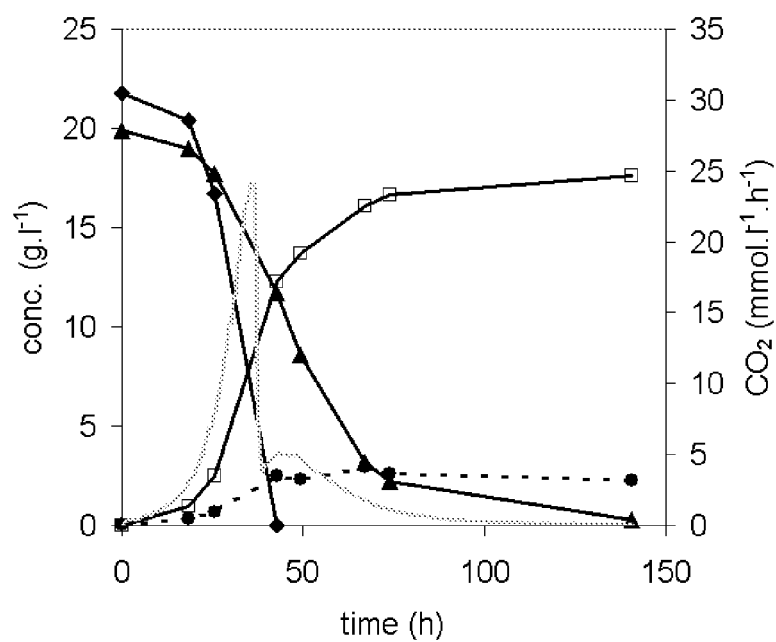
FIG. 22 shows glucose (♦), arabinose (▲), ethanol (□) concentrations, biomass dry weights (●) and CO2 production (solid grey line) during anaerobic cultivation of strain IMW060 in MY medium supplied with 20 g $l^{-1}$ glucose and 20 g $l^{-1}$ arabinose.

Based on the $CO_2$ production profile and glucose and arabinose concentrations (FIG. 22) arabinose is simultaneously consumed with glucose within the first approximately 40 hours. Within the first 43 hours glucose is completely consumed while 41% of the arabinose was consumed. After 74 hours of anaerobic cultivation 89% of the arabinose was consumed. After 140 hours of anaerobic cultivation 98% of the arabinose was consumed. Ethanol was produced with an overall yield of 0.43 g g$^{-1}$ of total sugar. Comparison of the $CO_2$ production profile to that of strain DS62504 (FIG. 24) shows that, based on the first $CO_2$ production peak during anaerobic fermentation of a glucose/arabinose mixture, glucose consumption is slower for strain IMW060. The total time to ferment the glucose/arabinose mixture however, is shorter than that of DS62504.

EXAMPLE 21

Anaerobic Co-Consumption of Glucose and Arabinose by IMW061

Strain IMW061 was cultivated anaerobically in MY medium with 20 g $l^{-1}$ glucose and 20 g $l^{-1}$ arabinose. Sugar consumption was monitored by HPLC measurements. Growth of the yeast was determined by dry weight measurements and monitoring the OD660. $CO_2$ production was determined by measuring $CO_2$ concentrations in the exhaust gas. Ethanol production was calculated based on the $CO_2$ production. To correct for ethanol evaporation the amount of ethanol produced was assumed to be equal to the measured cumulative production of $CO_2$ minus the $CO_2$ production that occurred due to biomass synthesis (5.85 mmol $CO_2$ per gram biomass) and the $CO_2$ associated with acetate formation.

Figure 23:
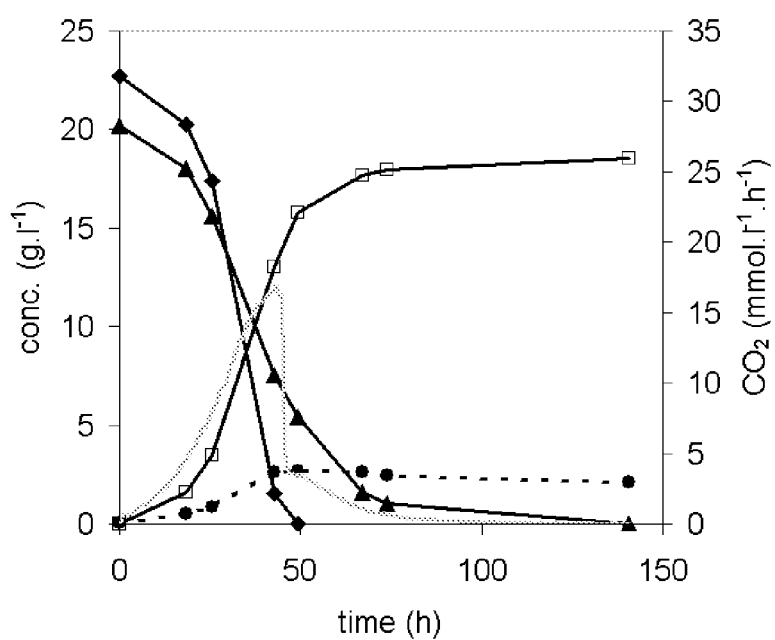
FIG. 23 shows glucose (♦), arabinose (▲), ethanol (□) concentrations, biomass dry weights (●) and CO2 production (solid grey line) during anaerobic cultivation of strain IMW061 in MY medium supplied with 20 g $l^{-1}$ glucose and 20 g $l^{-1}$ arabinose.

Based on the $CO_2$ production profile and glucose and arabinose concentrations (FIG. 23) arabinose is simultaneously consumed with glucose within the first 43 hours. Within the first 49 hours glucose is completely consumed while 73% of the arabinose was consumed. After 74 hours of anaerobic cultivation 95% of the arabinose was consumed. After 140 hours of anaerobic cultivation 99% of the arabinose was consumed. Ethanol was produced with an overall yield of 0.44 g $g^{-1}$ of total sugar. Comparison of the $CO_2$ production profile to that of strain DS62504 (FIG. 24) shows that, based on the first $CO_2$ production peak during anaerobic fermentation of a glucose/arabinose mixture, glucose consumption is slower for strain IMW061. The total time to ferment the glucose/arabinose mixture however, is shorter than that of DS62504.

Performance Test in BAM

In order to test the performance of the strains IMW060 and IMW061, the strains were inoculated in Verduyn medium, supplemented with 2% glucose. As controls, strain DS62504, was included.

After overnight incubation at 30° C. and 280 rpm in a rotary shaker, cells were harvested by centrifugation and cultivations for $CO_2$ production were performed at 33° C. in the BAM (Biological Activity Monitor), in 100 ml Verduyn medium supplemented with the sugars indicated in table 7. The cells were added to the 100 ml of Verduyn medium supplemented with the sugars and the inhibitors acetic acid, coumaric acid, ferulic acid, furfural, HMF and formic acid at the indicated concentrations. In a second experiment, 100 ml of Verduyn medium supplemented with the sugars but without inhibitors was used. The $CO_2$ production was constantly monitored, and samples were taken at intervals for analysis (optical density at 600 nm, ethanol, and residual sugars).

Figure 25:
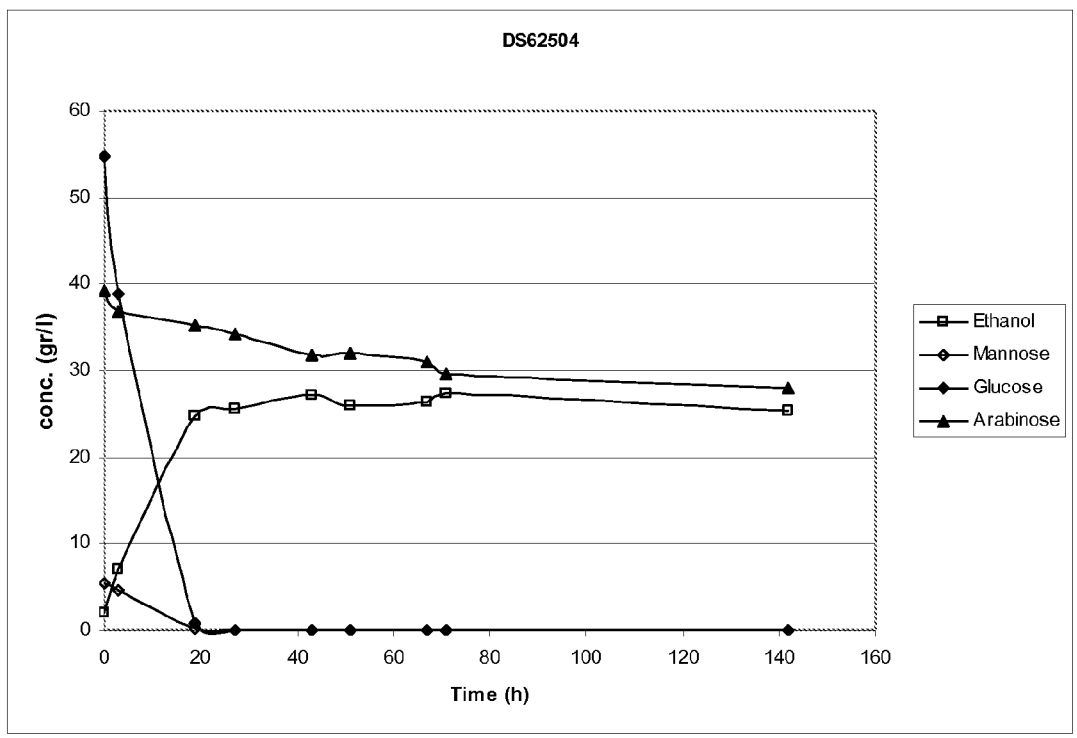
FIG. 25 shows glucose (♦), mannose (◇), arabinose (▲) and ethanol (□) concentrations during shake flask cultivations of strain DS62504 on medium CFMM2M.
Figure 26:
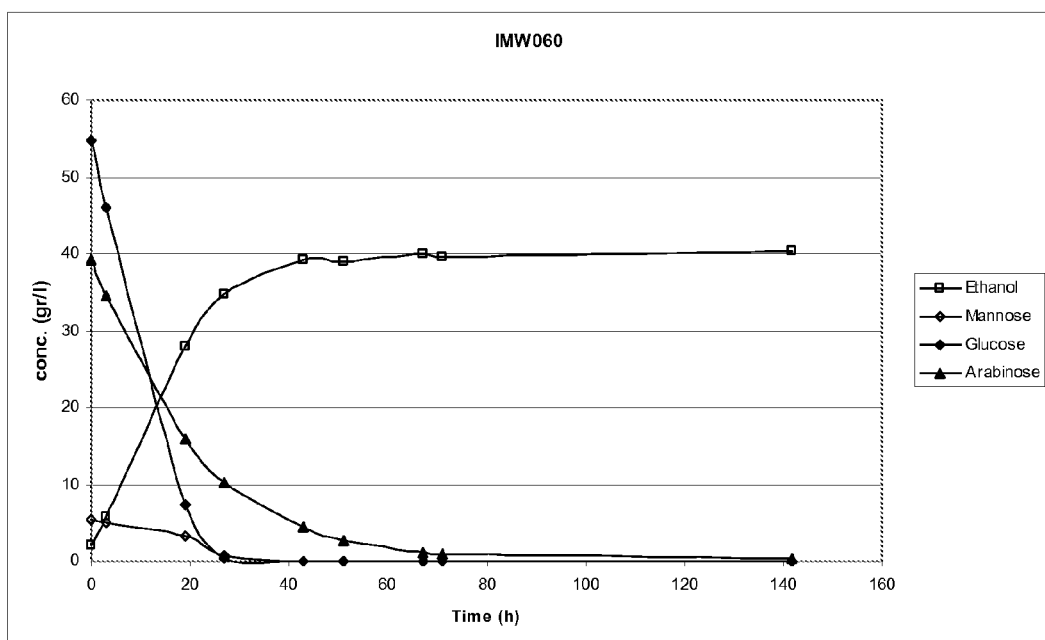
FIG. 26 shows glucose (♦), mannose (◇), arabinose (▲) and ethanol (□) concentrations during shake flask cultivations of strain IMW060 on medium CFMM2M.
Figure 27:
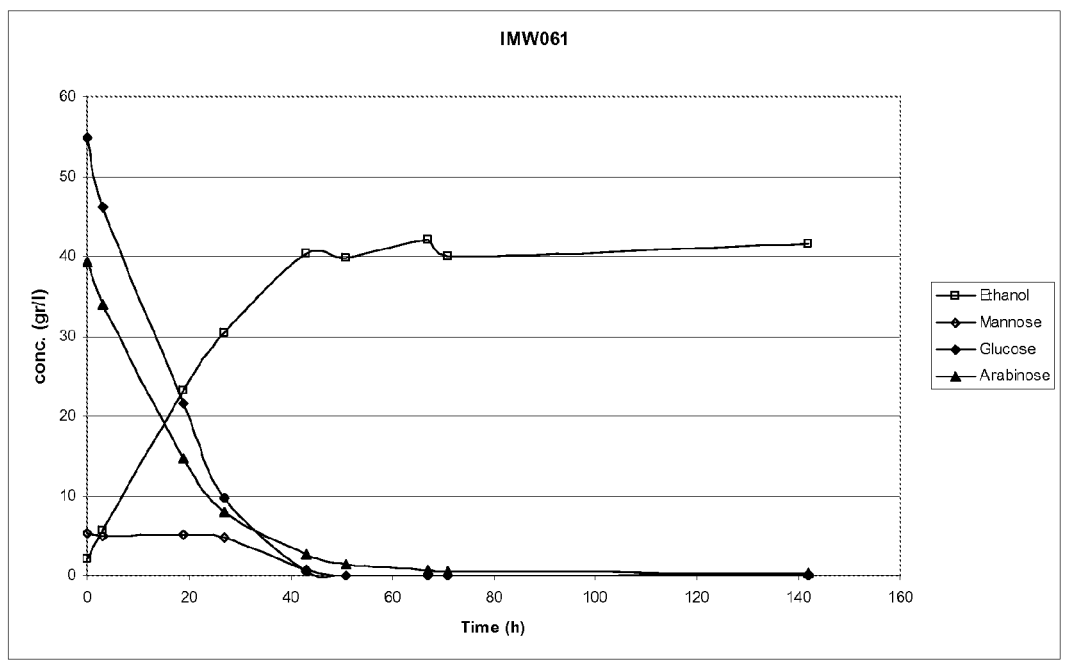
FIG. 27 shows glucose (♦), mannose (◇), arabinose (▲) and ethanol (□) concentrations during shake flask cultivations of strain IMW061 on medium CFMM2M.
Figure 28:
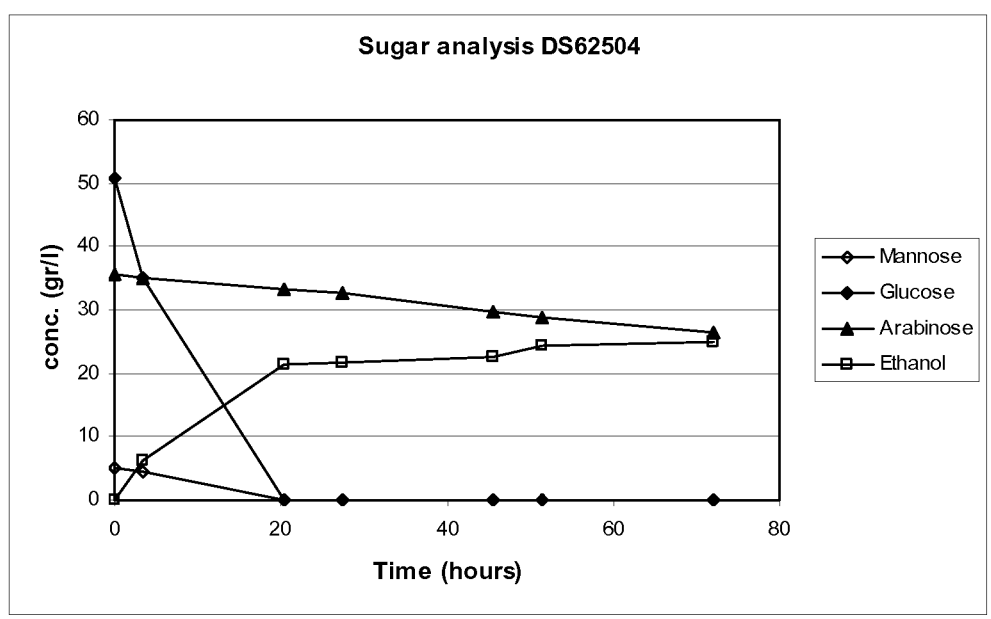
FIG. 28 shows glucose (♦), mannose (◇), arabinose (▲) and ethanol (□) concentrations during shake flask cultivations of strain DS62504 on medium CFMM1 M.
Figure 29:
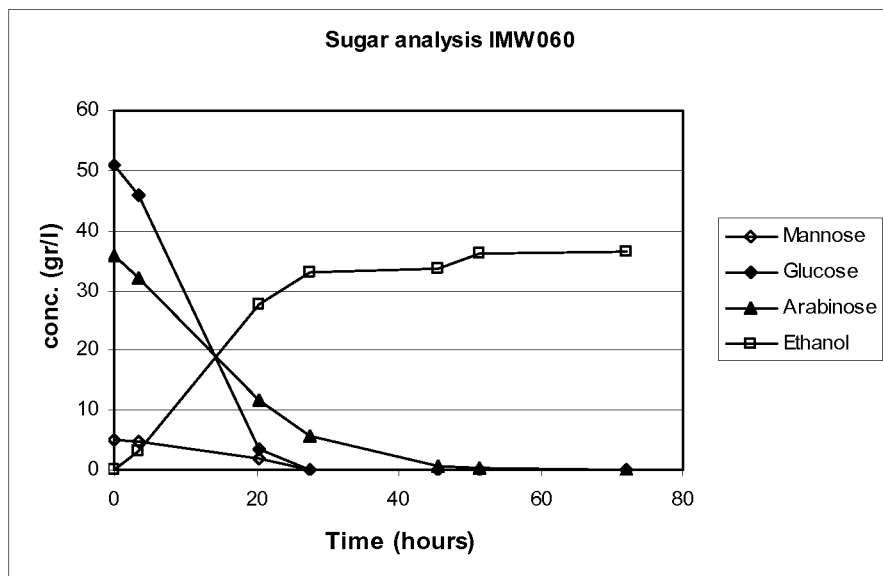
FIG. 29 shows glucose (♦), mannose (◇), arabinose (▲) and ethanol (□) concentrations during shake flask cultivations of strain IMW060 on medium CFMM1 M.
Figure 30:
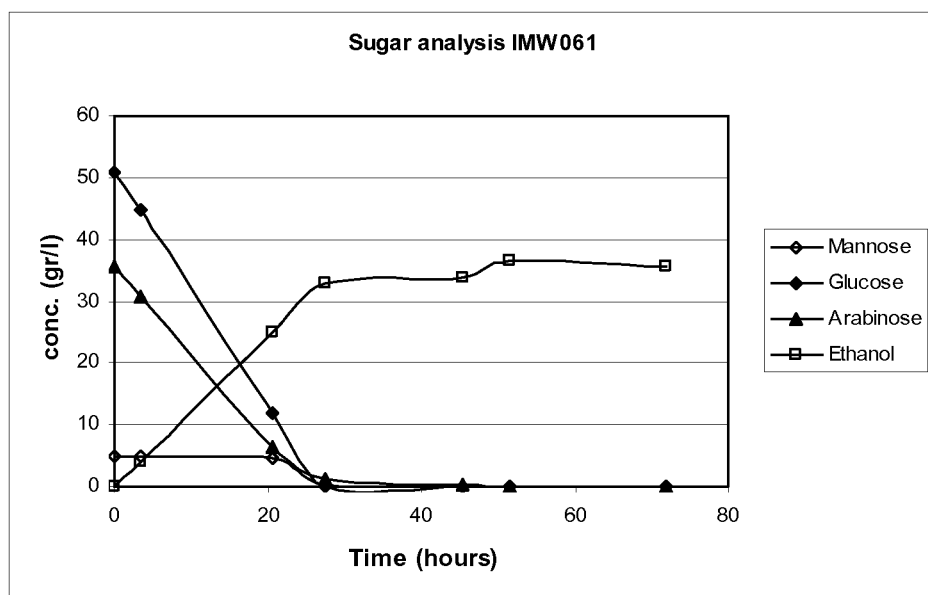
FIG. 30 shows glucose (♦), mannose (◇), arabinose (▲) and ethanol (□) concentrations during shake flask cultivations of strain IMW061 on medium CFMM1 M.

The results of the BAM experiment are shown in FIGS. 25, 26, and 27 for the medium with inhibitors and 28, 29 and 30 for the medium without inhibitors. It can be concluded that both IMW060 and IMW061 are capable of converting the sugars glucose and arabinose fast and simultaneously into ethanol, while the strain DS62504 can not, i.e DS62504 consumes arabinose after the glucose is exhausted from the medium. The same result, i.e. co-consumption of arabinose and glucose, is obtained in the presence of inhibitors, although the time it takes to consume all sugars is slower in the presence of inhibitors, as is known from the literature.

TABLE 7

Composition of the Verduyn medium CFMM2M; CFMM1M has the same composition except without inhibitors:

| Component | Amount (g/l) |
| --- | --- |
| Glucose | 55 |
| Arabinose | 35 |
| Mannose | 5 |
| Acetic Acid | 3.0 |
| Coumaric Acid* | 0.03 |
| Ferulic Acid* | 0.2 |
| Furfural** | 0.1 |
| HMF | 0.1 |
| Formic Acid | 0.1 |

REFERENCES

[1] A. A. Andreasen, T. J. Stier, Anaerobic nutrition of *Saccharomyces cerevisiae*. I. Ergosterol requirement for growth in a defined medium, J. Cell Physiol. 41 (1953) 23-36.

[2] A. A. Andreasen, T. J. Stier, Anaerobic nutrition of *Saccharomyces cerevisiae*. Unsaturated fatty acid requirement for growth in a defined medium, J. Cell Physiol. 43 (1954) 271-281.

[3] R. D. Gietz, R. A. Woods, Transformation of yeast by lithium acetate/single-stranded carrier DNA/polyethylene glycol method, Methods Enzymol. 350 (2002) 87-96.

[4] U. Güldener, S. Heck, T. Fiedler, J. Beinhauer, J. H. Hegemann, A new efficient gene disruption cassette for repeated use in budding yeast, Nucleic Acids Res. 24 (1996) 2519-2524.

[5] U. Güldener, J. Heinisch, G. J. Koehler, D. Voss, J. H. Hegemann, A second set of loxP marker cassettes for Cre-mediated multiple gene knockouts in budding yeast, Nucleic Acids Research 30(6) (2002) e23.

[6] H. Van Urk, P. R. Mak, W. A. Scheffers, J. P. Van Dijken, Metabolic responses of *Saccharomyces cerevisiae* CBS 8066 and *Candida utilis* CBS 621 upon transition from glucose limitation to glucose excess, Yeast 4 (1988) 283-291.

[7] C. Verduyn, E. Postma, W. A. Scheffers, J. P. Van Dijken, Effect of benzoic acid on metabolic fluxes in yeasts: a continuous-culture study on the regulation of respiration and alcoholic fermentation, Yeast 8 (1992) 501-517.

[8] R. A. Weusthuis, W. Visser, J. T. Pronk, W. A. Scheffers, J. P. Van Dijken, Effects of oxygen limitation on sugar metabolism in yeasts—a continuous-culture study of the Kluyver effect, Microbiology 140 (1994) 703-715.

[9] S. C. Kou, et al. (1970). J. Bact. 102, 671-678.

[10] J. Becker et al. (2003). Appl. Environ. Microbiol. 69, 4144-4150.

[11] J. B. Thoden et al. (2005). J. Biol. Chem. 280, 36905-36911

The invention claimed is:

1. An isolated polypeptide having a mutation at a position corresponding to at least one position corresponding to T219, of SEQ ID NO: 55, wherein said polypeptide comprises at least 90% sequence identity with SEQ ID NO: 55, and wherein the polypeptide comprises permease activity.

2. The polypeptide according to claim 1, wherein said polypeptide comprises a substitution T219N or T219Q.

3. The polypeptide according to claim 1, wherein said polypeptide comprises substitution T219N.

4. The polypeptide according to claim 1, wherein said polypeptide comprises galactose permease (GAL2) activity.

5. The polypeptide according to claim 1, comprising at least one of the following amino acid or amino acid sequences:
   a) G90;
   b) G135;
   c) G147;
   d) G184-X(3)-G188-X(11)-E200-X(2)-P203-X(3)-R207-X(7)-Q215;
   e) Q215;
   f) G345-X(1)-N347;
   g) Y352;
   h) Y446;
   i) E460;
   j) F504; or
   k) E521;
   wherein the positions in a) to k) in the polypeptide correspond to the positions in SEQ ID NO: 55.

6. The polypeptide according to claim 1, comprising a sequence GXXXGXXXXXXXXXXXEXX-PXXXRXXXXXXXQ.

7. An isolated polynucleotide encoding the polypeptide according to claim 1.

8. A nucleic acid construct comprising the polynucleotide of claim 7.

9. An isolated host cell transformed with said nucleic acid construct of claim 8.

10. A transformed host cell according to claim 9, which is yeast.

11. The transformed host cell according to claim 10, which belongs to the genus *Saccharomyces*.

12. The transformed host cell according to claim 11, which belongs to the species *Saccharomyces cerevisiae*.

13. A process for degradating ligno-cellulosic or hemi-cellulosic material, said process comprising contacting ligno-cellulosic or hemi-cellulosic material with an enzyme composition, producing at least one sugar, and fermenting produced sugar to give a fermentation product, and wherein said fermenting is conducted with a transformed host cell of claim 9.

14. The process according to claim 13, wherein said fermentation product is at least one selected from the group consisting of:

ethanol, butanol, lactic acid, a plastic, an organic acid, a solvent, an animal feed supplement, a pharmaceutical, a vitamin, an amino acid, an enzyme and a chemical feedstock.

* * * * *

SEQUENCE LISTING

<160> NUMBER OF SEQ ID NOS: 58

<210> SEQ ID NO 1
<211> LENGTH: 62
<212> TYPE: DNA
<213> ORGANISM: Artificial Sequence
<220> FEATURE:
<223> OTHER INFORMATION: Synthetic DNA

<400> SEQUENCE: 1
gttgtaggaa tataattctc cacacataat aagtacgcta attcagctga agcttcgtac    60
gc                                                                  62

<210> SEQ ID NO 2
<211> LENGTH: 67
<212> TYPE: DNA
<213> ORGANISM: Artificial Sequence
<220> FEATURE:
<223> OTHER INFORMATION: Synthetic DNA

<400> SEQUENCE: 2
aaaagggcac cttcttgttg ttcaaactta atttacaaat taagtgcata ggccactagt    60
ggatctg                                                             67

<210> SEQ ID NO 3
<211> LENGTH: 63
<212> TYPE: DNA
<213> ORGANISM: Artificial Sequence
<220> FEATURE:
<223> OTHER INFORMATION: Synthetic DNA

<400> SEQUENCE: 3
tttcttttaa tcaaactcac ccaaacaact caattagaat actgcagctg aagcttcgta    60
cgc                                                                 63

<210> SEQ ID NO 4
<211> LENGTH: 69
<212> TYPE: DNA
<213> ORGANISM: Artificial Sequence
<220> FEATURE:
<223> OTHER INFORMATION: Synthetic DNA

<400> SEQUENCE: 4
gaataataat attaagggag ggaaaaacac atttatattt cattacagca taggccacta    60
gtggatctg                                                           69

<210> SEQ ID NO 5
<211> LENGTH: 64
<212> TYPE: DNA
<213> ORGANISM: Artificial Sequence
<220> FEATURE:
<223> OTHER INFORMATION: Synthetic DNA

<400> SEQUENCE: 5
ctcggacaaa ggtcttccta tgattccggc gttcgtcacc gggtccagct gaagcttcgt    60
acgc                                                                64

<210> SEQ ID NO 6
<211> LENGTH: 64
<212> TYPE: DNA
<213> ORGANISM: Artificial Sequence
<220> FEATURE:
<223> OTHER INFORMATION: Synthetic DNA

<400> SEQUENCE: 6
taaaggagag aagatggtaa gtacggtggg atacgtacac aaacataggc cactagtgga    60
tctg                                                                64

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
cgcacgtcaa gactgtcaag                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
tcgtatgtga atgctggtcg                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
ttcgccactg tcttatctac                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ccgttcgttc cagaattatc                                                20

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA

<400> SEQUENCE: 11
ccttaggacc gttgagagga atag                                           24

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
tcccggagaa caaagtaagt gg                                             22

```
<210> SEQ ID NO 13
<211> LENGTH: 25
<212> TYPE: DNA
<213> ORGANISM: Artificial Sequence
<220> FEATURE:
<223> OTHER INFORMATION: Synthetic DNA

<400> SEQUENCE: 13
aaaaacggga aataacaata acgac                                         25

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
tgcgatctta ttagtgtgtg acatt                                         25

<210> SEQ ID NO 15
<211> LENGTH: 1458
<212> TYPE: DNA
<213> ORGANISM: Saccharomyces cerevisiae S288C

<400> SEQUENCE: 15
atggttcatt taggtccaaa gaaaccacag gctagaaagg gttccatggc tgatgtgccc      60
aaggaattga tggatgaaat tcatcagttg aagatatgt ttacagttga cagcgagacc     120
ttgagaaagg ttgttaagca ctttatcgac gaattgaata aaggtttgac aaagaaggga    180
ggtaacattc caatgattcc cggttgggtc atggaattcc caacaggtaa agaatctggt    240
aactatttgg ccattgattt gggtggtact aacttaagag tcgtgttggt caagttgagc    300
ggtaaccata cctttgacac cactcaatcc aagtataaac taccacatga catgagaacc    360
actaagcacc aagaggagtt atggtccttt attgccgact ctttgaagga ctttatggtc    420
gagcaagaat tgctaaacac caaggacacc ttaccattag gtttcacctt ctcgtaccca    480
gcttcccaaa acaagattaa cgaaggtatt ttgcaaagat ggaccaaggg tttcgatatt    540
ccaaatgtcg aaggccacga tgtcgtccca ttgctacaaa acgaaatttc caagagagag    600
ttgcctattg aaattgtagc attgattaat gatactgttg gtactttaat tgcctcatac    660
tacactgacc cagagactaa gatgggtgtg attttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt tgtgggtatt   1200
gccgctattt gccaaaagag aggttacaag actggtcaca ttgccgctga cggttctgtc   1260
tataacaaat acccaggttt caaggaagcc gccgctaagg gttgagagaa tatctatgga   1320
tggactggtg acgcaagcaa agatccaatt acgattgttc cagctgagga tggttcaggt   1380
```

```
gcaggtgctg ctgttattgc tgcattgtcc gaaaaaagaa ttgccgaagg taagtctctt    1440
ggtatcattg gcgcttaa                                                  1458

<210> SEQ ID NO 16
<211> LENGTH: 1461
<212> TYPE: DNA
<213> ORGANISM: Saccharomyces cerevisiae S288C

<400> SEQUENCE: 16
atggttcatt taggtccaaa aaaccacaa gccagaaagg gttccatggc cgatgtgcca      60
aaggaattga tgcaacaaat tgagaatttt gaaaaaattt tcactgttcc aactgaaact    120
ttacaagccg ttaccaagca cttcatttcc gaattggaaa agggtttgtc caagaagggt    180
ggtaacattc aatgattcc aggttgggtt atggatttcc caactggtaa ggaatccggt     240
gatttcttgg ccattgattt gggtggtacc aacttgagag ttgtcttagt caagttgggc    300
ggtgaccgta cctttgacac cactcaatct aagtacagat accagatgc tatgagaact     360 actcaaaatc cagacgaatt gtgggaattt attgccgact ctttgaaagc ttttattgat    420
gagcaattcc acaaggtat ctctgagcca attccattgg gtttcacctt ttcttttccca    480 gcttctcaaa acaaaatcaa tgaaggtatc ttgcaaagat ggactaaagg ttttgatatt    540
ccaaacattg aaaaccacga tgttgttcca atgttgcaaa agcaaatcac taagaggaat    600
atcccaattg aagttgttgc tttgataaac gacactaccg tactttggt tgcttcttac     660 tacactgacc cagaaactaa gatgggtgtt atcttcggta ctggtgtcaa tggtgcttac    720
tacgatgttt gttccgatat cgaaaagcta caaggaaaac tatctgatga cattccacca    780
tctgctccaa tggccatcaa ctgtgaatac ggttccttcg ataatgaaca tgtcgttttg    840
ccaagaacta aatacgatat caccattgat gaagaatctc caagaccagg ccaacaaacc    900
tttgaaaaaa tgtcttctgg ttactactta ggtgaaattt gcgtttggc cttgatggac     960 atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga cgtaaaattg   1140
atcagacgtt tatctgaatt gattggtgct agagctgcta gattgtccgt tgtggtatt    1200 gctgctatct gtcaaaagag aggttacaag accggtcaca tcgctgcaga cggttccgtt   1260
tacaacagat acccaggttt caagaaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                             1461

<210> SEQ ID NO 17
<211> LENGTH: 1503
<212> TYPE: DNA
<213> ORGANISM: Saccharomyces cerevisiae S288C

<400> SEQUENCE: 17
atgtcattcg acgacttaca caagccact gagagagcgg tcatccaggc cgtggaccag      60
atctgcgacg atttcgaggt tacccccgag aagctggacg aattaactgc ttacttcatc    120
gaacaaatgg aaaaaggtct agctccacca aaggaaggcc acacattggc ctcggacaaa    180
ggtcttccta tgattccggc gttcgtcacc gggtcaccca acgggacgga gcgcggtgtt    240
ttactagccg ccgacctggg tggtaccaat ttccgtatat gttctgttaa cttgcatgga   300
```

-continued

```
gatcatactt tctccatgga gcaaatgaag tccaagattc ccgatgattt gctagacgat        360
gagaacgtca catctgacga cctgtttggg tttctagcac gtcgtacact ggcctttatg        420
aagaagtatc acccggacga gttggccaag ggtaaagacg ccaagcccat gaaactgggg        480
ttcactttct catacctgt agaccagacc tctctaaact ccgggacatt gatccgttgg         540
accaagggtt ccgcatcgc ggacaccgtc ggaaaggatg tcgtgcaatt gtaccaggag         600
caattaagcg ctcagggtat gcctatgatc aaggttgttg cattaaccaa cgacaccgtc        660
ggaacgtacc tatcgcattg ctacacgtcc gataacacgg actcaatgac gtccggagaa       720
atctcggagc cggtcatcgg atgtattttc ggtaccggta ccaatgggtg ctatatggag       780
gagatcaaca agatcacgaa gttgccacag gagttgcgtg acaagttgat aaaggagggt       840
aagcacacac tgatcatcaa tgtcgaatgg gggtccttcg ataatgagct caagcacttg       900
cctactacta agtatgacgt cgtaattgac cagaaactgt caacgaaccc gggatttcac       960
ttgtttgaaa aacgtgtctc agggatgttc ttgggtgagg tgttgcgtaa cattttagtg      1020
gacttgcact cgcaaggctt gcttttgcaa cagtacaggt ccaaggaaca acttcctcgc      1080
cacttgacta caccttttcca gttgtcatcc gaagtgctgt cgcatattga aattgacgac      1140
tcgacaggtc tacgtgaaac agagttgtca ttattacaga gtctcagact gcccaccact      1200
ccaacagagc gtgttcaaat tcaaaaattg gtgcgcgcga tttctaggag atctgcgtat      1260
ttagccgccg tgccgcttgc cgcgatattg atcaagacaa atgctttgaa caagagatat      1320
catggtgaag tcgagatcgg ttgtgatggt tccgttgtgg aatactaccc cggtttcaga      1380
tctatgctga gacacgcctt agccttgtca cccttgggtg ccgagggtga gaggaaggtg      1440
cacttgaaga ttgccaagga tggttccgga gtgggtgccg ccttgtgtgc gcttgtagca      1500
tga                                                                   1503
```

<210> SEQ ID NO 18
<211> LENGTH: 1587
<212> TYPE: DNA
<213> ORGANISM: Saccharomyces cerevisiae S288C

<400> SEQUENCE: 18

```
atgactaaat ctcattcaga agaagtgatt gtacctgagt tcaattctag cgcaaaggaa         60
ttaccaagac cattggccga aaagtgcccg agcataatta gaaatttat aagcgcttat        120 gatgctaaac cggattttgt tgctagatcg cctggtagag tcaatctaat tggtgaacat        180
attgattatt gtgacttctc ggttttacct ttagctattg attttgatat gctttgcgcc       240
gtcaaagttt tgaacgagaa aaatccatcc attaccttaa taaatgctga tcccaaattt      300
gctcaaagga agttcgattt gccgttggac ggttcttatg tcacaattga tccttctgtg      360
tcggactggt ctaattactt taaatgtggt ctccatgttg ctcactcttt tctaaagaaa       420
cttgcaccgg aaaggtttgc cagtgctcct ctggccgggc tgcaagtctt ctgtgagggt      480
gatgtaccaa ctggcagtgg attgtcttct tcggccgcat tcatttgtgc cgttgcttta     540
gctgttgtta aagcgaatat gggccctggt tatcatatgt ccaagcaaaa tttaatgcgt     600
attacggtcg ttgcagaaca ttatgttggt gttaacaatg cggtatggga tcaggctgcc    660
tctgtttgcg gtgaggaaga tcatgctcta tacgttgagt tcaaaccgca gttgaaggct   720 actccgtttaa aatttccgca attaaaaaac catgaaatta gctttgttat tgcgaacacc    780
cttgttgtat ctaacaagtt tgaaaccgcc ccaaccaact ataatttaag agtggtagaa     840
```

| | |
|---|---|
| gtcactacag ctgcaaatgt tttagctgcc acgtacggtg ttgttttact ttctggaaaa | 900 |
| gaaggatcga gcacgaataa aggtaatcta agagatttca tgaacgttta ttatgccaga | 960 |
| tatcacaaca tttccacacc ctggaacggc gatattgaat ccggcatcga acggttaaca | 1020 |
| aagatgctag tactagttga agagtctctc gccaataaga aacagggctt tagtgttgac | 1080 |
| gatgtcgcac aatccttgaa ttgttctcgc gaagaattca aagagacta cttaacaaca | 1140 |
| tctccagtga gatttcaagt cttaaagcta tcagaggg ctaagcatgt gtattctgaa | 1200 |
| tctttaagag tcttgaaggc tgtgaaatta atgactacag cgagctttac tgccgacgaa | 1260 |
| gacttttca agcaatttgg tgccttgatg aacgagtctc aagcttcttg cgataaactt | 1320 |
| tacgaatgtt cttgtccaga gattgacaaa atttgttcca ttgctttgtc aaatggatca | 1380 |
| tatggttccc gtttgaccgg agctggctgg ggtggttgta ctgttcactt ggttccaggg | 1440 |
| ggcccaaatg gcaacataga aaaggtaaaa gaagcccttg ccaatgagtt ctacaaggtc | 1500 |
| aagtacccta agatcactga tgctgagcta gaaaatgcta tcatcgtctc taaaccagca | 1560 |
| ttgggcagct gtctatatga attataa | 1587 |

<210> SEQ ID NO 19
<211> LENGTH: 1503
<212> TYPE: DNA
<213> ORGANISM: Saccharomyces cerevisiae S288C

<400> SEQUENCE: 19

| | |
|---|---|
| atgtcatttg aaaatttaca taaagtcaat gctgaggcat ggaagatgc agtggttgag | 60 |
| atctgctcct cattgcaggt tgatgcagca aagttgacg aactaacagc gtacttcatt | 120 |
| gaatgtatgg aaaagggggtt gaataacacc tctgtaggcg aagaaaagac ggtggacaag | 180 |
| ggtctaccca tgatccctac atatgtaacc agttgccca atgggacgga acgtggtgtt | 240 |
| ttgctggctg cagatttagg tgggactcac ttcagagtgt gttctgtgac tttgaatggt | 300 |
| gacgaacct tgatatgca gcaattgaag tctaagattc cggaagaata tctaaatgac | 360 |
| aaggatgtca ccagcgagga gctgtttagc tacctgggtc gccgtacaag ggccttcgtt | 420 |
| aggaagcatc atcctgagtt gttgaagtcc acggggagga acataaaacc tttgaaaatg | 480 |
| ggatttacct tctcatatcc cgttgaccaa acctctttga gttccggtac tttaatcaga | 540 |
| tggaccaaaa gcttcaagat tgaagacacg gtcggcaagg atgtcgtgag gttataccag | 600 |
| gagcaattag acattcaggg gctctctatg attaatgtgg tagctttgac caacgacacg | 660 |
| gttggcactt tcctatccca ctgctacact tcaggctctc gtccatcgag tgctggtgag | 720 |
| attagcgagc ctgtcattgg ttgtatcttt ggtactggta ctaacggttg ctatatggag | 780 |
| gatattgaaa acatcaagaa gctaccagat gagctcagaa caagactgct gcatgaagga | 840 |
| aaaaccccaaa tgtgcatcaa catcgaatgg ggttctttcg acaatgaatt gaaacatttg | 900 |
| tctgctacaa agtatgacat cgatattgac caaaatttt ctccaaatcc aggttaccat | 960 |
| ctatttgaaa aagaatttc cggcatgtac ttgggtgagc tgttaaggaa catcctggtg | 1020 |
| gacttgcatg caaggggctt aatcttggga cagtatcgta attacgatca attacctcac | 1080 |
| cgtttaaaga ctcctttcca attgtgcagt gaagttcttt ccaggattga aatcgatgat | 1140 |
| tcgacaaact gcgtgaaaac tgaattgtcg ttttttgcaga gtttgaggct accgaccact | 1200 |
| tttgaagaac gtaaagcaat tcaaaatctg gtccgttcca ttacgagaag gtctgcatat | 1260 |
| ctagcagccg ttccgattgc cgccatccta atcaagacaa acgctttgaa caaaagatat | 1320 |
| cacggtgagg tagaaattgg ttttgacggt tatgtcatcg aatactatcc tggattcaga | 1380 |

```
tccatgctga gacatgcttt ggcattaagt ccaattggca ctgagggtga acgtaagata   1440
catttgcgtc tagccaaaga tgggtccggt gttggcgcag ctttgtgtgc tctggtggca   1500
taa                                                                 1503
```

<210> SEQ ID NO 20
<211> LENGTH: 1302
<212> TYPE: DNA
<213> ORGANISM: Saccharomyces cerevisiae S288C

<400> SEQUENCE: 20

```
atgacaattg aaagcactct agctcgggaa ttagaaagct tgattttacc cgctgattcc     60
atagtgaatg tagttgacca attccaagag gagttgttat cacggcttca gacaaatacg    120
atttctatgc tcccgcagtg tttagtccca gataaacgat cgcgatggaa ccctgaagac    180
aaaattctga ccattgattt cggcgggaca agactgaaat tgcaattat ctctctgccc     240 caaatcgtta tcgaatacaa tgatgccttc gaacttacct acaacatcgt tgattcgaat    300
ttctttaatc aaatcatcta tacaatatgt accaggctgg ctgcaaatgg ttatataaaa    360
aaaaagaacg agtcatctga ggcgtctaaa ttttttgttt ccgtgacatt cagttttcct    420
ctaaatccag aaggggaggt agttgcaatg ggaaaaggat tgtgatgac tgacacccctt    480 caaggatcca cggtgaaaca gctcatccaa tcttcctttc accggattat atcagaaaat    540
atcgaagaat ttttctgtac catgaacgtg tgtcatgtaa taaacgatgc aattgcagtt    600
tcactaacaa gcaaatttat atgcgaaaac gattccatct cattaataat aggaactggt    660
acaaatgcat gttttgaggt tccatacgga tatttaccac ctttcaagag agatgccctg    720
agagaaacat taccgtcaag ctataataag gagacattaa atttcaaaca tgttctcatt    780
aattctgaaa ttggctttat tggtaaaaat gtcattgcat tgcaaccgtt tgacattcat    840
ggagcaatct catacgaaat gccactagag tgcgttactt ctggtaaatg gcttccccta    900
tcattaaaaa atattctatt gcaatataac ataatcccca aaaacttccc agtagagttc    960
aatggggaac tggtatgcca gctggcagaa gactgtacta atgcttggtt cgaaaacgaa   1020
cattatgcac taatttgtca gatcgcacga ctattaatca agagagccgc attttatgtt   1080
gctgcaattg tacaagctat tgatatcatc acaggctgca aaaactataa ctttattcat   1140
attggctacg ttgatccttt ctccacaat tcaaatttttt atcgagagca gataaaatat   1200
tactccagca tacatattaa gttgcaattc ttaaatcaca gtaatcttct aggcgctgca   1260
atagccacct acttgaacaa atcagacaac caagttcaat aa                      1302
```

<210> SEQ ID NO 21
<211> LENGTH: 485
<212> TYPE: PRT
<213> ORGANISM: Saccharomyces cerevisiae S288C

<400> SEQUENCE: 21

```
Met Val His Leu Gly Pro Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Val Lys His Phe
            35                  40                  45

Ile Asp Glu Leu Asn Lys Gly Leu Thr Lys Lys Gly Gly Asn Ile Pro
        50                  55                  60
```

```
Met Ile Pro Gly Trp Val Met Glu Phe Pro Thr Gly Lys Glu Ser Gly
 65                  70                  75                  80

Asn Tyr Leu Ala Ile Asp Leu Gly Gly Thr Asn Leu Arg Val Val Leu
                 85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
    210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
    290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
        355                 360                 365

Phe Gly Val Lys Thr Thr Leu Pro Glu Arg Lys Leu Ile Arg Arg Leu
    370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
    450                 455                 460

Val Ile Ala Ala Leu Ser Glu Lys Arg Ile Ala Glu Gly Lys Ser Leu
465                 470                 475                 480

Gly Ile Ile Gly Ala
```

<210> SEQ ID NO 22
<211> LENGTH: 486
<212> TYPE: PRT
<213> ORGANISM: Saccharomyces cerevisiae S288C

<400> SEQUENCE: 22

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365
```

```
Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
                435                 440                 445

Tyr Pro Ile Lys Ile Val Pro Ala Glu Asp Gly Ser Gly Ala Gly Ala
450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 23
<211> LENGTH: 500
<212> TYPE: PRT
<213> ORGANISM: Saccharomyces cerevisiae S288C

<400> SEQUENCE: 23

Met Ser Phe Asp Asp Leu His Lys Ala Thr Glu Arg Ala Val Ile Gln
1               5                   10                  15

Ala Val Asp Gln Ile Cys Asp Asp Phe Glu Val Thr Pro Glu Lys Leu
                20                  25                  30

Asp Glu Leu Thr Ala Tyr Phe Ile Glu Gln Met Glu Lys Gly Leu Ala
            35                  40                  45

Pro Pro Lys Glu Gly His Thr Leu Ala Ser Asp Lys Gly Leu Pro Met
        50                  55                  60

Ile Pro Ala Phe Val Thr Gly Ser Pro Asn Gly Thr Glu Arg Gly Val
65                  70                  75                  80

Leu Leu Ala Ala Asp Leu Gly Gly Thr Asn Phe Arg Ile Cys Ser Val
                85                  90                  95

Asn Leu His Gly Asp His Thr Phe Ser Met Glu Gln Met Lys Ser Lys
                100                 105                 110

Ile Pro Asp Asp Leu Leu Asp Asp Glu Asn Val Thr Ser Asp Asp Leu
            115                 120                 125

Phe Gly Phe Leu Ala Arg Arg Thr Leu Ala Phe Met Lys Lys Tyr His
        130                 135                 140

Pro Asp Glu Leu Ala Lys Gly Lys Asp Ala Lys Pro Met Lys Leu Gly
145                 150                 155                 160

Phe Thr Phe Ser Tyr Pro Val Asp Gln Thr Ser Leu Asn Ser Gly Thr
                165                 170                 175

Leu Ile Arg Trp Thr Lys Gly Phe Arg Ile Ala Asp Thr Val Gly Lys
            180                 185                 190

Asp Val Val Gln Leu Tyr Gln Glu Gln Leu Ser Ala Gln Gly Met Pro
        195                 200                 205

Met Ile Lys Val Val Ala Leu Thr Asn Asp Thr Val Gly Thr Tyr Leu
    210                 215                 220

Ser His Cys Tyr Thr Ser Asp Asn Thr Asp Ser Met Thr Ser Gly Glu
225                 230                 235                 240

Ile Ser Glu Pro Val Ile Gly Cys Ile Phe Gly Thr Gly Thr Asn Gly
                245                 250                 255
```

```
Cys Tyr Met Glu Glu Ile Asn Lys Ile Thr Lys Leu Pro Gln Glu Leu
            260                 265                 270

Arg Asp Lys Leu Ile Lys Glu Gly Lys Thr His Met Ile Asn Val
        275                 280                 285

Glu Trp Gly Ser Phe Asp Asn Glu Leu Lys His Leu Pro Thr Thr Lys
    290                 295                 300

Tyr Asp Val Val Ile Asp Gln Lys Leu Ser Thr Asn Pro Gly Phe His
305                 310                 315                 320

Leu Phe Glu Lys Arg Val Ser Gly Met Phe Leu Gly Glu Val Leu Arg
                325                 330                 335

Asn Ile Leu Val Asp Leu His Ser Gln Gly Leu Leu Gln Gln Tyr
            340                 345                 350

Arg Ser Lys Glu Gln Leu Pro Arg His Leu Thr Thr Pro Phe Gln Leu
            355                 360                 365

Ser Ser Glu Val Leu Ser His Ile Glu Ile Asp Asp Ser Thr Gly Leu
    370                 375                 380

Arg Glu Thr Glu Leu Ser Leu Leu Gln Ser Leu Arg Leu Pro Thr Thr
385                 390                 395                 400

Pro Thr Glu Arg Val Gln Ile Gln Lys Leu Val Arg Ala Ile Ser Arg
                405                 410                 415

Arg Ser Ala Tyr Leu Ala Ala Val Pro Leu Ala Ala Ile Leu Ile Lys
            420                 425                 430

Thr Asn Ala Leu Asn Lys Arg Tyr His Gly Glu Val Glu Ile Gly Cys
        435                 440                 445

Asp Gly Ser Val Val Glu Tyr Tyr Pro Gly Phe Arg Ser Met Leu Arg
    450                 455                 460

His Ala Leu Ala Leu Ser Pro Leu Gly Ala Glu Gly Glu Arg Lys Val
465                 470                 475                 480

His Leu Lys Ile Ala Lys Asp Gly Ser Gly Val Gly Ala Ala Leu Cys
                485                 490                 495

Ala Leu Val Ala
        500

<210> SEQ ID NO 24
<211> LENGTH: 528
<212> TYPE: PRT
<213> ORGANISM: Saccharomyces cerevisiae S288C

<400> SEQUENCE: 24

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
```

```
            115                 120                 125
Cys Gly Leu His Val Ala His Ser Phe Leu Lys Lys Leu Ala Pro Glu
130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
        275                 280                 285

Ala Ala Thr Tyr Gly Val Val Leu Leu Ser Gly Lys Glu Gly Ser Ser
    290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
        355                 360                 365

Ser Arg Glu Glu Phe Thr Arg Asp Tyr Leu Thr Thr Ser Pro Val Arg
    370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Ala Ser Phe
                405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
        435                 440                 445

Asp Lys Ile Cys Ser Ile Ala Leu Ser Asn Gly Ser Tyr Gly Ser Arg
    450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
        515                 520                 525

<210> SEQ ID NO 25
```

<211> LENGTH: 500
<212> TYPE: PRT
<213> ORGANISM: Saccharomyces cerevisiae S288C

<400> SEQUENCE: 25

```
Met Ser Phe Glu Asn Leu His Lys Val Asn Ala Glu Ala Leu Glu Asp
1               5                   10                  15

Ala Val Val Glu Ile Cys Ser Ser Leu Gln Val Asp Ala Ala Lys Leu
            20                  25                  30

Asp Glu Leu Thr Ala Tyr Phe Ile Glu Cys Met Glu Lys Gly Leu Asn
        35                  40                  45

Asn Thr Ser Val Gly Glu Lys Thr Val Asp Lys Gly Leu Pro Met
    50                  55                  60

Ile Pro Thr Tyr Val Thr Ser Leu Pro Asn Gly Thr Glu Arg Gly Val
65                  70                  75                  80

Leu Leu Ala Ala Asp Leu Gly Gly Thr His Phe Arg Val Cys Ser Val
                85                  90                  95

Thr Leu Asn Gly Asp Gly Thr Phe Asp Met Gln Gln Leu Lys Ser Lys
            100                 105                 110

Ile Pro Glu Glu Tyr Leu Asn Asp Lys Asp Val Thr Ser Glu Glu Leu
        115                 120                 125

Phe Ser Tyr Leu Gly Arg Arg Thr Arg Ala Phe Val Arg Lys His His
    130                 135                 140

Pro Glu Leu Leu Lys Ser Thr Gly Glu Asn Ile Lys Pro Leu Lys Met
145                 150                 155                 160

Gly Phe Thr Phe Ser Tyr Pro Val Asp Gln Thr Ser Leu Ser Ser Gly
                165                 170                 175

Thr Leu Ile Arg Trp Thr Lys Ser Phe Lys Ile Glu Asp Thr Val Gly
            180                 185                 190

Lys Asp Val Val Arg Leu Tyr Gln Glu Gln Leu Asp Ile Gln Gly Leu
        195                 200                 205

Ser Met Ile Asn Val Val Ala Leu Thr Asn Asp Thr Val Gly Thr Phe
    210                 215                 220

Leu Ser His Cys Tyr Thr Ser Gly Ser Arg Pro Ser Ser Ala Gly Glu
225                 230                 235                 240

Ile Ser Glu Pro Val Ile Gly Cys Ile Phe Gly Thr Gly Thr Asn Gly
                245                 250                 255

Cys Tyr Met Glu Asp Ile Glu Asn Ile Lys Lys Leu Pro Asp Glu Leu
            260                 265                 270

Arg Thr Arg Leu Leu His Glu Gly Lys Thr Gln Met Cys Ile Asn Ile
        275                 280                 285

Glu Trp Gly Ser Phe Asp Asn Glu Leu Lys His Leu Ser Ala Thr Lys
    290                 295                 300

Tyr Asp Ile Asp Ile Asp Gln Lys Phe Ser Pro Asn Pro Gly Tyr His
305                 310                 315                 320

Leu Phe Glu Lys Arg Ile Ser Gly Met Tyr Leu Gly Glu Leu Leu Arg
                325                 330                 335

Asn Ile Leu Val Asp Leu His Ala Arg Gly Leu Ile Leu Gly Gln Tyr
            340                 345                 350

Arg Asn Tyr Asp Gln Leu Pro His Arg Leu Lys Thr Pro Phe Gln Leu
        355                 360                 365

Cys Ser Glu Val Leu Ser Arg Ile Glu Ile Asp Asp Ser Thr Asn Leu
    370                 375                 380

Arg Glu Thr Glu Leu Ser Phe Leu Gln Ser Leu Arg Leu Pro Thr Thr
```

```
            385                 390                 395                 400
        Phe Glu Glu Arg Lys Ala Ile Gln Asn Leu Val Arg Ser Ile Thr Arg
                        405                 410                 415

Arg Ser Ala Tyr Leu Ala Ala Val Pro Ile Ala Ala Ile Leu Ile Lys
                        420                 425                 430

Thr Asn Ala Leu Asn Lys Arg Tyr His Gly Glu Val Glu Ile Gly Phe
                        435                 440                 445

Asp Gly Tyr Val Ile Glu Tyr Tyr Pro Gly Phe Arg Ser Met Leu Arg
                    450                 455                 460

His Ala Leu Ala Leu Ser Pro Ile Gly Thr Glu Gly Glu Arg Lys Ile
        465                 470                 475                 480

His Leu Arg Leu Ala Lys Asp Gly Ser Gly Val Gly Ala Ala Leu Cys
                        485                 490                 495

Ala Leu Val Ala
                    500

<210> SEQ ID NO 26
<211> LENGTH: 433
<212> TYPE: PRT
<213> ORGANISM: Saccharomyces cerevisiae S288C

<400> SEQUENCE: 26

Met Thr Ile Glu Ser Thr Leu Ala Arg Glu Leu Glu Ser Leu Ile Leu
        1               5                   10                  15

Pro Ala Asp Ser Ile Val Asn Val Asp Gln Phe Gln Glu Glu Leu
                        20                  25                  30

Leu Ser Arg Leu Gln Thr Asn Thr Ile Ser Met Leu Pro Gln Cys Leu
                        35                  40                  45

Val Pro Asp Lys Arg Ser Arg Trp Asn Pro Glu Asp Lys Ile Leu Thr
                    50                  55                  60

Ile Asp Phe Gly Gly Thr Arg Leu Lys Phe Ala Ile Ile Ser Leu Pro
        65                  70                  75                  80

Gln Ile Val Ile Glu Tyr Asn Asp Ala Phe Glu Leu Thr Tyr Asn Ile
                        85                  90                  95

Val Asp Ser Asn Phe Phe Asn Gln Ile Ile Tyr Thr Ile Cys Thr Arg
                        100                 105                 110

Leu Ala Ala Asn Gly Tyr Ile Lys Lys Lys Asn Glu Ser Ser Glu Ala
                        115                 120                 125

Ser Lys Phe Phe Val Ser Val Thr Phe Ser Phe Pro Leu Asn Pro Glu
                    130                 135                 140

Gly Glu Val Val Ala Met Gly Lys Gly Phe Val Met Thr Asp Thr Leu
        145                 150                 155                 160

Gln Gly Ser Thr Val Lys Gln Leu Ile Gln Ser Ser Phe His Arg Ile
                        165                 170                 175

Ile Ser Glu Asn Ile Glu Glu Phe Phe Cys Thr Met Asn Val Cys His
                        180                 185                 190

Val Ile Asn Asp Ala Ile Ala Val Ser Leu Thr Ser Lys Phe Ile Cys
                        195                 200                 205

Glu Asn Asp Ser Ile Ser Leu Ile Ile Gly Thr Gly Thr Asn Ala Cys
                    210                 215                 220

Phe Glu Val Pro Tyr Gly Tyr Leu Pro Pro Phe Lys Arg Asp Ala Leu
        225                 230                 235                 240

Arg Glu Thr Leu Pro Ser Ser Tyr Asn Lys Glu Thr Leu Asn Phe Lys
                        245                 250                 255
```

His Val Leu Ile Asn Ser Glu Ile Gly Phe Ile Gly Lys Asn Val Ile
            260                 265                 270

Ala Leu Gln Pro Phe Asp Ile His Gly Ala Ile Ser Tyr Glu Met Pro
        275                 280                 285

Leu Glu Cys Val Thr Ser Gly Lys Trp Leu Pro Leu Ser Leu Lys Asn
    290                 295                 300

Ile Leu Leu Gln Tyr Asn Ile Pro Lys Asn Phe Pro Val Glu Phe
305                 310                 315                 320

Asn Gly Glu Leu Val Cys Gln Leu Ala Glu Asp Cys Thr Asn Ala Trp
                325                 330                 335

Phe Glu Asn Glu His Tyr Ala Leu Ile Cys Gln Ile Ala Arg Leu Leu
            340                 345                 350

Ile Lys Arg Ala Ala Phe Tyr Val Ala Ala Ile Val Gln Ala Ile Asp
        355                 360                 365

Ile Ile Thr Gly Cys Lys Asn Tyr Asn Phe Ile His Ile Gly Tyr Val
    370                 375                 380

Gly Ser Phe Leu His Asn Ser Asn Phe Tyr Arg Glu Gln Ile Lys Tyr
385                 390                 395                 400

Tyr Ser Ser Ile His Ile Lys Leu Gln Phe Leu Asn His Ser Asn Leu
                405                 410                 415

Leu Gly Ala Ala Ile Ala Thr Tyr Leu Asn Lys Ser Asp Asn Gln Val
            420                 425                 430

Gln

<210> SEQ ID NO 27
<211> LENGTH: 64
<212> TYPE: DNA
<213> ORGANISM: Artificial Sequence
<220> FEATURE:
<223> OTHER INFORMATION: Synthetic DNA

<400> SEQUENCE: 27
taatatacct ctatacttta acgtcaagga gaaaaacta taatgcagct gaagcttcgt    60
acgc                                                                64

<210> SEQ ID NO 28
<211> LENGTH: 66
<212> TYPE: DNA
<213> ORGANISM: Artificial Sequence
<220> FEATURE:
<223> OTHER INFORMATION: Synthetic DNA

<400> SEQUENCE: 28
aatgagaagt tgttctgaac aaagtaaaaa aaagaagtat acttacatag gccactagtg    60
gatctg                                                              66

<210> SEQ ID NO 29
<211> LENGTH: 25
<212> TYPE: DNA
<213> ORGANISM: Artificial Sequence
<220> FEATURE:
<223> OTHER INFORMATION: Synthetic DNA

<400> SEQUENCE: 29
atggcattat actcctgcta gaaag                                         25

<210> SEQ ID NO 30
<211> LENGTH: 24
<212> TYPE: DNA

<210> SEQ ID NO 30
<211> LENGTH: 24
<212> TYPE: DNA
<213> ORGANISM: Artificial Sequence
<220> FEATURE:
<223> OTHER INFORMATION: Synthetic DNA

<400> SEQUENCE: 30
aaaggatggc agagcatgtt atcg    24

<210> SEQ ID NO 31
<211> LENGTH: 24
<212> TYPE: DNA
<213> ORGANISM: Artificial Sequence
<220> FEATURE:
<223> OTHER INFORMATION: Synthetic DNA

<400> SEQUENCE: 31
gattgcgaga tccacgaaat tacc    24

<210> SEQ ID NO 32
<211> LENGTH: 24
<212> TYPE: DNA
<213> ORGANISM: Artificial Sequence
<220> FEATURE:
<223> OTHER INFORMATION: Synthetic DNA

<400> SEQUENCE: 32
aatcaccgga ttccttacca gttg    24

<210> SEQ ID NO 33
<211> LENGTH: 25
<212> TYPE: DNA
<213> ORGANISM: Artificial Sequence
<220> FEATURE:
<223> OTHER INFORMATION: Synthetic DNA

<400> SEQUENCE: 33
gaaattcacg ggatttattc gtgac    25

<210> SEQ ID NO 34
<211> LENGTH: 25
<212> TYPE: DNA
<213> ORGANISM: Artificial Sequence
<220> FEATURE:
<223> OTHER INFORMATION: Synthetic DNA

<400> SEQUENCE: 34
tttccatgtt tctaagcgta gtgag    25

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA

<400> SEQUENCE: 35
cccgtttgtt ggaagatagc    20

<210> SEQ ID NO 36
<211> LENGTH: 18
<212> TYPE: DNA
<213> ORGANISM: Artificial Sequence
<220> FEATURE:
<223> OTHER INFORMATION: Synthetic DNA

<400> SEQUENCE: 36
cacatcagcc atggaacc    18

<210> SEQ ID NO 37
<211> LENGTH: 19
<212> TYPE: DNA
<213> ORGANISM: Artificial Sequence
<220> FEATURE:
<223> OTHER INFORMATION: Synthetic DNA

<400> SEQUENCE: 37
gcaggtgctg ctgttattg                                            19

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA

<400> SEQUENCE: 38
ccgagctatc ctacgactttt c                                        21

<210> SEQ ID NO 39
<211> LENGTH: 23
<212> TYPE: DNA
<213> ORGANISM: Artificial Sequence
<220> FEATURE:
<223> OTHER INFORMATION: Synthetic DNA

<400> SEQUENCE: 39
gcccgacagg gtaacatatt atc                                       23

<210> SEQ ID NO 40
<211> LENGTH: 23
<212> TYPE: DNA
<213> ORGANISM: Artificial Sequence
<220> FEATURE:
<223> OTHER INFORMATION: Synthetic DNA

<400> SEQUENCE: 40
ccggaatcat aggaagacct ttg                                       23

<210> SEQ ID NO 41
<211> LENGTH: 24
<212> TYPE: DNA
<213> ORGANISM: Artificial Sequence
<220> FEATURE:
<223> OTHER INFORMATION: Synthetic DNA

<400> SEQUENCE: 41
agaggaaggt gcacttgaag attg                                      24

<210> SEQ ID NO 42
<211> LENGTH: 24
<212> TYPE: DNA
<213> ORGANISM: Artificial Sequence
<220> FEATURE:
<223> OTHER INFORMATION: Synthetic DNA

<400> SEQUENCE: 42
ataagatgga attggccggt cttg                                      24

<210> SEQ ID NO 43
<211> LENGTH: 1587
<212> TYPE: DNA
<213> ORGANISM: Saccharomyces cerevisiae CEN.PK 113-7D

<400> SEQUENCE: 43

```
atgactaaat ctcattcaga agaagtgatt gtacctgagt tcaattctag cgcaaaggaa      60
ttaccaagac cattggccga aaagtgcccg agcataatta agaaatttat aagcgcttat     120
gatgctaaac cggattttgt tgctagatcg cctggtagag tcaatctaat tggtgaacat     180
attgattatt gtgacttctc ggttttacct ttagctattg attttgatat gctttgcgcc     240
gtcaaagttt tgaacgagaa aaatccatcc attaccttaa taaatgctga tcccaaattt     300
gctcaaagga agttcgattt gccgttggac ggttcttatg tcacaattga tccttctgtg     360
tcagactggt ctaattactt taaatgtggt ctccatgttg ctcactcttt tctaaagaaa     420
cttgcaccgg aaaggtttgc cagtgctcct ctggccgggc tgcaagtctt ctgtgagggt     480
gatgtaccaa ctgcagtgg attgtcttct tcggccgcat tcatttgtgc cgttgcttta     540
gctgttgtta aagcgaatat gggccctggt tatcatatgt ccaagcaaaa tttaatgcgt     600
atcacggtcg ttgcagaaca ttatgttggt gttaacaatg gcggtatgga tcaggctgcc     660
tctgtttgcg gtgaggaaga tcatgctcta tacgttgagt caaaccgcca gttgaaggct     720
actccgttta aatttccgca attaaaaaac catgaaatta gctttgttat tgcgaacacc     780
cttgttgtat ctaacaagtt tgaaaccgcc ccaaccaact ataatttaag agtggtagaa     840
gtcactacag ctgcaaatgt tttagctgcc acgtacggtg ttgttttacc ttctggaaaa     900
gaaggatcga gcacgaataa aggtaatcta agagatttca tgaacgttta ttatgccaga     960
tatcacaaca tttccacacc ctggaacggc gatattgaat ccggcatcga acggttaaca    1020
aagatgctag tactagttga agagtctctc gccaataaga acagggctt tagtgttgac    1080
gatgtcgcgc aatccttgaa ttgttctcgc gaagaattca aagagacta cttaacaaca    1140
tctccagtga gatttcaagt cttaaagcta tatcagaggg ctaagcatgt gtattctgaa    1200
tcttttaagag tcttgaaggc tgtgaaatta atgactacag agagctttac tgccgatgaa    1260
gacttttttca agcaatttgg tgccttgatg aacgagtctc aagcttcttg cgataaactt    1320
tacgaatgtt cttgtccaga gattgacaaa atttgttcca ttgctttgtc aaatggatca    1380
tatggttccc gtttgaccgg agctggctgg ggtggttgta ctgttcactt ggttccaggg    1440
ggcccaaatg gcaacataga aaggtaaaa gaagcccttg ccaatgagtt ctacaaggtc    1500
aagtacccta agatcactga tgctgagctt gaaaatgcta ttatcgtctc taaaccagca    1560
ttgggcagct gtctatatga attataa                                         1587
```

<210> SEQ ID NO 44
<211> LENGTH: 1587
<212> TYPE: DNA
<213> ORGANISM: Saccharomyces cerevisiae IMK318

<400> SEQUENCE: 44

```
atgactaaat ctcattcaga agaagtgatt gtacctgagt tcaattctag cgcaaaggaa      60
ttaccaagac cattggccga aaagtgcccg agcataatta agaaatttat aagcgcttat     120
gatgctaaac cggattttgt tgctagatcg cctggtagag tcaatctaat tggtgaacat     180
attgattatt gtgacttctc ggttttacct ttagctattg attttgatat gctttgcgcc     240
gtcaaagttt tgaacgagaa aaatccatcc attaccttaa taaatgctga tcccaaattt     300
gctcaaagga agttcgattt gccgttggac ggttcttatg tcacaattga tccttctgtg     360
tcagactggt ctaattactt taaatgtggt ctccatgttg ctcactcttt tctaaagaaa     420
cttgcaccgg aaaggtttgc cagtgctcct ctggccgggc tgcaagtctt ctgtgagggt     480
```

```
gatgtaccaa ctggcagtgg attgtcttct tcggccgcat tcatttgtgc cgttgcttta    540
gctgttgtta aagcgaatat gggccctggt tatcatatgt ccaagcaaaa tttaatgcgt    600
atcacggtcg ttgcagaaca ttatgttggt gttaacaatg gcggtatgga tcaggctgcc    660
tctgtttgcg gtgaggaaga tcatgctcta tacgttgagt caaaccgca gttgaaggct     720 actccgttta aatttccgca attaaaaaac catgaaatta gctttgttat tgcgaacacc    780
cttgttgtat ctaacaagtt tgaaaccgcc caaccaact ataatttaag agtggtagaa     840
gtcactacag ctgcaaatgt tttagctgcc acgtacggtg ttgttttacc ttctggaaaa    900
gaaggatcga gcacgaataa aggtaatcta agagatttca tgaacgttta ttatgccaga   960
tatcacaaca tttccacacc ctggaacggc gatattgaat ccggcatcga acggttaaca    1020
aagatgctag tactagttga agagtctctc gccaataaga acagggctt tagtgttgac     1080 gatgtcgcgc aatccttgaa ttgttctcgc gaagaattca caagagtcta cttaacaaca   1140
tctccagtga gatttcaagt cttaaagcta tatcagaggg ctaagcatgt gtattctgaa    1200
tctttaagag tcttgaaggc tgtgaaatta atgactacag agagctttac tgccgatgaa    1260
gactttttca gcaatttggg tgccttgatg aacgagtctc aagcttcttg cgataaactt    1320
tacgaatgtt cttgtccaga gattgacaaa atttgttcca ttgctttgtc aaatggatca    1380
tatggttccc gtttgaccgg agctggctgg ggtggttgta ctgttcactt ggttccaggg    1440
ggcccaaatg gcaacataga aaggtaaaa gaagcccttg ccaatgagtt ctacaaggtc     1500
aagtacccta agatcactga tgctgagctt gaaaatgcta ttatcgtctc taaaccagca   1560
ttgggcagct gtctatatga attataa                                        1587

<210> SEQ ID NO 45
<211> LENGTH: 1587
<212> TYPE: DNA
<213> ORGANISM: Saccharomyces cerevisiae IMW017

<400> SEQUENCE: 45
atgactaaat ctcattcaga agaagtgatt gtacctgagt tcaattctag cgcaaaggaa     60
ttaccaagac cattggccga aaagtgcccg agcataatta agaaatttat aagcgcttat    120
gatgctaaac cggattttgt tgctagatcg cctggtagag tcaatctaat tggtgaacat    180
attgattatt gtgacttctc ggttttacct ttagctattg attttgatat gctttgcgcc    240
gtcaaagttt tgaacgagaa aaatccatcc attaccttaa taatgctga tcccaaattt    300 gctcaaagga agttcgattt gccgttggac ggttcttatg tcacaattga tccttctgtg    360
tcagactggt ctaattactt taaatgtggt ctccatgttg ctcactcttt tctaaagaaa    420
cttgcaccgg aaaggtttgc cagtgctcct ctggccgggc tgcaagtctt ctgtgagggt    480
gatgtaccaa ctggcagtgg attgtcttct tcggccgcat tcatttgtgc cgttgcttta    540
gctgttgtta aagcgaatat gggccctggt tatcatatgt ccaagcaaaa tttaatgcgt    600
atcacggtcg ttgcagaaca ttatgttggt gttaacaatg gcggtatgga tcaggctgcc    660
tctgtttgcg gtgaggaaga tcatgctcta tacgttgagt caaaccgca gttgaaggct     720 actccgttta aatttccgca attaaaaaac catgaaatta gctttgttat tgcgaacacc    780
cttgttgtat ctaacaagtt tgaaaccgcc caaccaact ttaatttaag agtggtagaa     840
gtcactacag ctgcaaatgt tttagctgcc acgtacggtg ttgttttacc ttctggaaaa    900
gaaggatcga gcacgaataa aggtaatcta agagatttca tgaacgttta ttatgccaga   960
```

```
tatcacaaca tttccacacc ctggaacggc gatattgaat ccggcatcga acggttaaca    1020
aagatgctag tactagttga agagtctctc gccaataaga acagggctt tagtgttgac    1080 gatgtcgcgc aatccttgaa ttgttctcgc gaagaattca caagagtcta cttaacaaca   1140
tctccagtga gatttcaagt cttaaagcta tatcagaggg ctaagcatgt gtattctgaa    1200
tctttaagag tcttgaaggc tgtgaaatta atgactacag agagctttac tgccgatgaa    1260
gactttttca agcaatttgg tgccttgatg aacgagtctc aagcttcttg cgataaactt    1320
tacgaatgtt cttgtccaga gattgacaaa atttgttcca ttgctttgtc aaatggatca    1380
tatggttccc gtttgaccgg agctggctgg ggtggttgta ctgttcactt ggttccaggg    1440
ggcccaaatg gcaacataga aaggtaaaa gaagcccttg ccaatgagtt ctacaaggtc     1500
aagtacccta agatcactga tgctgagctt gaaaatgcta ttatcgtctc taaaccagca    1560
ttgggcagct gtctatatga attataa                                      1587

<210> SEQ ID NO 46
<211> LENGTH: 1587
<212> TYPE: DNA
<213> ORGANISM: Saccharomyces cerevisiae IMW018

<400> SEQUENCE: 46
atgactaaat ctcattcaga agaagtgatt gtacctgagt tcaattctag cgcaaaggaa      60
ttaccaagac cattggccga aaagtgcccg agcataatta agaaatttat aagcgcttat     120
gatgctaaac cggattttgt tgctagatcg cctggtagag tcaatctaat tggtgaacat     180
attgattatt gtgacttctc ggttttacct ttagctattg attttgatat gctttgcgcc    240
gtcaaagttt tgaacgagaa aaatccatcc attaccttaa taaatgctga tcccaaattt    300
gctcaaagga agttcgattt gccgttggac ggttcttatg tcacaattga tccttctgtg    360
tcagactggt ctaattactt taaatgtggt ctccatgttg ctcactcttt tctaaagaaa    420
cttgcaccgg aaaggtttgc cagtgctcct ctggccgggc tgcaagtctt ctgtgagggt    480
gatgtaccaa ctggcagtgg attgtcttct tcggccgcat tcatttgtgc cgttgcttta    540
gctgttgtta aagcgaatat gggccctggt tatcatatgt ccaagcaaaa tttaatgcgt    600
atcacggtcg ttgcagaaca ttatgttggt gttaacaatg gcggtatgga tcaggctgcc    660
tctgtttgcg gtgaggaaga tcatgctcta tacgttgagt tcaaaccgca gttgaaggct    720
actccgttta aatttccgca attaaaaaac catgaaatta gctttgttat tgcgaacacc    780
cttgttgtat ctaacaagtt tgaaaccgcc ccaaccaact ataatttaag agtggtagaa    840
gtcactacag ctgcaaatgt tttagctgcc acgtacggtg ttgttttacc ttctggaaaa    900
gaaggatcga gcacgaataa aggtaatcta agagatttca tgaacgttta ttatgccaga    960
tatcacaaca tttccacacc ctggaacggc gatattgaat ccggcatcga acggttaaca   1020
aagatgctag tactagttga agagtctctc gccaataaga acagggctt tagtgttgac   1080 gatgtcgcgc aatccttgaa ttgttctcgc gaagaattca caagagtcta cttaacaaca  1140
tctccagtga gatttcaagt cttaaagcta tatcagaggg ctaagcatgt gtattctgaa   1200
tctttaagag tcttgaaggc tgtgaaatta atgactacag agagctttac tgccgatgaa   1260
gactttttca agcaatttgg tgccttgatg aacgagtctc aagcttcttg cgataaactt   1320
tacgaatgtt cttgtccaga gattgacaaa atttgttcca ttgctttgtc aaatggatca   1380
tatggttccc gtttgaccgg agctggctgg ggtggttgta ctgttcactt ggttccaggg   1440
ggcccaaatg gcaacataga aaggtaaaa gaagcccttg ccaatgagtt ctacaaggtc    1500
```

```
aagtacccta agatcactga tgctgagctt gaaaatgcta ttatcgtctc taaaccagca    1560
ttgggcagct gtctatatga attataa                                       1587

<210> SEQ ID NO 47
<211> LENGTH: 1725
<212> TYPE: DNA
<213> ORGANISM: Saccharomyces cerevisiae CEN.PK 113-7D

<400> SEQUENCE: 47
atggcagttg aggagaacaa tatgcctgtt gtttcacagc aaccccaagc tggtgaagac      60
gtgatctctt cactcagtaa agattcccat ttaagcgcac aatctcaaaa gtattccaat     120
gatgaattga aagccggtga gtcagggcct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg ggtttgttgt ccaaacagac     300
tttttgagaa ggtttggtat gaaacataag gatggtaccc actatttgtc aaacgtcaga     360
acaggtttaa tcgtcgccat tttcaatatt ggctgtgcct ttggtggtat tatactttcc     420
aaaggtggag atatgtatgg ccgtaaaaag ggtctttcga ttgtcgtctc ggtttatata     480
gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatctttt tgggctactg tactaattac ggtacaaaga gctattcgaa ctcagttcaa     720
tggagagttc cattagggct atgtttcgct tggtcattat ttatgattgg cgctttgacg     780
ttagttcctg aatccccacg ttatttatgt gaggtgaata aggtagaaga cgccaagctt     840
tccattgcta agtctaacaa ggtgtcacca gaggatcctg ccgtccaggc agagttagat     900
ctgatcatgg ccggtataga agctgaaaaa ctggctggca atgcgtcctg ggggaatta      960 ttttccacca gaccaaagt atttcaacgt tgttgatgg gtgtatttgt tcaaatgttc     1020
caacaattaa ccggtaacaa ttatttttc tactacggta ccgttatttt caagtcagtt    1080
ggcctggatg attcctttga acatccatt gtcattggtg tagtcaactt tgcctccact    1140
ttctttagtt tgtggactgt cgaaaacttg gggcgtcgta atgtttact tttgggcgct    1200 gccactatga tggcttgtat ggtcatctac gcctctgttg gtgttaccag attatatcct    1260
cacggtaaaa gccagccatc ttctaaaggt gccggtaact gtatgattgt cttacctgt    1320 tttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgttttttt atgtcttttt ctttgttcca    1560
gaaactaaag gctatcgtt agaagaaatt caagaattat gggaagaagg tgtttttaccct    1620 tggaaatctg aaggctggat tccttcatcc agaagaggta ataattacga tttagaggat    1680
ttacaacatg acgacaaacc gtggtacaag gccatgctag aataa                    1725

<210> SEQ ID NO 48
<211> LENGTH: 1725
<212> TYPE: DNA
<213> ORGANISM: Saccharomyces cerevisiae IMK318

<400> SEQUENCE: 48
```

```
atggcagttg aggagaacaa tatgcctgtt gtttcacagc aaccccaagc tggtgaagac    60
gtgatctctt cactcagtaa agattcccat ttaagcgcac aatctcaaaa gtattccaat   120
gatgaattga aagccggtga gtcagggcct gaaggctccc aaagtgttcc tatagagata   180
cccaagaagc ccatgtctga atatgttacc gtttccttgc tttgtttgtg tgttgccttc   240
ggcggcttca tgtttggctg ggataccggt actatttctg ggtttgttgt ccaaacagac   300
tttttgagaa ggtttggtat gaaacataag gatggtaccc actatttgtc aaacgtcaga   360
acaggtttaa tcgtcgccat tttcaatatt ggctgtgcct tggtggtat tatactttcc    420
aaaggtggag atatgtatgg ccgtaaaaag ggtctttcga ttgtcgtctc ggtttatata   480
gttggtatta tcattcaaat tgcctctatc aacaagtggt accaatattt cattggtaga   540
atcatatctg gtttggtgt cggcggcatc gccgtcttat gtcctatgtt gatctctgaa    600
attgctccaa agcacttgag aggcacacta gtttcttgtt atcagctgat gattactgca   660
ggtatctttt gggctactg tactaattac ggtacaaaga gctattcgaa ctcagttcaa    720
tggagagttc cattagggct atgtttcgct tggtcattat ttatgattgg cgctttgacg   780
ttagttcctg aatccccacg ttatttatgt gaggtgaata aggtagaaga cgccaagctt   840
tccattgcta agtctaacaa ggtgtcacca gaggatcctg ccgtccaggc agagttagat   900
ctgatcatgg ccgtatagaa agctgaaaaa ctggctggca atgcgtcctg ggggaatta   960
ttttccacca agaccaaagt atttcaacgt tgttgatgg gtgtatttgt tcaaatgttc   1020
caacaattaa ccgtaacaa ttattttttc tactacggta ccgttatttt caagtcagtt   1080
ggcctggatg attcctttga acatccatt gtcattggtg tagtcaactt tgcctccact   1140
ttctttagtt tgtggactgt cgaaaacttg gggcgtcgta atgtttact tttgggcgct   1200
gccactatga tggcttgtat ggtcatctac gcctctgttg gtgttaccag attatatcct   1260
cacggtaaaa gccagccatc ttctaaaggt gccggtaact gtatgattgt ctttacctgt   1320
ttttatattt tctgttatgc cacaacctgg gcgccagttg cctgggtcat cacagcagaa   1380
tcattcccac tgagagtcaa gtcgaaatgt atggcgttgg cctctgcttc caattgggta   1440
tgggggttct tgattgcatt tttcaccccca ttcatcacat ctgccattaa cttctactac   1500
ggttatgtct tcatgggctg tttggttgcc atgtttttt atgtctttt ctttgttcca   1560
gaaactaaag gcctatcgtt agaagaaatt caagaattat gggaagaagg tgttttacct   1620
tggaaatctg aaggctggat tccttcatcc agaagaggta ataattacga tttagaggat   1680
ttacaacatg acgacaaacc gtggtacaag gccatgctag aataa                  1725
```

<210> SEQ ID NO 49
<211> LENGTH: 1725
<212> TYPE: DNA
<213> ORGANISM: Saccharomyces cerevisiae IMW017

<400> SEQUENCE: 49

```
atggcagttg aggagaacaa tatgcctgtt gtttcacagc aaccccaagc tggtgaagac    60
gtgatctctt cactcagtaa agattcccat ttaagcgcac aatctcaaaa gtattccaat   120
gatgaattga aagccggtga gtcagggcct gaaggctccc aaagtgttcc tatagagata   180
cccaagaagc ccatgtctga atatgttacc gtttccttgc tttgtttgtg tgttgccttc   240
ggcggcttca tgtttggctg ggataccggt actatttctg ggtttgttgt ccaaacagac   300
tttttgagaa ggtttggtat gaaacataag gatggtaccc actatttgtc aaacgtcaga   360
acaggtttaa tcgtcgccat tttcaatatt ggctgtgcct tggtggtat tatactttcc    420
```

```
aaaggtggag atatgtatgg ccgtaaaaag ggtctttcga ttgtcgtctc ggtttatata    480
gttggtatta tcattcaaat tgcctctatc aacaagtggt accaatattt cattggtaga    540
atcatatctg gtttgggtgt cggcggcatc gccgtcttat gtcctatgtt gatctctgaa    600
attgctccaa agcacttgag aggcacacta gtttcttgtt atcagctgat gattaatgca    660
ggtatctttt tgggctactg tactaattac ggtacaaaga gctattcgaa ctcagttcaa    720
tggagagttc cattagggct atgtttcgct tggtcattat ttatgattgg cgctttgacg    780
ttagttcctg aatccccacg ttatttatgt gaggtgaata aggtagaaga cgccaagctt    840
tccattgcta agtctaacaa ggtgtcacca gaggatcctg ccgtccaggc agagttagat    900
ctgatcatgg ccggtataga agctgaaaaa ctggctggca atgcgtcctg gggggaatta    960
ttttccacca agaccaaagt atttcaacgt tgttgatgg gtgtatttgt tcaaatgttc    1020
caacaattaa ccgtaacaa ttattttttc tactacggta ccgttatttt caagtcagtt    1080
ggcctggatg attcctttga acatccatt gtcattggtg tagtcaactt tgcctccact    1140
ttctttagtt tgtggactgt cgaaaacttg gggcgtcgta atgtttact tttgggcgct    1200 gccactatga tggcttgtat ggtcatctac gcctctgttg gtgttaccag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgtttttt atgtctttt ctttgttcca    1560 gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa               1725
```

<210> SEQ ID NO 50
<211> LENGTH: 1725
<212> TYPE: DNA
<213> ORGANISM: Saccharomyces cerevisiae IMW018

<400> SEQUENCE: 50

```
atggcagttg aggagaacaa tatgcctgtt gtttcacagc aaccccaagc tggtgaagac     60
gtgatctctt cactcagtaa agattcccat ttaagcgcac aatctcaaaa gtattccaat    120
gatgaattga aagccggtga gtcagggcct gaaggctccc aaagtgttcc tatagagata    180
cccaagaagc ccatgtctga atatgttacc gtttccttgc tttgtttgtg tgttgccttc    240
ggcggcttca tgtttggctg ggataccggt actatttctg ggtttgttgt ccaaacagac    300 ttttttgagaa ggtttggtat gaaacataag gatggtaccc actatttgtc aaacgtcaga    360
acaggtttaa tcgtcgccat tttcaatatt ggctgtgcct ttggtggtat tatactttcc    420
aaaggtggag atatgtatgg ccgtaaaaag ggtctttcga ttgtcgtctc ggtttatata    480
gttggtatta tcattcaaat tgcctctatc aacaagtggt accaatattt cattggtaga    540
atcatatctg gtttgggtgt cggcggcatc gccgtcttat gtcctatgtt gatctctgaa    600
attgctccaa agcacttgag aggcacacta gtttcttgtt atcagctgat gattactgca    660
ggtatctttt tgggctactg tactaattac ggtacaaaga gctattcgaa ctcagttcaa    720
tggagagttc cattagggct atgtttcgct tggtcattat ttatgattgg cgctttgacg    780
```

```
ttagttcctg aatccccacg ttatttatgt gaggtgaata aggtagaaga cgccaagctt      840
tccattgcta agtctaacaa ggtgtcacca gaggatcctg ccgtccaggc agagttagat      900
ctgatcatgg ccggtataga agctgaaaaa ctggctggca atgcgtcctg ggggaatta      960
ttttccacca agaccaaagt atttcaacgt tgttgatgg gtgtatttgt tcaaatgttc     1020
caacaattaa ccggtaacaa ttattttttc tactacggta ccgttatttt caagtcagtt     1080
ggcctggatg attcctttga aacatccatt gtcattggtg tagtcagctt tgcctccact     1140
ttctttagtt tgtggactgt cgaaaacttg gggcgtcgta atgtttact tttgggcgct      1200
gccactatga tggcttgtat ggtcatctac gcctctgttg gtgttaccag attatatcct     1260
cacggtaaaa gccagccatc ttctaaaggt gccggtaact gtatgattgt ctttacctgt     1320
ttttatattt tctgttatgc cacaacctgg gcgccagttg cctgggtcat cacagcagaa     1380
tcattcccac tgagagtcaa gtcgaaatgt atggcgttgg cctctgcttc caattgggta     1440
tgggggttct tgattgcatt tttcacccca ttcatcacat ctgccattaa cttctactac     1500
ggttatgtct tcatgggctg tttggttgcc atgtttttt atgtcttttt ctttgttcca     1560
gaaactaaag gcctatcgtt agaagaaatt caagaattat gggaagaagg tgttttacct     1620
tggaaatctg aaggctggat tccttcatcc agaagaggta ataattacga tttagaggat     1680
ttacaacatg acgacaaacc gtggtacaag gccatgctag aataa                    1725
```

<210> SEQ ID NO 51
<211> LENGTH: 528
<212> TYPE: PRT
<213> ORGANISM: Saccharomyces cerevisiae CEN.PK 113-7D

<400> SEQUENCE: 51

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ala Ala Phe Ile Cys
            165                 170                 175

Ala Val Ala Leu Ala Val Val Lys Ala Asn Met Gly Pro Gly Tyr His
        180                 185                 190

Met Ser Lys Gln Asn Leu Met Arg Ile Thr Val Val Ala Glu His Tyr
    195                 200                 205

```
Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
        275                 280                 285

Ala Ala Thr Tyr Gly Val Val Leu Pro Ser Gly Lys Glu Gly Ser Ser
    290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
                325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
        355                 360                 365

Ser Arg Glu Glu Phe Thr Arg Asp Tyr Leu Thr Thr Ser Pro Val Arg
    370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
                405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
        435                 440                 445

Asp Lys Ile Cys Ser Ile Ala Leu Ser Asn Gly Ser Tyr Gly Ser Arg
    450                 455                 460

Leu Thr Gly Ala Gly Trp Gly Gly Cys Thr Val His Leu Val Pro Gly
465                 470                 475                 480

Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
        515                 520                 525

<210> SEQ ID NO 52
<211> LENGTH: 528
<212> TYPE: PRT
<213> ORGANISM: Saccharomyces cerevisiae IMK318

<400> SEQUENCE: 52

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60
```

-continued

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
            85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
            115                 120                 125

Cys Gly Leu His Val Ala His Ser Phe Leu Lys Lys Leu Ala Pro Glu
            130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ala Ala Phe Ile Cys
            165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
            195                 200                 205

Val Gly Val Asn Asn Gly Gly Met Asp Gln Ala Ala Ser Val Cys Gly
210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
            245                 250                 255

Ile Ala Asn Thr Leu Val Val Ser Asn Lys Phe Glu Thr Ala Pro Thr
            260                 265                 270

Asn Tyr Asn Leu Arg Val Val Glu Val Thr Thr Ala Ala Asn Val Leu
            275                 280                 285

Ala Ala Thr Tyr Gly Val Val Leu Pro Ser Gly Lys Glu Gly Ser Ser
            290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
            325                 330                 335

Glu Arg Leu Thr Lys Met Leu Val Leu Val Glu Glu Ser Leu Ala Asn
            340                 345                 350

Lys Lys Gln Gly Phe Ser Val Asp Asp Val Ala Gln Ser Leu Asn Cys
            355                 360                 365

Ser Arg Glu Glu Phe Thr Arg Val Tyr Leu Thr Thr Ser Pro Val Arg
            370                 375                 380

Phe Gln Val Leu Lys Leu Tyr Gln Arg Ala Lys His Val Tyr Ser Glu
385                 390                 395                 400

Ser Leu Arg Val Leu Lys Ala Val Lys Leu Met Thr Thr Glu Ser Phe
            405                 410                 415

Thr Ala Asp Glu Asp Phe Phe Lys Gln Phe Gly Ala Leu Met Asn Glu
            420                 425                 430

Ser Gln Ala Ser Cys Asp Lys Leu Tyr Glu Cys Ser Cys Pro Glu Ile
            435                 440                 445

Asp Lys Ile Cys Ser Ile Ala Leu Ser Asn Gly Ser Tyr Gly Ser Arg
            450                 455                 460

Leu Thr Gly Ala Gly Trp Gly Gly Cys Thr Val His Leu Val Pro Gly
465                 470                 475                 480

```
Gly Pro Asn Gly Asn Ile Glu Lys Val Lys Glu Ala Leu Ala Asn Glu
                485                 490                 495

Phe Tyr Lys Val Lys Tyr Pro Lys Ile Thr Asp Ala Glu Leu Glu Asn
            500                 505                 510

Ala Ile Ile Val Ser Lys Pro Ala Leu Gly Ser Cys Leu Tyr Glu Leu
        515                 520                 525

<210> SEQ ID NO 53
<211> LENGTH: 528
<212> TYPE: PRT
<213> ORGANISM: Saccharomyces cerevisiae IMW017

<400> SEQUENCE: 53

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
            20                  25                  30

Ile Lys Lys Phe Ile Ser Ala Tyr Asp Ala Lys Pro Asp Phe Val Ala
        35                  40                  45

Arg Ser Pro Gly Arg Val Asn Leu Ile Gly Glu His Ile Asp Tyr Cys
    50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                85                  90                  95

Asp Pro Lys Phe Ala Gln Arg Lys Phe Asp Leu Pro Leu Asp Gly Ser
            100                 105                 110

Tyr Val Thr Ile Asp Pro Ser Val Ser Asp Trp Ser Asn Tyr Phe Lys
        115                 120                 125

Cys Gly Leu His Val Ala His Ser Phe Leu Lys Lys Leu Ala Pro Glu
    130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                165                 170                 175

Ala Val Ala Leu Ala Val Val Lys Ala Asn Met Gly Pro Gly Tyr His
            180                 185                 190

Met Ser Lys Gln Asn Leu Met Arg Ile Thr Val Val Ala Glu His Tyr
        195                 200                 205

Val Gly Val Asn Asn Gly Gly Met Asp Gln Ala Ala Ser Val Cys Gly
    210                 215                 220

Glu Glu Asp His Ala Leu Tyr Val Glu Phe Lys Pro Gln Leu Lys Ala
225                 230                 235                 240

Thr Pro Phe Lys Phe Pro Gln Leu Lys Asn His Glu Ile Ser Phe Val
                245                 250                 255

Ile Ala Asn Thr Leu Val Val Ser Asn Lys Phe Glu Thr Ala Pro Thr
            260                 265                 270

Asn Phe Asn Leu Arg Val Val Glu Val Thr Thr Ala Ala Asn Val Leu
        275                 280                 285

Ala Ala Thr Tyr Gly Val Leu Pro Ser Gly Lys Glu Gly Ser Ser
    290                 295                 300

Thr Asn Lys Gly Asn Leu Arg Asp Phe Met Asn Val Tyr Tyr Ala Arg
305                 310                 315                 320

Tyr His Asn Ile Ser Thr Pro Trp Asn Gly Asp Ile Glu Ser Gly Ile
                325                 330                 335
```

Glu Arg Leu Thr Lys Met Leu Val Leu Val Glu Ser Leu Ala Asn
             340                 345                 350

Lys Lys Gln Gly Phe Ser Val Asp Val Ala Gln Ser Leu Asn Cys
             355                 360                 365

Ser Arg Glu Glu Phe Thr Arg Val Tyr Leu Thr Thr Ser Pro Val Arg
             370                 375                 380

Phe Gln Val Leu Lys Leu Tyr Gln Arg Ala Lys His Val Tyr Ser Glu
385                      390                 395                 400

Ser Leu Arg Val Leu Lys Ala Val Lys Leu Met Thr Thr Glu Ser Phe
                 405                 410                 415

Thr Ala Asp Glu Asp Phe Phe Lys Gln Phe Gly Ala Leu Met Asn Glu
             420                 425                 430

Ser Gln Ala Ser Cys Asp Lys Leu Tyr Glu Cys Ser Cys Pro Glu Ile
             435                 440                 445

Asp Lys Ile Cys Ser Ile Ala Leu Ser Asn Gly Ser Tyr Gly Ser Arg
450                      455                 460

Leu Thr Gly Ala Gly Trp Gly Gly Cys Thr Val His Leu Val Pro Gly
465                      470                 475                 480

Gly Pro Asn Gly Asn Ile Glu Lys Val Lys Glu Ala Leu Ala Asn Glu
             485                 490                 495

Phe Tyr Lys Val Lys Tyr Pro Lys Ile Thr Asp Ala Glu Leu Glu Asn
                 500                 505                 510

Ala Ile Ile Val Ser Lys Pro Ala Leu Gly Ser Cys Leu Tyr Glu Leu
             515                 520                 525

<210> SEQ ID NO 54
<211> LENGTH: 528
<212> TYPE: PRT
<213> ORGANISM: Saccharomyces cerevisiae IMW018

<400> SEQUENCE: 54

Met Thr Lys Ser His Ser Glu Glu Val Ile Val Pro Glu Phe Asn Ser
1               5                   10                  15

Ser Ala Lys Glu Leu Pro Arg Pro Leu Ala Glu Lys Cys Pro Ser Ile
             20                  25                  30

Ile Lys Lys Phe Ile Ser Ala Tyr Asp Ala Lys Pro Asp Phe Val Ala
             35                  40                  45

Arg Ser Pro Gly Arg Val Asn Leu Ile Gly Glu His Ile Asp Tyr Cys
         50                  55                  60

Asp Phe Ser Val Leu Pro Leu Ala Ile Asp Phe Asp Met Leu Cys Ala
65                  70                  75                  80

Val Lys Val Leu Asn Glu Lys Asn Pro Ser Ile Thr Leu Ile Asn Ala
                 85                  90                  95

Asp Pro Lys Phe Ala Gln Arg Lys Phe Asp Leu Pro Leu Asp Gly Ser
             100                 105                 110

Tyr Val Thr Ile Asp Pro Ser Val Ser Asp Trp Ser Asn Tyr Phe Lys
             115                 120                 125

Cys Gly Leu His Val Ala His Ser Phe Leu Lys Lys Leu Ala Pro Glu
         130                 135                 140

Arg Phe Ala Ser Ala Pro Leu Ala Gly Leu Gln Val Phe Cys Glu Gly
145                 150                 155                 160

Asp Val Pro Thr Gly Ser Gly Leu Ser Ser Ser Ala Ala Phe Ile Cys
                 165                 170                 175

Ala Val Ala Leu Ala Val Val Lys Ala Asn Met Gly Pro Gly Tyr His

```
            180                 185                 190
Met Ser Lys Gln Asn Leu Met Arg Ile Thr Val Val Ala Glu His Tyr
        195                 200                 205
Val Gly Val Asn Asn Gly Gly Met Asp Gln Ala Ala Ser Val Cys Gly
        210                 215                 220
Glu Glu Asp His Ala Leu Tyr Val Glu Phe Lys Pro Gln Leu Lys Ala
225                 230                 235                 240
Thr Pro Phe Lys Phe Pro Gln Leu Lys Asn His Glu Ile Ser Phe Val
                245                 250                 255
Ile Ala Asn Thr Leu Val Val Ser Asn Lys Phe Glu Thr Ala Pro Thr
            260                 265                 270
Asn Tyr Asn Leu Arg Val Val Glu Val Thr Ala Ala Asn Val Leu
        275                 280                 285
Ala Ala Thr Tyr Gly Val Leu Pro Ser Gly Lys Glu Gly Ser Ser
        290                 295                 300
Thr Asn Lys Gly Asn Leu Arg Asp Phe Met Asn Val Tyr Tyr Ala Arg
305                 310                 315                 320
Tyr His Asn Ile Ser Thr Pro Trp Asn Gly Asp Ile Glu Ser Gly Ile
                325                 330                 335
Glu Arg Leu Thr Lys Met Leu Val Val Glu Ser Leu Ala Asn
            340                 345                 350
Lys Lys Gln Gly Phe Ser Val Asp Asp Val Ala Gln Ser Leu Asn Cys
        355                 360                 365
Ser Arg Glu Glu Phe Thr Arg Val Tyr Leu Thr Thr Ser Pro Val Arg
        370                 375                 380
Phe Gln Val Leu Lys Leu Tyr Gln Arg Ala Lys His Val Tyr Ser Glu
385                 390                 395                 400
Ser Leu Arg Val Leu Lys Ala Val Lys Leu Met Thr Thr Glu Ser Phe
                405                 410                 415
Thr Ala Asp Glu Asp Phe Phe Lys Gln Phe Gly Ala Leu Met Asn Glu
            420                 425                 430
Ser Gln Ala Ser Cys Asp Lys Leu Tyr Glu Cys Ser Cys Pro Glu Ile
        435                 440                 445
Asp Lys Ile Cys Ser Ile Ala Leu Ser Asn Gly Ser Tyr Gly Ser Arg
        450                 455                 460
Leu Thr Gly Ala Gly Trp Gly Gly Cys Thr Val His Leu Val Pro Gly
465                 470                 475                 480
Gly Pro Asn Gly Asn Ile Glu Lys Val Lys Glu Ala Leu Ala Asn Glu
                485                 490                 495
Phe Tyr Lys Val Lys Tyr Pro Lys Ile Thr Asp Ala Glu Leu Glu Asn
            500                 505                 510
Ala Ile Val Ser Lys Pro Ala Leu Gly Ser Cys Leu Tyr Glu Leu
        515                 520                 525

<210> SEQ ID NO 55
<211> LENGTH: 574
<212> TYPE: PRT
<213> ORGANISM: Saccharomyces cerevisiae CEN.PK 113-7D

<400> SEQUENCE: 55

Met Ala Val Glu Glu Asn Asn Met Pro Val Val Ser Gln Gln Pro Gln
1               5                   10                  15
Ala Gly Glu Asp Val Ile Ser Ser Leu Ser Lys Asp Ser His Leu Ser
            20                  25                  30
```

-continued

```
Ala Gln Ser Gln Lys Tyr Ser Asn Asp Glu Leu Lys Ala Gly Glu Ser
         35                  40                  45

Gly Pro Glu Gly Ser Gln Ser Val Pro Ile Glu Ile Pro Lys Lys Pro
 50                  55                  60

Met Ser Glu Tyr Val Thr Val Ser Leu Leu Cys Leu Cys Val Ala Phe
 65                  70                  75                  80

Gly Gly Phe Met Phe Gly Trp Asp Thr Gly Thr Ile Ser Gly Phe Val
                 85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
                115                 120                 125

Asn Ile Gly Cys Ala Phe Gly Gly Ile Ile Leu Ser Lys Gly Gly Asp
130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365

Ser Ile Val Ile Gly Val Val Asn Phe Ala Ser Thr Phe Phe Ser Leu
370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
        435                 440                 445

Thr Trp Ala Pro Val Ala Trp Val Ile Thr Ala Glu Ser Phe Pro Leu
```

```
                    450             455             460
Arg Val Lys Ser Lys Cys Met Ala Leu Ala Ser Ala Ser Asn Trp Val
465                 470             475                 480

Trp Gly Phe Leu Ile Ala Phe Thr Pro Phe Ile Thr Ser Ala Ile
                485             490             495

Asn Phe Tyr Tyr Gly Tyr Val Phe Met Gly Cys Leu Val Ala Met Phe
            500             505             510

Phe Tyr Val Phe Phe Val Pro Glu Thr Lys Gly Leu Ser Leu Glu
            515             520             525

Glu Ile Gln Glu Leu Trp Glu Glu Gly Val Leu Pro Trp Lys Ser Glu
            530             535             540

Gly Trp Ile Pro Ser Ser Arg Arg Gly Asn Asn Tyr Asp Leu Glu Asp
545             550             555                 560

Leu Gln His Asp Asp Lys Pro Trp Tyr Lys Ala Met Leu Glu
                565             570

<210> SEQ ID NO 56
<211> LENGTH: 574
<212> TYPE: PRT
<213> ORGANISM: Saccharomyces cerevisiae IMK318

<400> SEQUENCE: 56

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255
```

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365

Ser Ile Val Ile Gly Val Val Asn Phe Ala Ser Thr Phe Phe Ser Leu
    370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
        435                 440                 445

Thr Trp Ala Pro Val Ala Trp Val Ile Thr Ala Glu Ser Phe Pro Leu
    450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
            500                 505                 510

Phe Tyr Val Phe Phe Phe Val Pro Glu Thr Lys Gly Leu Ser Leu Glu
        515                 520                 525

Glu Ile Gln Glu Leu Trp Glu Glu Gly Val Leu Pro Trp Lys Ser Glu
    530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570

<210> SEQ ID NO 57
<211> LENGTH: 574
<212> TYPE: PRT
<213> ORGANISM: Saccharomyces cerevisiae IMW017

<400> SEQUENCE: 57

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

```
Met Ser Glu Tyr Val Thr Val Ser Leu Leu Cys Leu Cys Val Ala Phe
 65                  70                  75                  80

Gly Gly Phe Met Phe Gly Trp Asp Thr Gly Thr Ile Ser Gly Phe Val
                 85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Asn Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365

Ser Ile Val Ile Gly Val Val Asn Phe Ala Ser Thr Phe Phe Ser Leu
    370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
        435                 440                 445

Thr Trp Ala Pro Val Ala Trp Val Ile Thr Ala Glu Ser Phe Pro Leu
    450                 455                 460

Arg Val Lys Ser Lys Cys Met Ala Leu Ala Ser Ala Ser Asn Trp Val
465                 470                 475                 480
```

```
Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
            500                 505                 510

Phe Tyr Val Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
            530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570

<210> SEQ ID NO 58
<211> LENGTH: 574
<212> TYPE: PRT
<213> ORGANISM: Saccharomyces cerevisiae IMW018

<400> SEQUENCE: 58

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65              70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285
```

```
Ser Pro Glu Asp Pro Ala Val Gln Ala Glu Leu Asp Leu Ile Met Ala
    290             295                 300
Gly Ile Glu Ala Glu Lys Leu Ala Gly Asn Ala Ser Trp Gly Glu Leu
305             310              315                 320
Phe Ser Thr Lys Thr Lys Val Phe Gln Arg Leu Leu Met Gly Val Phe
                325                 330                 335
Val Gln Met Phe Gln Gln Leu Thr Gly Asn Asn Tyr Phe Phe Tyr Tyr
                340             345                 350
Gly Thr Val Ile Phe Lys Ser Val Gly Leu Asp Asp Ser Phe Glu Thr
            355             360                 365
Ser Ile Val Ile Gly Val Val Ser Phe Ala Ser Thr Phe Phe Ser Leu
    370             375                 380
Trp Thr Val Glu Asn Leu Gly Arg Arg Lys Cys Leu Leu Leu Gly Ala
385             390             395                 400
Ala Thr Met Met Ala Cys Met Val Ile Tyr Ala Ser Val Gly Val Thr
                405             410                 415
Arg Leu Tyr Pro His Gly Lys Ser Gln Pro Ser Ser Lys Gly Ala Gly
            420             425                 430
Asn Cys Met Ile Val Phe Thr Cys Phe Tyr Ile Phe Cys Tyr Ala Thr
            435             440                 445
Thr Trp Ala Pro Val Ala Trp Val Ile Thr Ala Glu Ser Phe Pro Leu
            450             455                 460
Arg Val Lys Ser Lys Cys Met Ala Leu Ala Ser Ala Ser Asn Trp Val
465             470                 475                 480
Trp Gly Phe Leu Ile Ala Phe Phe Thr Pro Phe Ile Thr Ser Ala Ile
                485             490                 495
Asn Phe Tyr Tyr Gly Tyr Val Phe Met Gly Cys Leu Val Ala Met Phe
            500             505                 510
Phe Tyr Val Phe Phe Phe Val Pro Glu Thr Lys Gly Leu Ser Leu Glu
            515             520                 525
Glu Ile Gln Glu Leu Trp Glu Glu Gly Val Leu Pro Trp Lys Ser Glu
    530             535                 540
Gly Trp Ile Pro Ser Ser Arg Arg Gly Asn Asn Tyr Asp Leu Glu Asp
545             550                 555                 560
Leu Gln His Asp Asp Lys Pro Trp Tyr Lys Ala Met Leu Glu
                565             570
```